(12) United States Patent
Das et al.

(10) Patent No.: US 7,557,211 B2
(45) Date of Patent: Jul. 7, 2009

(54) 8H-IMIDAZO[4,5-D]THIAZOLO[4,5-B]PYRIDINE BASED TRICYCLIC COMPOUNDS AND PHARMACEUTICAL COMPOSITIONS COMPRISING SAME

(75) Inventors: Jagabandhu Das, Mercerville, NJ (US); James Kempson, Princeton, NJ (US); William J. Pitts, Newtown, PA (US); Steven H. Spergel, Warrington, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 593 days.

(21) Appl. No.: 11/271,598

(22) Filed: Nov. 10, 2005

(65) Prior Publication Data

US 2006/0128741 A1    Jun. 15, 2006

Related U.S. Application Data

(60) Provisional application No. 60/627,538, filed on Nov. 12, 2004.

(51) Int. Cl.
C07D 417/14      (2006.01)
(52) U.S. Cl. .......................................... 546/83; 514/293
(58) Field of Classification Search ................... 546/83; 514/293
See application file for complete search history.

(56) References Cited

U.S. PATENT DOCUMENTS

| 4,131,677 | A | 12/1978 | Shen et al. |
| 6,933,294 | B2 | 8/2005 | Belema et al. |
| 2003/0045545 | A1 | 3/2003 | Gerster et al. |
| 2003/0078277 | A1 | 4/2003 | Hibi et al. |
| 2003/0212093 | A1 | 11/2003 | Gerster et al. |
| 2004/0132766 | A1 | 7/2004 | Griesgraber |
| 2004/0204432 | A1 | 10/2004 | Qiu et al. |
| 2005/0038054 | A1 | 2/2005 | Combs et al. |
| 2005/0101626 | A1 | 5/2005 | Pitts et al. |

FOREIGN PATENT DOCUMENTS

WO    WO 01/00587    1/2001

OTHER PUBLICATIONS

Dorwald F. A. Side Reactions in Organic Synthesis, 2005, Wiley: VCH, Weinheim p. IX of Preface.*
U.S. Appl. No. 11/272,401, filed Nov. 10, 2005, Not yet published, Dyckman et al.

* cited by examiner

Primary Examiner—Rita J Desai
(74) Attorney, Agent, or Firm—Mary K. VanAtten

(57) ABSTRACT

The present invention provides for thiazolopyridine-based tricyclic compounds having the formula (I),

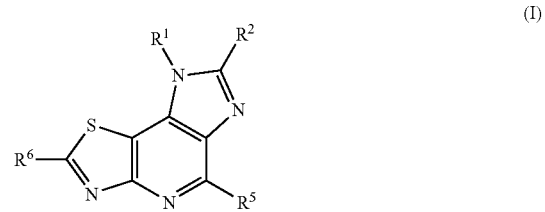

wherein $R^1$, $R^2$, $R^5$ and $R^6$ are as described herein. The present invention further provides pharmaceutical compositions comprising such compounds, as well as the use of such compounds for treating inflammatory and immune diseases.

6 Claims, 1 Drawing Sheet

8H-IMIDAZO[4,5-D]THIAZOLO[4,5-B]PYRIDINE BASED TRICYCLIC COMPOUNDS AND PHARMACEUTICAL COMPOSITIONS COMPRISING SAME

CROSS REFERENCE TO RELATED APPLICATIONS

The present application claims the priority benefit of U.S. Provisional Application No. 60/627,538, filed Nov. 12, 2004, which is expressly incorporated fully herein by reference.

FIELD OF THE INVENTION

The present invention relates to 8H-imidazo[4,5-d]thiazolo[4,5-b]pyridine based tricyclic compounds, to methods of using the compounds in treating inflammatory and immune diseases, and cancer and to pharmaceutical compositions comprising same.

BACKGROUND OF THE INVENTION

Tumor necrosis factor (TNF-α) is a potent cytokine having pro-inflammatory properties that is released by many cell types when stimulated. Studies have shown a relationship between elevated levels of TNF-α and a variety of diseases such as septic shock, hematopoiesis, tumors, and inflammatory disorders of the central nervous system, including HIV encephalitis, cerebral malaria, and meningitis. Additionally, certain neurodegenerative diseases such as Alzheimer's disease, Parkinson's disease, and Creutzfeldt-Jacob disease also are reportedly associated with enhanced TNF-α levels. See, e.g., Arvin et al., "*The Role of Inflammation and Cytokines in Brain Injury,*" Neuroscience and Biobehavioral Reviews, Vol. 20, No. 3 (1996), at pp. 445-452. More recently agents which inhibit the action of TNF-α have demonstrated clinical utility in a variety of diseases such as rheumatoid arthritis, psoriasis, and inflammatory bowel disease. See, e.g. Keating, et al. "*Infliximab: An Updated Review of its use in Crohn's Disease and Rheumatoid Arthritis*" BioDrugs Vol 16, (2002) pp. 111-148, and Hanns-Martin, et al. "*Perspectives for TNF-alpha-targeting Therapies.*" Arthritis Res. Vol 4. Supp 3 (2002) pp. S17-24.

Accordingly, various classes of drugs have been researched and developed to inhibit TNF-α production at both transcriptional and translational levels, e.g., corticosteroids, rolipram (a phosphodiesterase IV inhibitor suppressing TNF-α mRNA synthesis), calphostin, and imidazole-type cytokine suppressing anti-inflammatory drugs (CSAIDs or P-38 inhibitors). These drugs are useful in treating a variety of diseases. See Dinarello, "*Role of Pro-and Anti-Inflammatory Cytokines During Inflammation: Experimental and Clinical Findings,*" Review, Vol. 0393-974X (1997), at pp. 91-103.

Recently, attention has focused on the role of Nuclear factor κB (NF-κB) in the activation pathway that leads to production of TNF-α and other inflammatory cytokines and gene products. Besides TNF-α, NF-κB is involved in the regulation of a variety of genes involved in immune function and inflammation. These include the cytokines IL-1, IL-2, IL-6, IL-2Rα, and GM-GSF, the chemokines IL-8, MCP-1 (CCR2), and RANTES, the adhesion molecules, intercellular adhesion molecule-1 (ICAM-1), vascular cellular adhesion molecule-1 (VCAM-1) and E-selectin, the proteases matrix metalloproteinase-1 (MMP-1), MMP-9 and MMP-13, and the pro-inflammatory enzymes cyclooxygenase-2 (COX-2), iNOS, and cPLA$_2$. Thus, inhibition of NF-κB and/or its activation pathway provides a means for treating various diseases including autoimmune diseases, inflammatory diseases, Alzheimer's disease, atherosclerosis, oncogenesis, and so forth by a variety of modes of action (i.e. cytokine reduction, chemokine reduction, reduction of adhesion molecule expression, decreased expression of certain proteases implicated in inflammatory and immune disease processes, and decreased production of enzymes which produce pro-inflammatory mediators) which have been implicated in a variety of disease progression. See, e.g., Baldwin, "*The NF-κB and IκB Proteins: New Discoveries and Insights,*" Annual Rev. Immunol., Vol. 14 (1996), at pp. 649-81; see also Christman et al., "*Impact of Basic Research on Tomorrow's Medicine, The Role of Nuclear Factor-κB in Pulmonary Diseases,*" Chest, Vol. 117 (2000), at pp. 1482-87, and Roshak, et al., "*Small-molecule Inhibitors of NF-κB for the Treatment of Inflammatory Joint Disease.*" Current Opinion in Pharmacol. Vol. 2 (2002) pp. 316-321.

Additionally attention has focused on inhibition of NF-κB and/or its activation pathway to provide a means for treating cancer. Genes which mediate either tumorigenesis or tumor metastasis are regulated by NF-κB. In addition NF-κB is know to be activated by carcinogens and tumor promotors. See e.g., Karin et al.; "*NF-κB in Cancer: From Innocent Bystander to Major Culprit,*" Nature Rev. Cancer., Vol. 2 (2002) at pp. 301-310; see also Bharti et al.; "*Nuclear factor-kappa B and cancer: its role in prevention and therapy*" in Biochem. Pharmocol. at pp. 883-888.

IκB is a cytoplasmic protein that controls NF-κB activity by retaining NF-κB in the cytoplasm. IκB is phosphorylated by the IκB kinase (IKK), which has two isoforms, IKK-α ("IKK-1") and IKK-β ("IKK-2"). When IKK phosphorylates IκB, NF-κB is rapidly released from the cytoplasm into the cell. Upon release into the cell, NF-κB translocates to the nucleus where it binds to the promoters of many genes and up-regulates the transcription of pro-inflammatory genes. Thus inhibitors of IKK-1 and/or IKK-2 would prevent translocation of NF-kB to the nucleus and prevent transcription of the pro-inflammatory gene products described above. For example see Burke, et al. "*BMS-345541 is a Highly Selective Inhibitor of IkB Kinase that Binds at an Allosteric Site of the Enzyme and Blocks NF-kB dependent Transcription in Mice.*" J. Biol. Chem. Vol. 278, (2003) pp. 1450-1456.

The therapeutic effects of glucocorticoids are mediated in part by their ability to inhibit NF-κB activity by two mechanisms, i.e., up-regulating IκB protein levels and inhibiting NF-κB subunits. The deleterious side effects of glucocorticoids (such as osteoporosis, hyperglycemia, fat redistribution, etc.) have been postulated to result from the interaction of glucocorticoids with the glucocorticoid receptor (GR) or the glucocorticoid response element (GRE). For example see Schacke, et al. "*Mechanisms Involved in the Side Effects of Glucocorticoids*" Pharmacol. and Therapeutics Vol 96 (2002) pp. 23-43. Thus inhibitors of IKK-1 and/or IKK-2 inhibitors should provide much of the therapeutic benefit of glucocorticoids with a greatly improved side effect profile.

As may be appreciated, those in the field of pharmaceutical research continue to seek to develop new compounds and compositions having increased effectiveness, bioavailability, and solubility, having fewer side effects, and/or providing the physician and patient with a choice of treatment options. Particularly in the area of immune response, individuals respond differently depending upon the type of treatment and chemical agent used. Mechanisms of action continue to be studied to aid in understanding the immune response and in developing compounds effective for treating inflammatory and immune-related disorders.

The present invention provides for novel tricyclic compounds useful as inhibitors of IKK.

SUMMARY OF THE INVENTION

Accordingly, the present invention provides novel inhibitors of IKK enzyme activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides for a novel process and intermediates for the preparation of the heterocyclic systems described within this document.

The present invention provides a method for treating disorders selected from rheumatoid arthritis, asthma, inflammatory bowel disease, chronic obstructive pulmonary disease, psoriasis, and cancer, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel compounds for use in therapy.

The present invention provides the use of novel compounds for the manufacture of a medicament for the treatment of inflammatory diseases and cancer.

These and other features of the invention, which will become apparent during the following detailed description, have been achieved by the inventors' discovery that compounds of formula (I):

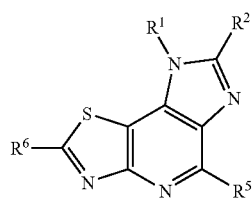

or stereoisomers or pharmaceutically acceptable salts thereof, wherein $R^1$, $R^2$, $R^5$, $R^6$, and X are defined below, are effective modulators of chemokine activity.

DETAILED DESCRIPTION OF EMBODIMENTS OF THE INVENTION

Figure 1:
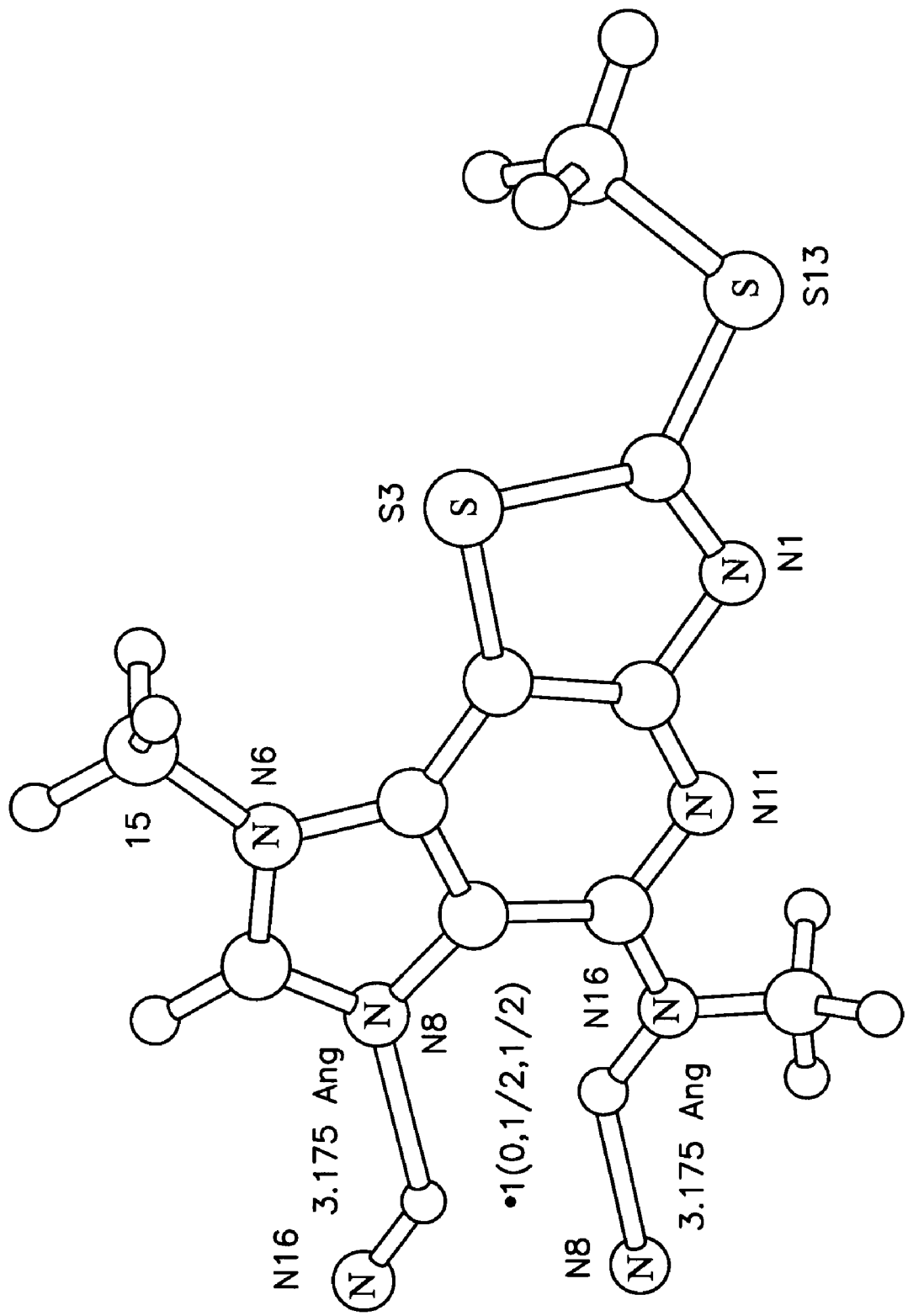
FIG. 1 shows a depiction of structure of compound A1 as determined from x-ray diffraction data. Intermolecular hydrogen bonding is depicted by dashed lines.

The invention is directed to compounds of formula (I), useful in treating inflammatory or immune conditions or cancer:

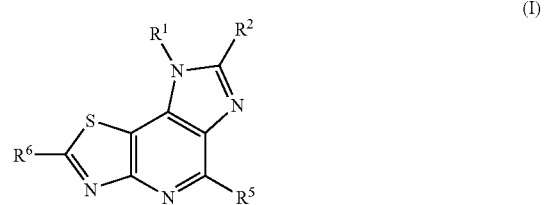

enantiomers, diastereomers, salts, and solvates thereof wherein $R^1$ is selected from hydrogen, $C_{1-3}$ alkyl, $C_{2-3}$ alkenyl, and $C_{2-3}$ alkynyl;

$R^2$ is hydrogen, halo, cyano,
(b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1a}$, $Z^{2a}$ and $Z^{3a}$; or
(c) —$OR^{10a}$, —$SR^{10a}$, or —$SO_2R^{10a}$;

$R^5$ is selected from
a) hydrogen,
(b) alkyl, alkenyl, alkynyl, and haloalkyl, any of which may be optionally independently substituted as valence allows with one or more $Z^{1b}$, $Z^{2b}$ and $Z^{3b}$;
(c) —$OR^{11}$, —$SR^{11}$ and —$NR^3R^4$;

$R^3$ and $R^4$ are independently selected from
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1b}$, $Z^{2b}$ and $Z^{3b}$;
(c) —$OR^{11}$, —$NR^{12}R^{13}$, —$N(R^{12})C(O)R^{14}$, —$N(R^{12})C(O)OR^{14}$, —$N(R^{12})SO_2R^{14}$, —$N(R^{12})C(O)NR^{12a}R^{13}$, or —$N(R^{12})SO_2NR^{12a}R^{13}$ or —$C(O)OR^{14}$, —$C(O)R^{11}$, —$C(O)NR^{12}R^{13}$, —$SO_2R^{14}$, —$SO_2NR^{12}R^{13}$;
(d) $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$;

$R^6$ is
(a) hydrogen, hydroxy, halo, or cyano,
(b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(c) —$OR^{7a}$, —$SR^{7a}$, —$NR^{8a}R^{9a}$, —$N(R^{8a})SO_2R^{10}$, —$N(R^{8a})SO_2NR^{8b}R^{9b}$, —$N(R^{8a})SO_2R^{10}$, —$N(R^{8a})C(O)R^{7a}$, —$N(R^{8a})N(R^{8a})C(O)R^{7a}$, —$N(R^{8a})C(O)NR^{8b}R^{9b}$, —$N(R^{8a})C(O)OR^{7a}$, —$SO_2R^{10}$, —$SO_2NR^{8b}R^{9b}$, —$C(O)R^{7a}$, —$C(O)OR^{7a}$, —$OC(O)R^{7a}$, —$C(O)NR^{8a}R^{9a}$, or —$OC(O)NR^{8a}R^{9a}$;

$R^{7a}$ and $R^{7b}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;

$R^{8a}$, $R^{8b}$, $R^{9a}$ and $R^{9b}$ are independently
  (a) hydrogen,
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$; or $R^{10}$, $R^{10a}$, at each occurrence, are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{11}$, $R^{12}$, $R^{12a}$ and $R^{13}$ are independently
  (a) hydrogen, or
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$Z^{1a-1e}$, $Z^{2a-2e}$, and $Z^{3a-3e}$ are optional substituents at each occurrence independently selected from —$W^1$—$V^1$; —$W^2$—$V^2$; —$W^3$—$V^3$; —$W^4$—$V^4$; —$W^5$—$V^5$;
where $W^{1-5}$ are independently
  (1) a bond
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or
where $V^{1-5}$ are independently
  (1) H
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (3) —$U^1$—O—$Y^5$,
  (4) —$U^1$—S—$Y^5$,
  (5) —$U^1$—C(O)$_t$—H, —$U^1$—C(O)$_t$—$Y^5$ where t is 1 or 2,
  (6) —$U^1$—SO$^3$—H, or —$U^1$—S(O)$_t$$Y^5$,
  (7) —$U^1$-halo,
  (8) —$U^1$-cyano,
  (9) —$U^1$-nitro,
  (10) —$U^1$—N$Y^2Y^3$,
  (11) —$U^1$—N($Y^4$)—C(O)—$Y^1$,
  (12) —$U^1$—N($Y^4$)—C(S)—$Y^1$,
  (13) —$U^1$—N($Y^4$)—C(O)—N$Y^2Y^3$,
  (14) —$U^1$—N($Y^4$)—C(S)—N$Y^2Y^3$,
  (15) —$U^1$—N($Y^4$)—C(O)O—$Y^5$,
  (16) —$U^1$—N($Y^4$)—S(O)$_2$—$Y^1$,
  (17) —$U^1$—N($Y^4$)—S(O)$_2$—N$Y^2Y^3$,
  (18) —$U^1$—C(O)—N$Y^2Y^3$,
  (19) —$U^1$—OC(O)—N$Y^2Y^3$
  (20) —$U^1$—S(O)$_2$—N($Y^4$)—$Y^1$,
  (21) —$U^1$—N($Y^4$)—C(=N$V^{1a}$)—N$Y^2Y^3$,
  (22) —$U^1$—N($Y^4$)—C(=N$V^{1a}$)—$Y^1$,
  (23) —$U^1$—C(=N$V^{1a}$)—N$Y^2Y^3$,
  (24) oxo;
  (25) —$U^1$—$Y^5$;
$V^{1a}$ is independently hydrogen, alkyl, —CN, —C(O)$Y^1$, —S(O)$_2Y^5$, S(O)$_2$N$Y^2Y^3$;

$Y^1$, $Y^2$, $Y^3$, $Y^4$ and $Y^5$
  (1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more $Z^4$, $Z^5$ and $Z^6$; or
  (2) $Y^2$ and $Y^3$ may together be alkylene or alkenylene, completing a 3- to 8-membered saturated or unsaturated ring together with the atoms to which they are attached, or
  (4) $Y^2$ and $Y^3$ together with the nitrogen atom to which they are attached may combine to form a group —N=C$Y^6Y^7$ where $Y^6$ and $Y^7$ are each independently H or alkyl; and $Z^4$, $Z^5$, and $Z^6$ are optional substituents at each occurrence independently selected from
  (1) H
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (3) —$U^1$—O—$Y^{5a}$,
  (4) —$U^1$—S—$Y^{5a}$,
  (5) —$U^1$—C(O)$_t$—H, —$U^1$—C(O)$_t$—$Y^{5a}$ where t is 1 or 2,
  (6) —$U^1$—SO$^3$—H, or —$U^1$—S(O)$_t Y^{5a}$,
  (7) —$U^1$-halo,
  (8) —$U^1$-cyano,
  (9) —$U^1$-nitro,
  (10) —$U^1$—N$Y^{2a}Y^{3a}$,
  (11) —$U^1$—N($Y^{4a}$)—C(O)—$Y^{1a}$,
  (12) —$U^1$—N($Y^{4a}$)—C(S)—$Y^{1a}$,
  (13) —$U^1$—N($Y^{4a}$)—C(O)—N$Y^{2a}Y^{3a}$,
  (14) —$U^1$—N($Y^{4a}$)—C(S)—N$Y^{2a}Y^{3a}$,
  (15) —$U^1$—N($Y^{4a}$)—C(O)O—$Y^{5a}$,
  (16) —$U^1$—N($Y^{4a}$)—S(O)$_2$—$Y^{1a}$,
  (17) —$U^1$—N($Y^{4a}$)—S(O)$_2$—N$Y^{2a}Y^{3a}$,
  (18) —$U^1$—C(O)—N$Y^{2a}Y^{3a}$,
  (19) —$U^1$—OC(O)—N$Y^{2a}Y^{3a}$
  (20) —$U^1$—S(O)$_2$—N($Y^{4a}$)—$Y^{1a}$,
  (21) —$U^1$—N($Y^{4a}$)—C(=N$V^{1a}$)—N$Y^{2a}Y^{3a}$,
  (22) —$U^1$—N($Y^{4a}$)—C(=N$V^{1a}$)—$Y^{1a}$,
  (23) —$U^1$—C(=N$V^{1a}$)—N$Y^{2a}Y^{3a}$,
  (24) oxo;
  (25) —$U^1$—$Y^{5a}$;

$Y^{1a}$, $Y^{2a}$, $Y^{3a}$, $Y^{4a}$ and $Y^{5a}$
  (1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;

$U^1$ is independently
  (1) a single bond,
  (2) alkylene,
  (3) alkenylene, or
  (4) alkynylene.

In another embodiment, the present invention is directed to compounds of formula (I), wherein $R^1$ is selected from hydrogen, $C_{1-3}$ alkyl, $C_{2-3}$ alkenyl, and $C_{2-3}$ alkynyl;

$R^2$ is hydrogen, halo, cyano,
  (b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1a}$, $Z^{2a}$ and $Z^{3a}$; or
  (c) —$OR^{10a}$, —$SR^{10a}$, or —$SO_2R^{10a}$;
$R^5$ is —$NR^3R^4$;
$R^3$ and $R^4$ are independently selected from
  (a) hydrogen,
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1b}$, $Z^{2b}$ and $Z^{3b}$;
  (c) —$OR^{11}$, —$NR^{12}R^{13}$, —$N(R^{12})C(O)R^{14}$, —$N(R^{12})C(O)OR^{14}$, —$N(R^{12})SO_2R^{14}$, —$N(R^{12})C(O)NR^{12a}R^{13}$, or —$N(R^{12})SO_2NR^{12a}R^{13}$ or —$C(O)OR^{14}$, —$C(O)R^{11}$, —$C(O)NR^{12}R^{13}$, —$SO_2R^{14}$, —$SO_2NR^{12}R^{13}$;
  (d) $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$;
$R^6$ is
  (a) hydrogen, hydroxy, halo, or cyano,
  (b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
  (c) —$OR^{7a}$, —$SR^{7a}$, —$NR^{8a}R^{9a}$, —$N(R^{8a})SO_2R^{10}$, —$N(R^{8a})SO_2NR^{8b}R^{9b}$, —$N(R^{8a})SO_2R^{10}$, —$N(R^{8a})C(O)R^{7a}$, —$N(R^{8a})N(R^{8a})C(O)R^{7a}$, —$N(R^{8a})C(O)NR^{8b}R^{9b}$, —$N(R^{8a})C(O)OR^{7a}$, —$SO_2R^{10}$, —$SO_2NR^{8b}R^{9b}$, —$C(O)R^{7a}$, —$C(O)OR^{7a}$, —$OC(O)R^{7a}$, —$C(O)NR^{8a}R^{9a}$, or —$OC(O)NR^{8a}R^{9a}$;
$R^{7a}$ and $R^{7b}$ are independently
  (a) hydrogen, or
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;
$R^{8a}$, $R^{8b}$, $R^{9a}$ and $R^{9b}$ are independently
  (a) hydrogen,
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$; or
$R^{10}$, $R^{10a}$, at each occurrence, are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;
$R^{11}$, $R^{12}$, $R^{12a}$ and $R^{13}$ are independently
  (a) hydrogen, or
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;
$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;
$Z^{1a\text{-}1e}$, $Z^{2a\text{-}2e}$, and $Z^{3a\text{-}3e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1\text{-}5}$ are independently
  (1) a bond
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or
where $V^{1\text{-}5}$ are independently
  (1) H
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (3) —$U^1$—O—$Y^5$,
  (4) —$U^1$—S—$Y^5$,
  (5) —$U^1$—$C(O)_t$—H, —$U^1$—$C(O)_t$—$Y^5$ where t is 1 or 2,
  (6) —$U^1$—$SO^3$—H, or —$U^1$—$S(O)_tY^5$,
  (7) —$U^1$-halo,
  (8) —$U^1$-cyano,
  (9) —$U^1$-nitro,
  (10) —$U^1$—$NY^2Y^3$,
  (11) —$U^1$—$N(Y^4)$—$C(O)$—$Y^1$,
  (12) —$U^1$—$N(Y^4)$—$C(S)$—$Y^1$,
  (13) —$U^1$—$N(Y^4)$—$C(O)$—$NY^2Y^3$,
  (14) —$U^1$—$N(Y^4)$—$C(S)$—$NY^2Y^3$,
  (15) —$U^1$—$N(Y^4)$—$C(O)O$—$Y^5$,
  (16) —$U^1$—$N(Y^4)$—$S(O)_2$—$Y^1$,
  (17) —$U^1$—$N(Y^4)$—$S(O)_2$—$NY^2Y^3$,
  (18) —$U^1$—$C(O)$—$NY^2Y^3$,
  (19) —$U^1$—$OC(O)$—$NY^2Y^3$
  (20) —$U^1$—$S(O)_2$—$N(Y^4)$—$Y^1$,
  (21) —$U^1$—$N(Y^4)$—$C(=NV^{1a})$—$NY^2Y^3$,
  (22) —$U^1$—$N(Y^4)$—$C(=NV^{1a})$—$Y^1$,
  (23) —$U^1$—$C(=NV^{1a})$—$NY^2Y^3$,
  (24) oxo;
  (25) —$U^1$—$Y^5$;
$V^{1a}$ is independently hydrogen, alkyl, —CN, —$C(O)Y^1$, —$S(O)_2Y^5$, $S(O)_2NY^2Y^3$;
$Y^1$, $Y^2$, $Y^3$, $Y^4$ and $Y^5$
  (1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more $Z^4$, $Z^5$ and $Z^6$; or
  (2) $Y^2$ and $Y^3$ may together be alkylene or alkenylene, completing a 3- to 8-membered saturated or unsaturated ring together with the atoms to which they are attached, or
  (4) $Y^2$ and $Y^3$ together with the nitrogen atom to which they are attached may combine to form a group —N=$CY^6Y^7$ where $Y^6$ and $Y^7$ are each independently H or alkyl; and
$Z^4$, $Z^5$, and $Z^6$ are optional substituents at each occurrence independently selected from
  (1) H
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (3) —$U^1$—O—$Y^{5a}$,
  (4) —$U^1$—S—$Y^{5a}$,
  (5) —$U^1$—$C(O)_t$—H, —$U^1$—$C(O)_t$—$Y^{5a}$ where t is 1 or 2,
  (6) —$U^1$—$SO^3$—H, or —$U^1$—$S(O)_tY^{5a}$,
  (7) —$U^1$-halo,
  (8) —$U^1$-cyano, (9) —U$^1$-nitro,
(10) —U$^1$—NY$^{2a}$Y$^{3a}$,
(11) —U$^1$—N(Y$^{4a}$)—C(O)—Y$^{1a}$,
(12) —U$^1$—N(Y$^{4a}$)—C(S)—Y$^{1a}$,
(13) —U$^1$—N(Y$^{4a}$)—C(O)—NY$^{2a}$Y$^{3a}$,
(14) —U$^1$—N(Y$^{4a}$)—C(S)—NY$^{2a}$Y$^{3a}$,
(15) —U$^1$—N(Y$^{4a}$)—C(O)O—Y$^{5a}$,
(16) —U$^1$—N(Y$^{4a}$)—S(O)$_2$—Y$^{1a}$,
(17) —U$^1$—N(Y$^{4a}$)—S(O)$_2$—NY$^{2a}$Y$^{3a}$,
(18) —U$^1$—C(O)—NY$^{2a}$Y$^{3a}$,
(19) —U$^1$—OC(O)—NY$^{2a}$Y$^{3a}$
(20) —U$^1$—S(O)$_2$—N(Y$^{4a}$)—Y$^{1a}$,
(21) —U$^1$—N(Y$^{4a}$)—C(=NV$^{1a}$)—NY$^{2a}$Y$^{3a}$,
(22) —U$^1$—N(Y$^{4a}$)—C(=NV$^{1a}$)—Y$^{1a}$,
(23) —U$^1$—C(=NV$^{1a}$)—NY$^{2a}$Y$^{3a}$,
(24) oxo;
(25) —U$^1$—Y$^{5a}$;

Y$^{1a}$, Y$^{2a}$, Y$^{3a}$, Y$^{4a}$ and Y$^{5a}$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;

U$^1$ is independently
(1) a single bond,
(2) alkylene,
(3) alkenylene, or
(4) alkynylene.

In another embodiment, the present invention is directed to compounds of formula (I), wherein
R$^3$ and R$^4$ are independently
(a) hydrogen,
(b) alkyl, haloalkyl, (hydroxy)alkyl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more Z$^{1b}$, Z$^{2b}$ and Z$^{3b}$;
(c) —NR$^{12}$R$^{13}$; or
(d) R$^3$ and R$^4$ together with the nitrogen atom to which they are attached combine to form a 3 to 8 membered heterocyclic ring optionally independently substituted as valence allows with one or more Z$^{1b}$, Z$^{2b}$ and Z$^{3b}$.

In another embodiment, the present invention is directed to compounds of formula (I), wherein
R$^6$ is
(a) hydrogen, alkyl, alkenyl, alkynyl, aryl, heteroaryl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more Z$^{1d}$, Z$^{2d}$ and Z$^{3d}$; or
(b) —OR$^{7a}$, —SR$^{7a}$, —NR$^{8a}$R$^{9a}$, —N(R$^{8a}$)SO$_2$R$^{10}$, —N(R$^{8a}$)SO$_2$NR$^{8b}$R$^{9b}$, —N(R$^{8a}$)SO$_2$R$^{10}$, —N(R$^{8a}$)C(O)R$^{7a}$, —N(R$^{8a}$)N(R$^{8a}$)C(O)R$^{7a}$, —N(R$^{8a}$)C(O)NR$^{8b}$R$^{9b}$, —N(R$^{8a}$)C(O)OR$^{7a}$, —SO$_2$R$^{10}$, —SO$_2$NR$^{8b}$R$^{9b}$, —C(O)R$^{7a}$, —C(O)OR$^{7a}$, —OC(O)R$^{7a}$, —C(O)NR$^{8a}$R$^{9a}$, or —OC(O)NR$^{8a}$R$^{9a}$.

In another embodiment, the present invention is directed to compounds of formula (I), wherein
R$^{7a}$ is independently selected from
(a) hydrogen, or
(b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1c}$, Z$^{2c}$ and Z$^{3c}$.

In another embodiment, the present invention is directed to compounds of formula (I), wherein
R$^3$ and R$^4$ are independently hydrogen, alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more Z$^{1b}$, Z$^{2b}$ and Z$^{3b}$; —NR$^{12}$R$^{13}$; or
alternatively, R$^3$ and R$^4$ together with the nitrogen atom to which they are attached combine to form a 3 to 6 membered heterocyclic ring selected from piperidinyl, morpholinyl, pyrrolidinyl, piperazinyl, and azetidinyl; optionally independently substituted as valence allows with one or more Z$^{1b}$, Z$^{2b}$ and Z$^{3b}$;
R$^6$ is
(a) hydrogen, alkyl, aryl, heteroaryl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more Z$^{1d}$, Z$^{2d}$ and Z$^{3d}$; or
(b) —OR$^{7a}$, —SR$^{7a}$, —NR$^{8a}$R$^{9a}$, —N(R$^{8a}$)SO$_2$R$^{10}$, —N(R$^{8a}$)SO$_2$R$^{10}$, —N(R$^{8a}$)C(O)R$^{7a}$, —N(R$^{8a}$)N(R$^{8a}$)C(O)R$^{7a}$, —N(R$^{8a}$)C(O)NR$^{8b}$R$^{9b}$, —SO$_2$ R$^{10}$, —C(O)R$^{7a}$, or —C(O)NR$^{8a}$R$^{9a}$.

In another embodiment, the present invention is directed to compounds of formula (I), wherein
R$^1$ is hydrogen, methyl, ethyl, propyl, i-propyl, prop-2-enyl, prop-1-enyl; and
R$^2$ is hydrogen, methyl, trifluoromethyl, and phenyl.

The invention is directed to compounds of formula (I), useful in treating inflammatory or immune conditions or cancer:

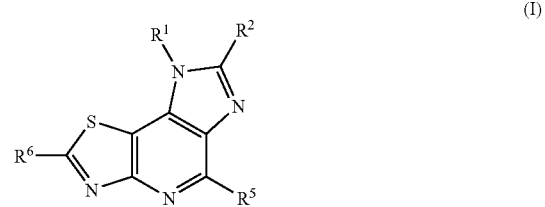

(I)

enantiomers, diastereomers, salts, and solvates thereof wherein
R$^1$ is selected from hydrogen and C$_{1-3}$ alkyl;
R$^2$ is (a) hydrogen, halo, cyano,
(b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1a}$, Z$^{2a}$ and Z$^{3a}$; or
(c) —OR$^{10a}$, —SR$^{10a}$, or —SO$_2$R$^{10a}$;
R$^5$ is selected from
a) hydrogen,
(b) alkyl, alkenyl, alkynyl, and haloalkyl, any of which may be optionally independently substituted as valence allows with one or more Z$^{1b}$, Z$^{2b}$ and Z$^{3b}$;
(c) —OR$^{11}$, —SR$^{11}$ and —NR$^3$R$^4$;
R$^3$ and R$^4$ are independently selected from
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1b}$, Z$^{2b}$ and Z$^{3b}$;

(c) —$OR^{11}$, —$NR^{12}R^{13}$, —$N(R^{12})C(O)R^{14}$, —$N(R^{12})C(O)OR^{14}$, —$N(R^{12})SO_2R^{14}$, —$N(R^{12})C(O)NR^{12a}R^{13}$, or —$N(R^{12})SO_2NR^{12a}R^{13}$ or —$C(O)OR^{14}$, —$C(O)R^{11}$, —$C(O)NR^{12}R^{13}$, —$SO_2R^{14}$, —$SO_2NR^{12}R^{13}$;

(d) $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$;

$R^6$ is
(a) hydrogen, hydroxy, halo, or cyano,
(b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(c) —$OR^{7a}$, —$SR^{7a}$, —$NR^{8a}R^{9a}$, —$N(R^{8a})SO_2R^{10}$, —$N(R^{8a})SO_2NR^{8b}R^{9b}$, —$N(R^{8a})SO_2R^{10}$, —$N(R^{8a})C(O)R^{7a}$, —$N(R^{8a})C(O)NR^{8b}R^{9b}$, —$N(R^{8a})C(O)OR^{7a}$, —$SO_2R^{10}$, —$SO_2NR^{8b}R^{9b}$, —$C(O)R^{7a}$, —$C(O)OR^{7a}$, —$OC(O)R^{7a}$, $C(O)NR^{8a}R^{9a}$, or —$OC(O)NR^{8a}R^{9a}$;

$R^{7a}$ and $R^{7b}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;

$R^{8a}$, $R^{8b}$, $R^{9a}$ and $R^{9b}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$; or $R^{10}$, $R^{10a}$, at each occurrence, are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{11}$, $R^{12}$, $R^{12a}$ and $R^{13}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$Z^{1b-1e}$, $Z^{2b-2e}$, and $Z^{3b-3e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1-5}$ are independently
(1) a bond
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or where $V^{1-5}$ are independently
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

(3) —$U^1$—O—$Y^5$,
(4) —$U^1$—S—$Y^5$,
(5) —$U^1$—$C(O)_t$—H, —$U^1$—$C(O)_t$—$Y^5$ where t is 1 or 2,
(6) —$U^1$—SO3—H, or —$U^1$—$S(O)_tY^5$,
(7) —$U^1$-halo,
(8) —$U^1$-cyano,
(9) —$U^1$-nitro,
(10) —$U^1$—$NY^2Y^3$,
(11) —$U^1$—$N(Y^4)$—C(O)—$Y^1$,
(12) —$U^1$—$N(Y^4)$—C(S)—$Y^1$,
(13) —$U^1$—$N(Y^4)$—C(O)—$NY^2Y^3$,
(14) —$U^1$—$N(Y^4)$—C(S)—$NY^2Y^3$,
(15) —$U^1$—$N(Y^4)$—C(O)O—$Y^5$,
(16) —$U^1$—$N(Y^4)$—$S(O)_2$—$Y^1$,
(17) —$U^1$—$N(Y^4)$—$S(O)_2$—$NY^2Y^3$,
(18) —$U^1$—C(O)—$NY^2Y^3$,
(19) —$U^1$—OC(O)—$NY^2Y^3$
(20) —$U^1$—$S(O)_2$—$N(Y^4)$—$Y^1$,
(21) —$U^1$—$N(Y^4)$—$C(=NV^{1a})$—$NY^2Y^3$,
(22) —$U^1$—$N(Y^4)$—$C(=NV^{1a})$—$Y^1$,
(23) —$U^1$—$C(=NV^{1a})$—$NY^2Y^3$,
(24) oxo;
(25) —$U^1$—$Y^5$;

$V^{1a}$ is independently hydrogen, alkyl, —CN, —$C(O)Y^1$, —$S(O)_2Y^5$, $S(O)_2NY^2Y^3$;

$Y^1$, $Y^2$, $Y^3$, $Y^4$ and $Y^5$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl; or
(2) $Y^2$ and $Y^3$ may together be alkylene or alkenylene, completing a 3- to 8-membered saturated or unsaturated ring together with the atoms to which they are attached, or
(4) $Y^2$ and $Y^3$ together with the nitrogen atom to which they are attached may combine to form a group —$N=CY^6Y^7$ where $Y^6$ and $Y^7$ are each independently H or alkyl; and $U^1$ is independently
(1) a single bond,
(2) alkylene,
(3) alkenylene, or
(4) alkynylene.

In another embodiment, the present invention is directed to compounds of formula (I) wherein $R^1$ is selected from hydrogen and $C_{1-3}$ alkyl;

$R^6$ is
(a) hydrogen, hydroxy, halo, or cyano,
(b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(c) —$OR^{7a}$, —$SR^{7a}$, —$NR^{8a}R^{9a}$, —$N(R^{8a})SO_2R^{10}$, —$N(R^{8a})SO_2NR^{8b}R^{9b}$, —$N(R^{8a})SO_2R^{10}$, —$N(R^{8a})C(O)R^{7a}$, —$N(R^{8a})C(O)NR^{8b}R^{9b}$, —$N(R^{8a})C(O)OR^{7a}$, —$SO_2R^{10}$, —$SO_2NR^{8b}R^{9b}$, —$C(O)R^{7a}$, —$C(O)OR^{7a}$, —$OC(O)R^{7a}$, —$C(O)NR^{8a}R^{9a}$, or —$OC(O)NR^{8a}R^{9a}$;

$Z^{1a-1e}$, $Z^{2a-2e}$, and $Z^{3a-3e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1-5}$ are independently
(1) a bond
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or where $V^{1-5}$ are independently (1) H (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

(3) —$U^1$—O—$Y^5$, (4) —$U^1$—S—$Y^5$, (5) —$U^1$—C(O)$_t$—H, —$U^1$—C(O)$_t$—$Y^5$ where t is 1 or 2, (6) —$U^1$—SO$^3$—H, or —$U^1$—S(O)$_t Y^5$, (7) —$U^1$-halo, (8) —$U^1$-cyano, (9) —$U^1$-nitro,

(10) —$U^1$—NY$^2$Y$^3$,

(11) —$U^1$—N(Y$^4$)—C(O)—Y$^1$,

(12) —$U^1$—N(Y$^4$)—C(S)—Y$^1$,

(13) —$U^1$—N(Y$^4$)—C(O)—NY$^2$Y$^3$,

(14) —$U^1$—N(Y$^4$)—C(S)—NY$^2$Y$^3$,

(15) —$U^1$—N(Y$^4$)—C(O)O—Y$^5$,

(16) —$U^1$—N(Y$^4$)—S(O)$_2$—Y$^1$,

(17) —$U^1$—N(Y$^4$)—S(O)$_2$—NY$^2$Y$^3$,

(18) —$U^1$—C(O)—NY$^2$Y$^3$,

(19) —$U^1$—OC(O)—NY$^2$Y$^3$

(20) —$U^1$—S(O)$_2$—N(Y$^4$)—Y$^1$,

(21) —$U^1$—N(Y$^4$)—C(=NV$^{1a}$)—NY$^2$Y$^3$,

(22) —$U^1$—N(Y$^4$)—C(=NV$^{1a}$)—Y$^1$,

(23) —$U^1$—C(=NV$^{1a}$)—NY$^2$Y$^3$,

(24) oxo;

(25) —$U^1$—Y$^5$;

$V^{1a}$ is independently hydrogen, alkyl, —CN, —C(O)Y$^1$, —S(O)$_2$Y$^5$, S(O)$_2$NY$^2$Y$^3$;

Y$^1$, Y$^2$, Y$^3$, Y$^4$ and Y$^5$ (1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more $Z^4$, $Z^5$ and $Z^6$; or (2) Y$^2$ and Y$^3$ may together be alkylene or alkenylene, completing a 3- to 8-membered saturated or unsaturated ring together with the atoms to which they are attached, or (4) Y$^2$ and Y$^3$ together with the nitrogen atom to which they are attached may combine to form a group —N=CY$^6$Y$^7$ where Y$^6$ and Y$^7$ are each independently H or alkyl.

In another embodiment, the present invention is directed to compounds of formula (I) wherein R$^3$ and R$^4$ are independently (a) hydrogen, (b) alkyl, haloalkyl, (hydroxy)alkyl, cycloalkyl, (cycloalkyl)alkyl, (heterocyclo)alkyl, (aryl)alkyl or (heteroaryl)alkyl any of which may be optionally independently substituted as valence allows with one or more $Z^{1b}$, $Z^{2b}$ and $Z^{3b}$;

(c) —NR$^{12}$R$^{13}$; or (d) R$^3$ and R$^4$ together with the nitrogen atom to which they are attached combine to form a 3 to 8 membered heterocyclic ring optionally independently substituted as valence allows with one or more $Z^{1b}$, $Z^{2b}$ and $Z^{3b}$.

In another embodiment, the present invention is directed to compounds of formula (I) wherein R$^6$ is (a) alkyl, alkenyl, alkynyl, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or (b) —OR$^{7a}$, —SR$^{7a}$, —NR$^{8a}$R$^{9a}$, —N(R$^{8a}$)SO$_2$R$^{10}$, —N(R$^{8a}$)SO$_2$NR$^{8b}$R$^{9b}$, —N(R$^{8a}$)SO$_2$R$^{10}$, —N(R$^{8a}$)C(O)R$^{7a}$, —N(R$^{8a}$)C(O)NR$^{8b}$R$^{9b}$, —N(R$^{8a}$)C(O)OR$^{7a}$, —SO$_2$R$^{10}$, —SO$_2$NR$^{8b}$R$^{9b}$, —C(O)R$^{7a}$, —C(O)OR$^{7a}$, —OC(O)R$^{7a}$, —C(O)NR$^{8a}$R$^{9a}$, or —OC(O)NR$^{8a}$R$^{9a}$.

In another embodiment, the present invention is directed to compounds of formula (I) wherein R$^{7a}$ is independently selected from (a) hydrogen, or (b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$.

In another embodiment, the present invention is directed to compounds of formula (I) wherein $Z^{1b}$, $Z^{2b}$ and $Z^{3b}$ are optional substituents independently selected from alkyl, heteroaryl, —OH, —O—Y$^5$, —U$^1$—NY$^2$Y$^3$, —C(O)$_t$H, —C(O)$_t$Y$^5$;

$Z^{1c}$ is (a) —OH, —OY$^5$ or (b) aryl optionally substituted with —OH or —OY$^5$;

$Z^{1d}$, $Z^{2d}$ and $Z^{3d}$ are optional substituents independently selected from (a) cyano, halo, —OH, —OY$^5$, —U$^1$—NY$^2$Y$^3$, —C(O)$_t$H, —C(O)$_t$Y, —S(O)$_t$Y$^5$;

(b) alkyl or alkoxy optionally substituted with one or more cyano, halo, —OH, —OY, —U$^1$—NY$^2$Y$^3$, —C(O)$_t$H, —C(O)$_t$Y, —S(O)$_t$Y, —U$^1$-heteroaryl.

In another embodiment, the present invention is directed to compounds of formula (I) wherein $Z^{1b}$, $Z^{2b}$ and $Z^{3b}$ are optional substituents independently selected from alkyl, heteroaryl, —OH, —O—Y$^5$, —U$^1$—NY$^2$Y$^3$, —C(O)$_t$H, —C(O)$_t$Y$^5$;

$Z^{1c}$ is (a) —OH, —OY$^5$ or (b) aryl optionally substituted with —OH or —OY$^5$;

$Z^{1d}$, $Z^{2d}$ and $Z^{3d}$ are optional substituents independently selected from (a) cyano, halo, —OH, —OY$^5$, —U$^1$—NY$^2$Y$^3$, —C(O)$_t$H, —C(O)$_t$Y$^5$, —S(O)$_t$Y$^5$;

(b) alkyl or alkoxy optionally substituted with one or more cyano, halo, —OH, —OY$^5$, —U$^1$—NY$^2$Y$^3$, —N(Y$^4$)—C(O)—Y$^1$, —N(Y$^4$)—C(O)—NY$^2$Y$^3$, —C(O)—NY$^2$Y$^3$, —C(O)$_t$H, —C(O)$_t$Y$^5$, —S(O)$_t$Y$^5$, —U$^1$-heteroaryl.

In another embodiment, the present invention is directed to compounds of formula (I) wherein R$^3$ is hydrogen;

R$^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1b}$, $Z^{2b}$ and $Z^{3b}$;

alternatively, R$^3$ and R$^4$ together with the nitrogen atom to which they are attached combine to form a 3 to 6 membered heterocyclic ring selected from piperidinyl, morpholinyl, pyrrolidinyl, and azetidinyl; optionally independently substituted as valence allows with one or more $Z^{1b}$, $Z^{2b}$ and $Z^{3b}$;

$R^6$ is
- (a) alkynyl optionally substituted with $Z^{1d}$ where $Z^{1d}$ is aryl which may be further optionally independently substituted with one or more cyano, halo, —OH, —OY, —$U^1$—$NY^2Y^3$, —C(O)$_t$H, —C(O)$_t$Y, or, —S(O)$_t$Y;
- (b) aryl optionally independently substituted as valence allows with one or more $Z^{1d}$, $Z^{2d}$ and $Z^{3d}$; or
- (c) —$OR^{7a}$, —$SR^{7a}$, —$SO_2R^{10}$, —$SO_2NR^{8b}R^{9b}$, —OC(O)$R^{7a}$, or —OC(O)$NR^{8a}R^{9a}$; $Z^{1b}$, $Z^{2b}$ and $Z^{3b}$ are optional substituents independently selected from —OH, —OY, —$U^1$—$NY^2Y^3$, —C(O)$_t$H, —C(O)$_t$Y, —$U^1$—$N(Y^4)$—C(O)—$Y^1$, or —$U^1$—$N(Y^4)$—C(O)O—$Y^5$,
  where
    $U^1$ is a bond or alkylene;

$Z^{1c}$ is
- (a) —OY where Y is aryl, or
- (b) aryl optionally substituted with —OH or —OY where Y is alkyl;

$Z^{1d}$, $Z^{2d}$ and $Z^{3d}$ are optional substituents independently selected from
- (a) cyano, halo, —OH, —OY, —C(O)$_t$H, —C(O)$_t$Y, —S(O)$_t$Y, or
- (b) alkyl or alkoxy optionally substituted with one or more cyano, halo, —OH, —OY, —$U^1$—$NY^2Y^3$, —C(O)$_t$H, —C(O)$_t$Y, —S(O)$_t$Y, —$U^1$—$N(Y^4)$—C(O)—$Y^1$, —$U^1$—$N(Y^4)$—C(O)—$Y^1$, or —$U^1$—$N(Y^4)$—S(O)$_2$—$Y^1$,
  where
    $U^1$ is a bond or alkylene.

In another embodiment, the present invention is directed to compounds of formula (I) wherein
$R^3$ is hydrogen;
$R^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1b}$, $Z^{2b}$ and $Z^{3b}$;
alternatively, $R^3$ and $R^4$ together with the nitrogen atom to which they are attached combine to form a 3 to 6 membered heterocyclic ring selected from piperidinyl, morpholinyl, pyrrolidinyl, and azetidinyl; optionally independently substituted as valence allows with one or more $Z^{1b}$, $Z^{2b}$ and $Z^{3b}$;

$R^6$ is
- (a) alkynyl optionally substituted with $Z^{1d}$ where $Z^{1d}$ is aryl which may be further optionally independently substituted with one or more cyano, halo, —OH, —OY, —$U^1$—$NY^2Y^3$, —C(O)$_t$H, —C(O)$_t$Y, or, —S(O)$_t$Y;
- (b) aryl optionally independently substituted as valence allows with one or more $Z^{1d}$, $Z^{2d}$ and $Z^{3d}$; or
- (c) —$OR^{7a}$, $SR^{7a}$, —$SO_2R^{10}$, —$SO_2NR^{8b}R^{9b}$, —OC(O)$R^{7a}$, or —OC(O)$NR^{8a}R^{9a}$; $Z^{1b}$, $Z^{2b}$ and $Z^{3b}$ are optional substituents independently selected from —OH, —OY, —$U^1$—$NY^2Y^3$, —C(O)$_t$H, —C(O)$_t$Y, —$U^1$—$N(Y^4)$—C(O)—$Y^1$, or —$U^1$—$N(Y^4)$—C(O)O—$Y^5$,
  where
    $U^1$ is a bond or alkylene;

$Z^{1c}$ is
- (a) —OY where Y is aryl, or
- (b) aryl optionally substituted with —OH or —OY where Y is alkyl;

$Z^{1d}$, $Z^{2d}$ and $Z^{1d}$ are optional substituents independently selected from
- (a) cyano, halo, —OH, —$OY^5$, —C(O)$_t$H, —C(O)$_t Y^5$, —S(O)$_t Y^5$, or
- (b) alkyl or alkoxy optionally substituted with one or more cyano, halo, —OH, —$OY^5$, —$U^1$—$NY^2Y^3$, —$N(Y^4)$—C(O)—$NY^2Y^3$, —C(O)—$NY^2Y^3$, —C(O)$_t$H, —C(O)$_t Y^5$, —S(O)$_t Y^5$, or —$U^1$—$N(Y^4)$—C(O)—$Y^1$,
  where
    $U^1$ is a bond or alkylene.

In another embodiment, the present invention is directed to compounds of formula (I) wherein
$R^1$ is alkyl; and
$R^2$ is hydrogen In another embodiment, the present invention is directed to compounds of formula (I) wherein the compounds are selected from the compounds of Table A2, A3 and of the Examples.

The invention also relates to pharmaceutical compositions containing at least one compound of formula (I) and a pharmaceutically-acceptable carrier or diluent, for use in treating inflammatory and immune diseases or cancer. Also included within the invention are methods of treating such diseases comprising administering to a mammal in need of such treatment an effective amount of at least one compound of formula (I).

In another embodiment, the present invention is directed to compounds of formula (I) wherein
$R^5$ is —$NR^3R^4$; and
$R^6$ is phenyl substituted as valence allows with one or more $Z^{1d}$, $Z^{2d}$ and $Z^{3d}$; —$OR^{7a}$; or $SR^{7a}$.

In another embodiment, $R^6$ is phenyl substituted with 0-3 $Z^{1d}$, $Z^{2d}$ and $Z^{3d}$.

In another embodiment, $R^6$ is —$OR^{7a}$, —$SR^{7a}$, —$NR^{8a}R^{9a}$, —$N(R^{8a})SO_2R^{10}$, —$N(R^{8a})SO_2NR^{8b}R^{9b}$, —$N(R^{8a})SO_2R^{10}$, —$N(R^{8a})C(O)R^{7a}$, —$N(R^{8a})C(O)NR^{8b}R^{9b}$, —$N(R^{8a})C(O)OR^{7a}$, —$SO_2R^{10}$, —$SO_2NR^{8b}R^{9b}$, —C(O)$R^{7a}$, —C(O)$OR^{7a}$, —OC(O)$R^{7a}$, —C(O)$NR^{8a}R^{9a}$, or —OC(O)$NR^{8a}R^{9a}$.

In another embodiment, $R^6$ is —$OR^{7a}$ or —$SR^{7a}$.

In another embodiment, $R^1$ is hydrogen, methyl, or ethyl.
In another embodiment, $R^2$ is hydrogen.

In another embodiment, $R^1$ is selected from hydrogen, $C_{1-3}$ alkyl, and $C_{2-3}$ alkenyl; and $R^2$ is hydrogen, alkyl, haloalkyl, or aryl.

In another embodiment, $R^3$ and $R^4$ are independently selected from
- (a) hydrogen,
- (b) alkyl, haloalkyl, (hydroxy)alkyl, cycloalkyl, (cycloalkyl)alkyl, (heterocyclo)alkyl, (aryl)alkyl or (heteroaryl)alkyl any of which may be optionally independently substituted as valence allows with one or more $Z^{1b}$, $Z^{2b}$ and $Z^{3b}$;
- (c) —$NR^{12}R^{13}$; or
- (d) $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$.

In another embodiment, $R^3$ and $R^4$ are independently selected from
- (a) alkyl which may be optionally independently substituted as valence allows with one or more $Z^{1b}$, $Z^{2b}$ and $Z^{3b}$; or
- (b) —C(O)$OR^{14}$, —C(O)$R^{11}$, —C(O)$NR^{12}R^{13}$, —$SO_2R^{14}$, —$SO_2NR^{12}R^{13}$.

In another embodiment, $R^3$ and $R^4$ are independently selected from
- (a) alkyl which may be optionally independently substituted as valence allows with one or more $Z^{1b}$, $Z^{2b}$ and $Z^{3b}$; or wherein $Z^{1b}$, $Z^{2b}$ and $Z^{3b}$ is H, heterocyclo, heteroaryl, any of which may be optionally independently substituted as valence allows with one or more $Z^4$, $Z^5$ and $Z^6$; or —$U^1$—$NY^2Y^3$, (b) —C(O)OR$^{14}$, —C(O)R$^{11}$, —C(O)NR$^{12}$R$^{13}$, —SO$_2$R$^{14}$, —SO$_2$NR$^{12}$R$^{13}$.

In another embodiment, $R^3$ and $R^4$ are independently selected from hydrogen, alkyl, (hydroxy)alkyl, or (heteroaryl)alkyl any of which may be optionally independently substituted as valence allows with 1-2 $Z^{1b}$, $Z^{2b}$ and $Z^{3b}$; —NR$^{12}$R$^{13}$; or $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$;

$Z^{1b}$, $Z^{2b}$ and $Z^{3b}$ are selected from hydrogen, alkyl, —$U^1$—O—Y$^5$, —$U^1$, —NY$^2$Y$^3$, and $U^1$ is a single bond or alkylene, In another embodiment $R^5$ is selected from —NR$^3$R$^4$.

In another embodiment, $R^5$ is selected from a) hydrogen, or (b) alkyl, alkenyl, alkynyl, and haloalkyl, any of which may be optionally independently substituted as valence allows with one or more $Z^{1b}$, $Z^{2b}$ and $Z^{3b}$;

$R^6$ is

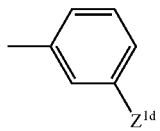

which may be further substituted with with one or more $Z^{1d}$, $Z^{2d}$ and $Z^{3d}$.

In another embodiment, $Y^5$ is H or alkyl, wherein the alkyl is selected from methyl, ethyl, propyl, i-propyl, butyl, i-butyl, t-butyl, pentyl, and hexyl;

$Y^2$ and $Y^3$ are independently selected from alkyl wherein the alkyl is selected from methyl, ethyl, propyl, i-propyl, butyl, i-butyl, t-butyl, pentyl, and hexyl.

In another embodiment, $R^3$ and $R^4$ are independently selected from hydrogen, alkyl, wherein the alkyl is selected from methyl, ethyl, propyl, i-propyl, butyl, i-butyl, t-butyl, pentyl, and hexyl; (hydroxy)alkyl, or (heteroaryl)alkyl, wherein (heteroaryl)alkyl is (tetrazolyl)methyl; any of which may be optionally independently substituted with 1 $Z^{1b}$; —NR$^{12}$R$^{13}$; or $R^3$ and $R^4$ together with the nitrogen atom to which they are attached combine to form a 3 to 8 membered heterocyclic ring, wherein the ring is selected from piperidinyl, and morpholinyl, optionally independently substituted with 1 $Z^{1b}$.

In another embodiment, $R^3$ is hydrogen;

$R^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1b}$, $Z^{2b}$ and $Z^{3b}$;

alternatively, $R^3$ and $R^4$ together with the nitrogen atom to which they are attached combine to form a 3 to 6 membered heterocyclic ring selected from piperidinyl, morpholinyl, pyrrolidinyl, and azetidinyl; optionally independently substituted as valence allows with one or more $Z^{1b}$, $Z^{2b}$ and $Z^{3b}$.

In another embodiment, $R^6$ is (a) alkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or (b) —OR$^{7a}$, —SR$^{7a}$, —NR$^{8a}$R$^{9a}$, —N(R$^{8a}$)C(O)R$^{7a}$, —N(R$^{8a}$)N(R$^{8a}$)C(O)R$^{7a}$, —N(R$^{8a}$)C(O)NR$^{8b}$R$^{9b}$, —N(R$^{8a}$)C(O)OR$^{7a}$, —SO$_2$ R$^{10}$, —SO$_2$NR$^{8b}$R$^{9b}$, —C(O)R$^{7a}$, —C(O)OR$^{7a}$, —OC(O)R$^{7a}$, —C(O)NR$^{8a}$R$^{9a}$, or —OC(O)NR$^{8a}$R$^{9a}$.

In another embodiment, $R^6$ is (a) alkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or (b) —OR$^{7a}$, —SR$^{7a}$, —NR$^{8a}$R$^{9a}$, —N(R$^{8a}$)C(O)R$^{7a}$, —N(R$^{8a}$)N(R$^{8a}$)C(O)R$^{7a}$, —N(R$^{8a}$)C(O)NR$^{8b}$R$^{9b}$, —N(R$^{8a}$)C(O)OR$^{7a}$, —SO$_2$ R$^{10}$, —SO$_2$NR$^{8b}$R$^{9b}$, —C(O)R$^{7a}$, —C(O)OR$^{7a}$, —OC(O)R$^{7a}$, —C(O)NR$^{8a}$R$^{9a}$, or —OC(O)NR$^{8a}$R$^{9a}$;

wherein $Z^{1d}$, $Z^{2d}$ and $Z^{3d}$ is —W$^4$—V$^4$; where W$^4$ is (1) a bond (2) alkyl, (hydroxy)alkyl, alkenyl, haloalkyl, heteroaryl, or (heteroaryl)alkyl; and where V$^4$ is (1) H (2) aryl, (aryl)alkyl, heterocyclo, (heterocyclo)alkyl, heteroaryl, or (heteroaryl)alkyl;

(3) —U$^1$—O—Y$^5$, (4) —U$^1$—C(O)$_t$—H, —U$^1$—C(O)$_t$—Y$^5$ where t is 1 or 2, (5) —U$^1$—SO$^3$—H, or —U$^1$—S(O)$_t$Y$^5$, (6) —U$^1$-halo, (7) —U$^1$—NY$^2$Y$^3$, (8) —U$^1$—N(Y$^4$)—C(O)—Y$^1$, (8) —U$^1$—N(Y$^4$)—C(O)—NY$^2$Y$^3$,

(10) —U$^1$—N(Y$^4$)—C(O)O—Y$^5$,

(11) —U$^1$—N(Y$^4$)—S(O)$_2$—Y$^1$,

(12) —U$^1$—N(Y$^4$)—S(O)$_2$—NY$^2$Y$^3$,

(13) —U$^1$—C(O)—NY$^2$Y$^3$,

(14) —U$^1$—OC(O)—NY$^2$Y$^3$

(15) —U$^1$—S(O)$_2$—N(Y$^4$)—Y$^1$; and $U^1$ is a bond.

In another embodiment, the present invention is directed to compounds of formula (I) wherein $R^6$ is

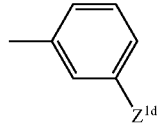

which may be further substituted with with one or more $Z^{1d}$, $Z^{2d}$ and $Z^{3d}$.

In another embodiment, $R^6$ is (a) alkynyl optionally substituted with $Z^{1d}$ where $Z^{1d}$ is aryl which may be further optionally independently substituted with one or more cyano, halo, —OH, —OY, —U$^1$—NY$^2$Y$^3$, —C(O)$_t$H, —C(O)$_t$Y, or, —S(O)$_t$Y;

(b) aryl optionally independently substituted as valence allows with one or more $Z^{1d}$, $Z^{2d}$ and $Z^{3d}$; or (c) —OR$^{7a}$, —SR$^{7a}$, —SO$_2$ R$^{10}$, —SO$_2$NR$^{8b}$R$^{9b}$, —OC(O)R$^{7a}$, or —OC(O)NR$^{8a}$R$^{9a}$;

$Z^{1b}$, $Z^{2b}$ and $Z^{3b}$ are optional substituents independently selected from —OH, —OY, —$U^1$—$NY^2Y^3$, —$C(O)_tH$, —$C(O)_tY$, —$U^1$—$N(Y^4)$—$C(O)$—$Y^1$, or —$U^1$—$N(Y^4)$—$C(O)O$—$Y^5$.

In another embodiment
$R^6$ is
(a) alkynyl optionally substituted with $Z^{1d}$ where $Z^{1d}$ is aryl which may be further optionally independently substituted with one or more cyano, halo, —OH, —OY, —$U^1$—$NY^2Y^3$, —$C(O)_tH$, —$C(O)_tY$, or, —$S(O)_tY$;
(b) aryl optionally independently substituted as valence allows with one or more $Z^{1d}$, $Z^{2d}$ and $Z^{3d}$; or
(c) —$OR^{7a}$, $SR^{7a}$, —$SO_2R^{10}$, —$SO_2NR^{8b}R^{9b}$, —$OC(O)R^{7a}$, or —$OC(O)NR^{8a}R^{9a}$;
$Z^{1b}$, $Z^{2b}$ and $Z^{3b}$ are optional substituents independently selected from —OH, —OY, —$U^1$—$NY^2Y^3$, —$C(O)_tH$, —$C(O)_tY$, —$U^1$—$N(Y^4)$—$C(O)$—$Y^1$, or —$U^1$—$N(Y^4)$—$C(O)O$—$Y^5$,
where
$U^1$ is a bond or alkylene;
$Z^{1c}$ is
  (a) —OY where Y is aryl, or
  (b) aryl optionally substituted with —OH or —OY where Y is alkyl;
$Z^{1d}$, $Z^{2d}$ and $Z^{3d}$ are optional substituents independently selected from
  (a) cyano, halo, —OH, —OY, —$C(O)_tH$, —$C(O)_tY$, —$S(O)_tY$, or
  (b) alkyl or alkoxy optionally substituted with one or more cyano, halo, —OH, —OY, —$U^1$—$NY^2Y^3$, —$C(O)_tH$, —$C(O)_tY$, —$S(O)_tY$, —$U^1$—$N(Y^4)$—$C(O)$—$Y^1$, —$U^1$—$N(Y^4)$—$C(O)$—$Y^1$, or —$U^1$—$N(Y^4)$—$S(O)_2$—$Y^1$,
  where
$U^1$ is a bond or alkylene.

In another embodiment
$R^6$ is
(a) alkynyl optionally substituted with $Z^{1d}$ where $Z^{1d}$ is phenyl which may be further optionally independently substituted with 0-1 cyano, halo, —OH, —OY, —$U^1$—$NY^2Y^3$, —$C(O)_tH$, —$C(O)_tY$, or, —$S(O)_tY$;
(b) phenyl optionally independently substituted as valence allows with one or more $Z^{1d}$, $Z^{2d}$ and $Z^{3d}$; or
(c) —$OR^{7a}$, —$SR^{7a}$;
$Z^{1b}$, $Z^{2b}$ and $Z^{3b}$ are optional substituents independently selected from —OH, —OY, —$U^1$—$NY^2Y^3$, —$C(O)_tH$, —$C(O)_tY$, —$U^1$—$N(Y^4)$—$C(O)$—$Y^1$, or —$U^1$—$N(Y^4)$—$C(O)O$—$Y^5$,
where
$U^1$ is a bond or alkylene, wherein alkylene is selected from methylene, ethylene, propylene, and butylene;
$Z^{1c}$ is
  (a) —OY where Y is phenyl, or
  (b) phenyl optionally substituted with 0-1 —OH or —OY where Y is alkyl selected from methyl, ethyl, propyl, i-propyl, butyl, i-butyl, t-butyl, pentyl, hexyl;
$Z^{1d}$, $Z^{2d}$ and $Z^{3d}$ are optional substituents independently selected from
  (a) cyano, halo, —OH, —OY, —$C(O)_tH$, —$C(O)_tY$, —$S(O)_tY$, or
  (b) alkyl or alkoxy optionally substituted with one or more cyano, halo, —OH, —OY, —$U^1$—$NY^2Y^3$, —$C(O)_tH$, —$C(O)_tY$, —$S(O)_tY$, —$U^1$—$N(Y^4)$—$C(O)$—$Y^1$, —$U^1$—$N(Y^4)$—$C(O)$—$Y^1$, or —$U^1$—$N(Y^4)$—$S(O)_2$—$Y^1$, where
$U^1$ is a bond or alkylene, wherein alkylene is selected from methylene, ethylene, propylene, and butylene.

In another embodiment, $Y^1$, $Y^2$, $Y^3$, and $Y^4$ are independently selected from hydrogen, alkyl, wherein alkyl is selected from alkyl is selected from methyl, ethyl, propyl, i-propyl, butyl, i-butyl, t-butyl, pentyl, and hexyl; aryl wherein aryl is phenyl, (aryl)alkyl.

In another embodiment, the present invention is directed to a compound of Formula (I), wherein the compound is selected from the compounds of the Examples or of Tables.

In another embodiment, the present invention is directed to a pharmaceutical composition, comprising a pharmaceutically acceptable carrier and a therapeutically effective amount of a compound of Formula (I).

In another embodiment, the present invention is directed to a method of treating an inflammatory or immune disease or disorder comprising administering to a mammal in need thereof a therapeutically-effective amount of at least one compound of formula (I).

In another embodiment, the present invention is directed to a method of treating cancer comprising administering to a mammal in need thereof a therapeutically-effective amount of at least one compound of formula (I)

In another embodiment, the present invention is directed to a method of treating an inflammatory or immune disease or disorder selected from, rheumatoid arthritis, asthma, inflammatory bowel disease, chronic obstructive pulmonary disease, and psoriasis.

In another embodiment, the present invention is directed the use of a compound of Formula (I) in the preparation of a medicament for the treatment of an inflammatory or immune disease.

In another embodiment, the present invention is directed the use of a compound of Formula (I) in the preparation of a medicament for the treatment of cancer.

In another embodiment, the present invention is directed to the use of a compound of Formula (I) in the preparation of a medicament for the treatment of an inflammatory or immune disease.

In another embodiment, the present invention is directed to the use of a compound of Formula (I) in the preparation of a medicament for the treatment of cancer.

In another embodiment, the present invention is directed to the use of a compound of Formula (I) in the preparation of a medicament for the treatment of an inflammatory or immune disease, wherein the disease is selected from, rheumatoid arthritis, asthma, inflammatory bowel disease, chronic obstructive pulmonary disease, and psoriasis.

In another embodiment, the present invention is directed to the use of a compound of Formula (I) for use in therapy.

The invention may be embodied in other specific forms without departing from the spirit or essential attributes thereof. This invention also encompasses all combinations of alternative aspects and embodiments of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

The following are definitions of terms used in this specification. The initial definition provided for a group or term herein applies to that group or term throughout the present specification, individually or as part of another group, unless otherwise indicated.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substitent is keto (i.e., =O), then 2 hydrogens on the atom are replaced. The term "optionally independently substituted as valence allows", as used herein, means that the any one or more hydrogens on the designated variable is independently replaced with a selection from the indicated group, provided that the designated variable's normal valency is not exceeded, and that the substitution results in a stable compound.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The term "alkyl" as used herein by itself or as part of another group refers to straight and branched chain hydrocarbons, containing 1 to 20 carbons, alternatively, 1 to 10 carbons, or 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Lower alkyl groups, that is, alkyl groups of 1 to 4 carbon atoms, are an alternative embodiment.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $—C_vF^w$ where v=1 to 3 and w=1 to (2v+1)).

The term "alkenyl" as used herein by itself or as part of another group refers to straight or branched chain radicals of 2 to 20 carbons, alternatively, 2 to 12 carbons, or 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkynyl" as used herein by itself or as part of another group refers to straight or branched chain hydrocarbon groups having 2 to 12 carbon atoms, alternatively, 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like.

When the term "alkyl" is used together with another group, such as in "(aryl)alkyl", this conjunction is meant to refer to a substituted alkyl group wherein at least one of the substituents is the specifically named group in the conjunction. For example, "(aryl)alkyl" refers to a substituted alkyl group as defined above wherein at least one of the substituents is an aryl, such as benzyl.

Where alkyl groups as defined above have single bonds for attachment to two other groups, they are termed "alkylene" groups. Similarly, where alkenyl groups as defined above and alkynyl groups as defined above, respectively, have single bonds for attachment to two other groups, they are termed "alkenylene groups" and "alkynylene groups" respectively. Examples of alkylene, alkenylene and alkynylene groups include:

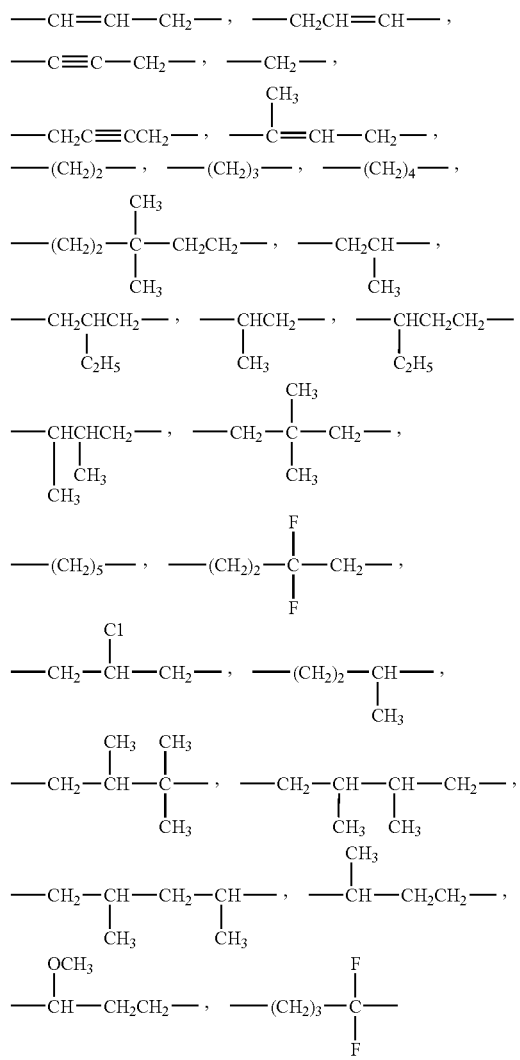

and the like. Alkylene groups may be optionally independently substituted as valence allows with one or more groups provided in the definition of $Z^1$.

The term "cycloalkyl" as used herein by itself or as part of another group refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, alternatively, 3 to 7 carbons, forming the ring. The rings of multi-ring cycloalkyls may be either fused, bridged and/or joined through one or more spiro union to 1 or 2 aromatic, cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

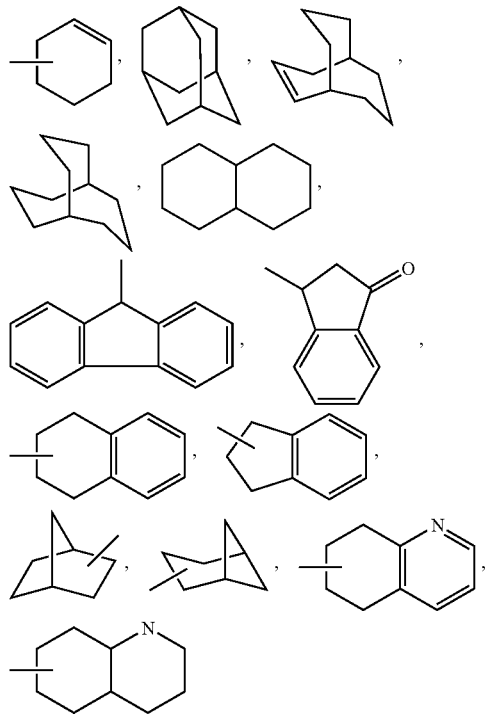

and the like.

The term "cycloalkylene" as employed herein refers to a "cycloalkyl" group which includes free bonds and thus is a linking group such as

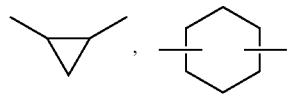

and the like.

One skilled in the field will understand that, when the designation "CO²" is used herein, this is intended to refer to the group

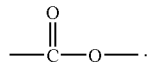

The term "alkoxy" refers to an alkyl or substituted alkyl group as defined above bonded through an oxygen atom (—O—), i.e., the groups —$OR^d$, wherein $R^d$ is alkyl or substituted alkyl.

The term "alkylthio" refers to an alkyl or substituted alkyl group as defined above bonded through a sulfur atom (—S—), i.e., the groups —$SR^d$, wherein $R^d$ is alkyl or substituted alkyl.

The term "acyl" refers to a carbonyl group linked to an organic radical, more particularly, the group C(=O)$R^g$, wherein $R^g$ can be selected from alkyl, alkenyl, substituted alkyl, or substituted alkenyl, as defined herein.

The term "alkoxycarbonyl" refers to a carboxy group

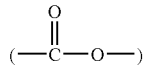

linked to an organic radical ($CO^2R^g$), wherein $R^g$ is as defined above for acyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF^3$.

The terms "ar" or "aryl" as used herein by itself or as part of another group refer to aromatic homocyclic (i.e., hydrocarbon) monocyclic, bicyclic or tricyclic aromatic groups containing 6 to 14 carbons in the ring portion (such as phenyl, biphenyl, naphthyl (including 1-naphthyl and 2-naphthyl) and antracenyl) and may optionally include one to three additional rings (either cycloalkyl, heterocyclo or heteroaryl) fused thereto. Examples include:

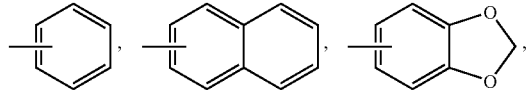

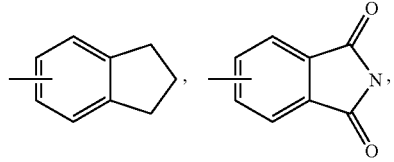

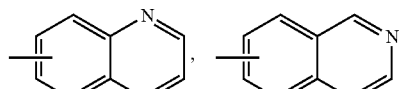

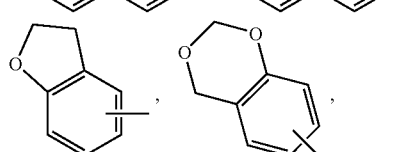

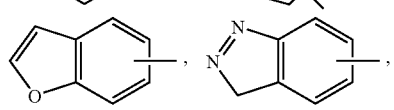

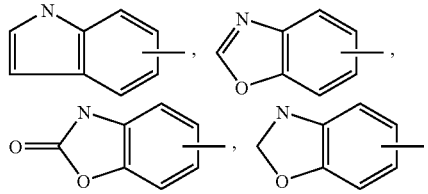

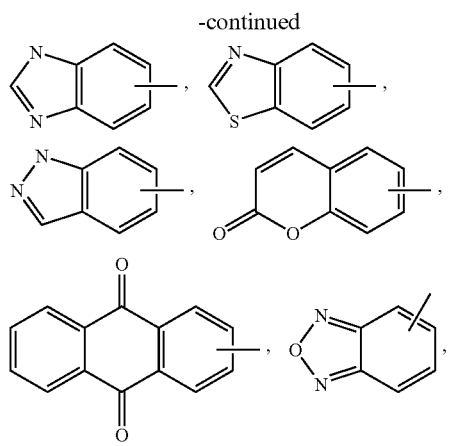

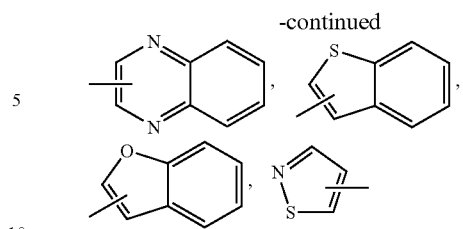

and the like.

In compounds of formula (I), heteroaryl groups include

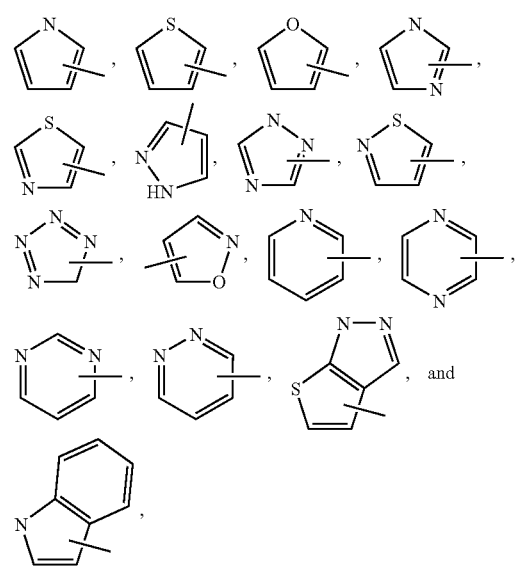

and the like.

The term "heteroaryl" as used herein by itself or as part of another group refers to monocyclic and bicyclic aromatic rings containing from 5 to 10 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaternized. Examples of heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, carbazolyl, benzidolyl, phenanthrollinyl, acridinyl, phenanthridinyl, xanthenyl

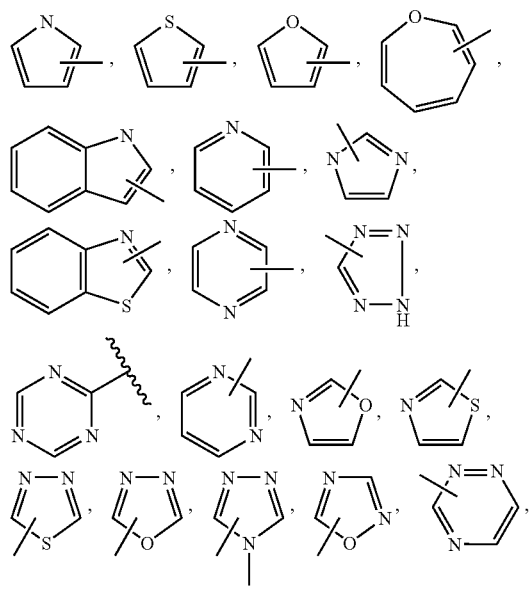

and the like, which optionally may be substituted at any available carbon or nitrogen atom.

The terms "heterocyclic" or "heterocyclo" as used herein by itself or as part of another group refer to optionally substituted, fully saturated or partially unsaturated cyclic groups (for example, 3 to 13 member monocyclic, 7 to 17 member bicyclic, or 10 to 20 member tricyclic ring systems, alternatively, containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be either fused, bridged and/or joined through one or more spiro unions. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

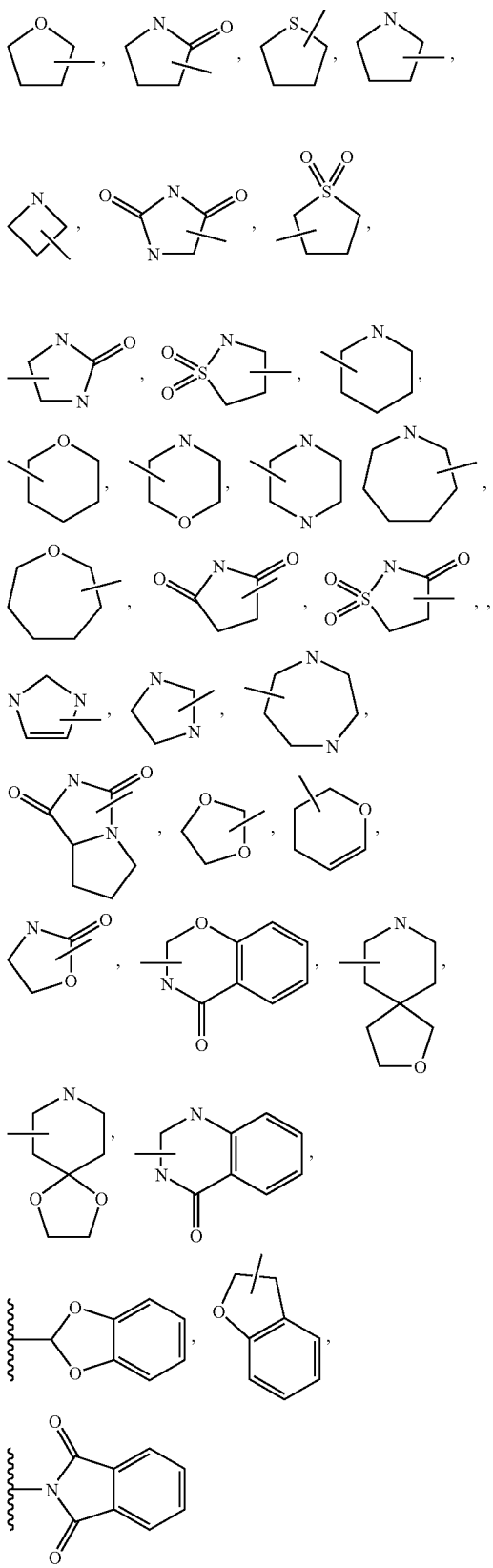

and the like.

Heterocyclo groups in compounds of formula (I) include

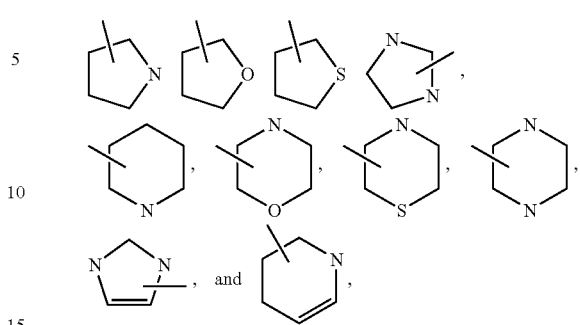

which optionally may be substituted.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated (such as heteroaryl).

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, alternatively, 0 to 2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the formula I, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

In addition, compounds of formula I may have prodrug forms. Any compound that will be converted in vivo to provide the bioactive agent (i.e., a compound of formula I) is a prodrug within the scope and spirit of the invention.

For example, pro-drug compounds of formula I may be carboxylate ester moieties. A carboxylate ester may be conveniently formed by esterifying any of the carboxylic acid functionalities found on the disclosed ring structure(s). Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991), c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull*, Vol. 32, p. 692 (1984).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit IKK or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Methods of Preparation

Compounds of Formula I may be prepared by reference to the methods illustrated in the following Schemes I through IV. As shown therein the end product is a compound having the same structural formula as Formula I. It will be understood that any compound of Formula I may be produced by Schemse I-IV by the suitable selection of reagents with appropriate substitution. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art. Constituents of compounds are as defined herein or elsewhere in the specification.

The sequence described in Scheme I with produce compounds of Formula I. Nitration of 4-hydroxy pyridine, I-1 to provide the known compound I-2. followed by conversion to the corresponding known chloro-pyridine I-3. Subsequent addition of an amine such as methylamine provides the previously un-described compound I-4. Reduction of both nitro groups and simultaneous chlorination of the intermediate triaminopyridine occurs on treatment of I-4 with tin(II) chloride to produce I-5. This important intermediate can be reacted with triethyl orthoformate to provide fused imidazole I-6. Diazotization of the amine under reductive conditions provides imidazopyridine I-7 which reacts with amines such as methyl amine, ethyl amine, para-methoxybenzyl amine etc. in high regioselectivity which after protection with Boc anhydride or similar reagent provides amino compound I-8. Carbonylation of I-8 with carbon monoxide in the presence of a catalyst such as palladium acetate, proceeds to produce carboxylic acid I-9. The carboxylic acid I-9 is subjected to Curtius rearrangement in the presence of trimethylsilylethanol to provide I-10, which on deprotection with tetrabutyl ammonium fluoride produces amine I-11. Chlorination of I-11 with N-chlorosuccinimide produces chloroimidazopyridine I-12. I-12 can be cyclized to compounds of Formula I by reaction with reagents such as potassium ethyl xanthate, which on heating cyclize to thiol I-13, which can be alkylated with reagents such as methyl iodide to produce I-14. Removal of the Boc protecting group can be accomplished under acidic conditions, such as treatment with trifluoroacetic acid to produce compound I-15 which is also a compound of Formula I.

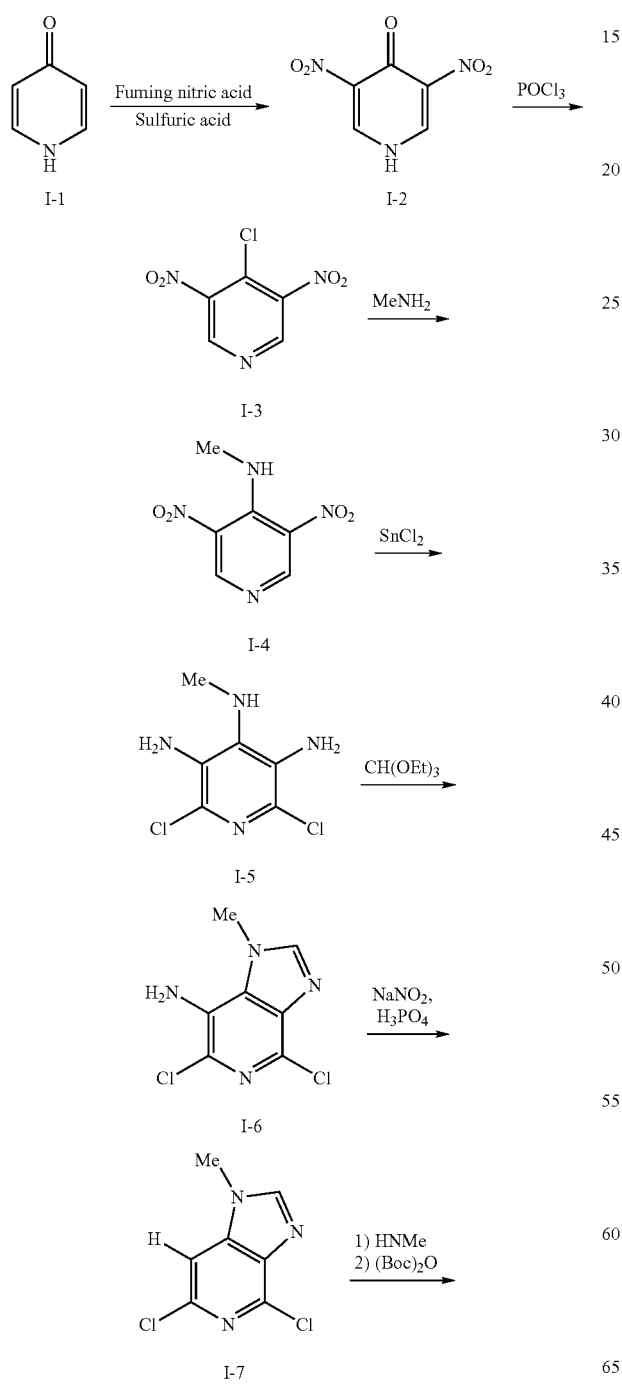

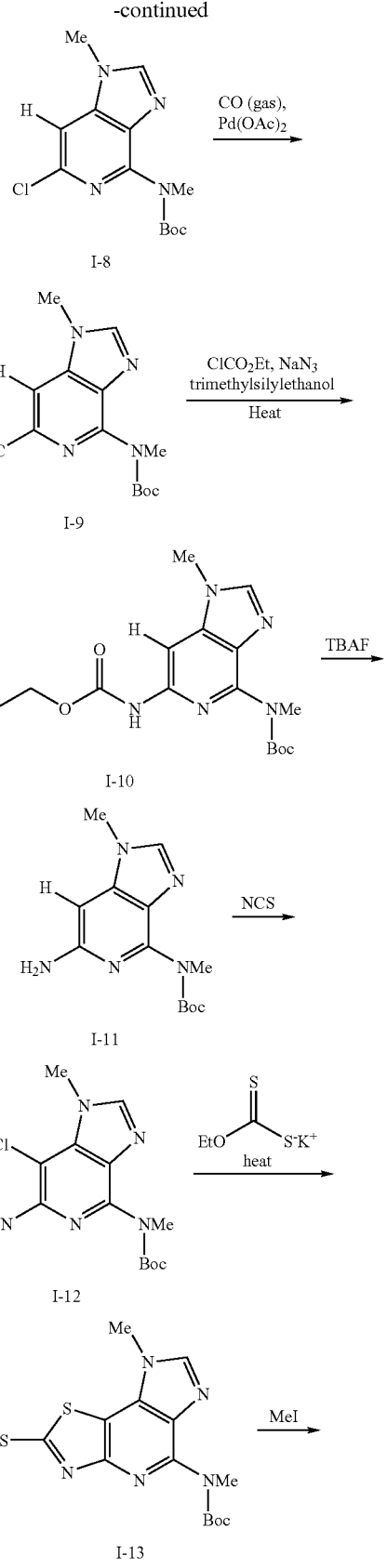

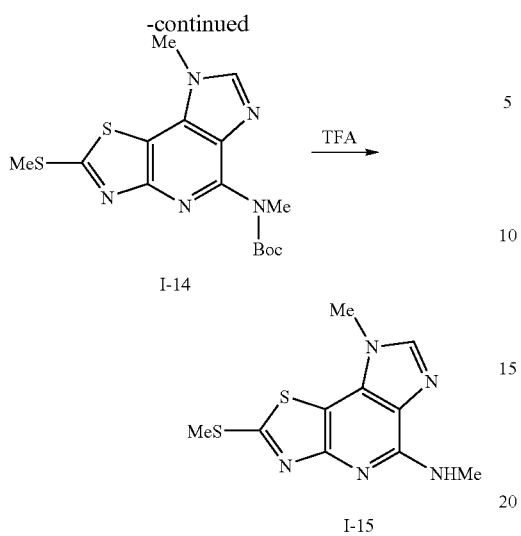

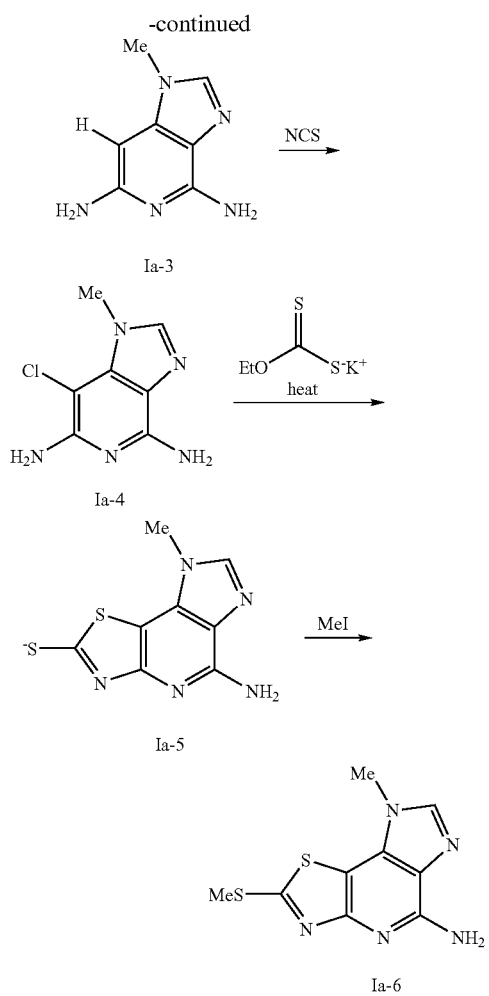

Alternatively a shorter route to compounds like I-15 is described in Scheme Ia. In this instance intermediate I-7 is reacted with an amine, such as ammonia to produce Ia-1. This intermediate can be subjected to a Buchwald amination reaction, (see Wolfe, J. P.; Tomori, H.; Sadighi, J. P.; Yin, J.; Buchwald, S. L. J. Org. Chem. (2000) 65 (4) 1158-1174.) to produce imine Ia-2. Hydrolysis of the imine under mildly acidic conditions such as 1 M HCl in ether produces amine Ia-3. This molecule can be elaborated in a manner similar to that described in Scheme I to produce Ia-5 and Ia6 which are also molecules of Formula I.

Aminothiazoles of Formula I can be prepared as depicted in Scheme II. Intermediate I-12 is reacted with benzoylisothiocyante to produce II-1. Alternatively one can envision reacting I-12 with thiophosgene followed by an amine to produce a thiourea related to intermediate II-1. Heating II-1 results in cyclization to II-2. Treatment of II-2 with trifluoroacetic acid results in removal of the Boc protecting group to provide II-3 which is also a compound of Formula I. Treatment of II-3 with aqueous hydrochloric acid at a temperature from 50° C. to 100° C. will produce amine II-4 which is also a compound of Formula I.

Scheme Ia

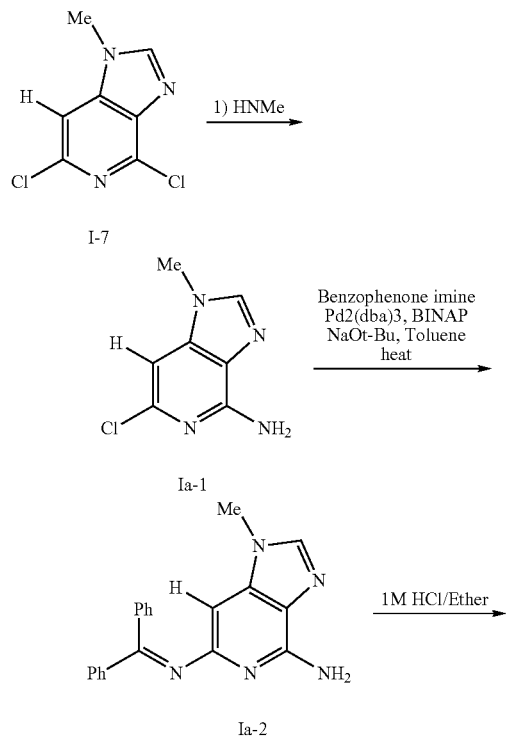

Scheme II

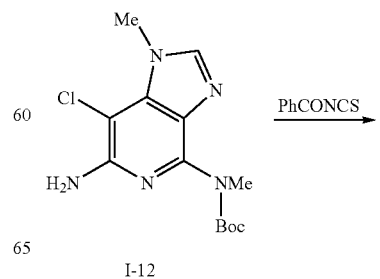

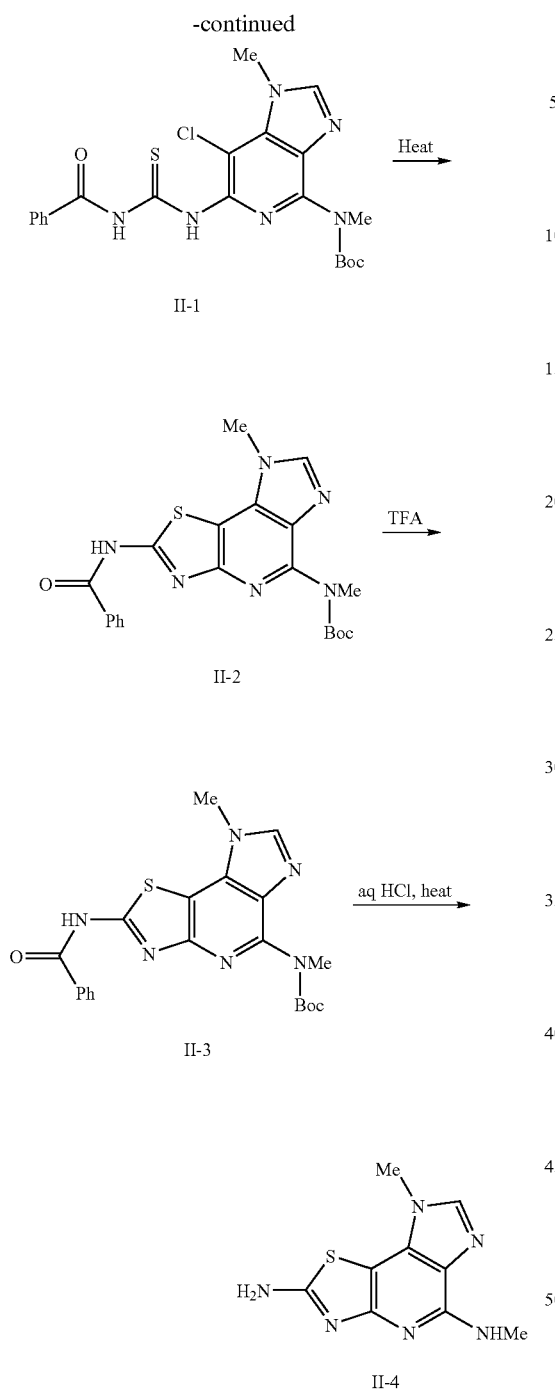

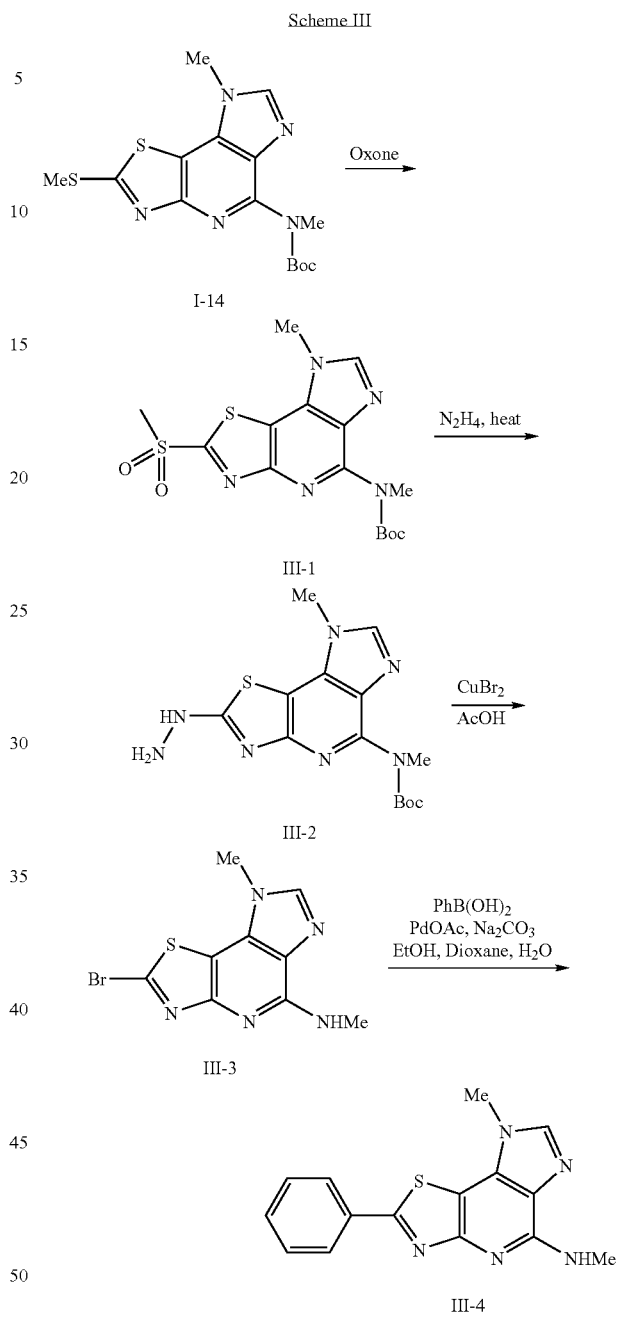

Aryl substituted thiazoles are also compounds of Formula I. The thiol of I-14 can be oxidized with a number of reagents such as Oxone® or hydrogen peroxide or meta-chloroperbenzoic acid to produce sulfone III-1. The sulfone group can be displaced by reaction with hydrazine at elevated temperature to produce compounds III-2. Reaction of hydrazine III-2 with copper bromide in acetic acid and water produce bromothiazole III-3. (In this case the Boc group was not stable under the acidic conditions) A Suzuki reaction of bromothiazole III-3 with aryl boronic acids such as phenyl boronic acid will produce compound III-4.

Alternate substitution can be introduced late into the synthetic scheme by a diazotization methodology as outlined in Scheme IV. Compound Ia-6 may be oxidized to IV-1 by treatment with a variety of oxidants including Oxone®, m-chloroperbenzoic acid, aqueous peroxide and the like. Displacement of the sulfone with hydrazine followed by copper bromide mediated substitution will produce IV-3 which is also a compound of Formula I. Suzuki reaction with an appropriate aryl or heteroaryl boronic acid, or alternatively Stille reaction with an appropriate aryl or heteroaryl tin reagent with a suitable catalyst such as palladium chloride, palladium acetate, or palladium tetrakistriphenylphosphine will produce intermediate IV-4. Diazotization of the amino group with reagents like sodium nitrite in aqueous HCl, or isoamyl nitrite or tertbutylnitrite will produce the diazonium salt which can be reacted with copper halides such as copper (II) chloride, copper (II) bromide to produce halopyridine IV-5. Displacement of the halide can be accomplished by reaction with amines at elevated temperatures or in a microwave reaction to produce IV-6, which are also compounds of Formula I. Alternatively intermediate IV-5 can be reacted with a variety of alkoxides to produce IV-7. Finally the chloro substituent of IV-5 can be removed by hydrogenation under a variety of conditions such as hydrogenation over a suitable catalyst such as 10% palladium on carbon or platinum oxide at a pressure from atmospheric to 100 psi to produce IV-8 which is also a compound of Formula I.

| Abbreviations | |
|---|---|
| aq. | Aqueous |
| CDI | Carbonyldiimidazole |
| Bn | Benzyl |
| Bu | Butyl |
| Boc | tert-butoxycarbonyl |
| DMAP | Dimethylaminopyridine |
| DMA | N,N-Dimethylacetamide |
| DMF | dimethylformamide |

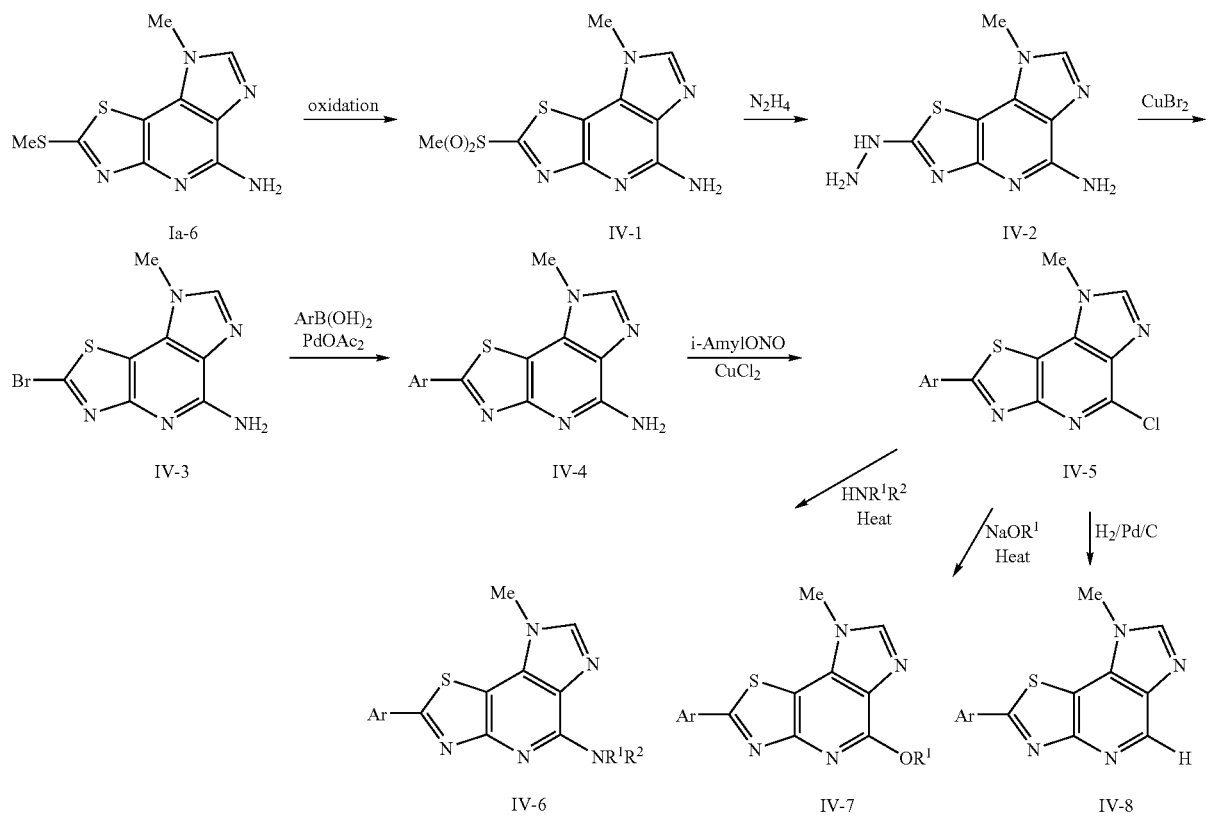

EXAMPLES

The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "A1.1" denotes the title compound of step 1 of Example A1), or by the example only where the compound is the title compound of the example (for example, "A2" denotes the title compound of Example A2).

| Abbreviations | |
|---|---|
| Ac | Acetyl |
| AcOH | Acetic acid |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| H | Hydrogen |
| h | Hours |
| i | iso |
| HPLC | High pressure liquid chromatography |
| HOAc | Acetic acid |
| Lawesson's Reagent | [2,4-bis(4-methoxyphenyl)-1,3-dithia-2,4-diphosphetane-2-4-disufide |
| LC | liquid chromatography |
| Me | Methyl |

| Abbreviations | |
|---|---|
| MeOH | Methanol |
| min. | Minutes |
| M+ | (M + H)+ |
| M+1 | (M + H)+ |
| MS | Mass spectrometry |
| n | normal |
| PhCONCS | Benzoylisothiocyanate |
| Pd/C | Palladium on carbon |
| Ph | Phenyl |
| Pr | Propyl |
| PSI | Pounds per square inch |
| Ret Time | Retention time |
| rt or RT | Room temperature |
| sat. | Saturated |
| S-Tol-BINAP | (S)-(-)-2,2'-Bis(di-p-tolylphosphino)-1,1'-binapthyl |
| t | tert |
| TFA | Trifluoroacetic acid |
| THF | Tetrahydrofuran |
| Phenominex | Phenominex, , Macclesfield, Cheshire, UK |
| YMC | YMC, Inc, Wilmington, NC 20403 |

HPLC conditions used to determine retention times; A: 2 min gradient 0-100% B in A(A; 0.1% TFA in 90/10 water/methanol; B; 0.1% TFA in 10/90 water/methanol) using a Phenominex 4.6×30 mm S-5 ODS column at with a detection wavelength of 254 nanometers or B: 4 min gradient 0-100% B in A(A; 0.1% TFA in 90/10 water/methanol; B; 0.1% TFA in 10/90 water/methanol) using a YMC Turbopack column at with a detection wavelength of 254 nanometers or 220 nanometers.

Those experiments which specify they were performed in a microwave were conducted in a SmithSynthesizer™ manufactured by Personal Chemistry. This microwave oven generates a temperature which can be selected between 60-250° C. The microwave automatically monitors the pressure which is between 0-290 PSI. Reaction times and temperatures are reported.

Example A1

N,8-Dimethyl-2-(methylthio)-8H-imidazo[4,5-d]thiazolo[4,5-b]pyridin-5-amine

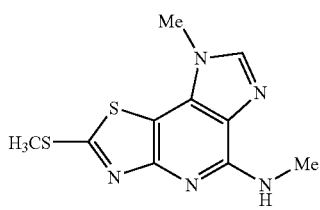

A1

A1.1: 3,5-Dinitro-1H-pyridin-4-one

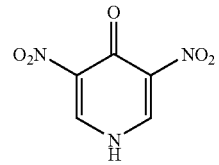

A1.1

4-Hydroxypyridine (40.0 g, 0.42 mol) was added portionwise to fuming nitric acid (140 ml) and sulfuric acid (500 ml). The resulting mixture was heated to 140° C. for 12 hours. The reaction mixture was cooled in an ice-bath and cautiously poured onto ice (500 ml). The yellow solid which precipitated was collected by filtration and dried under vacuum to yield A1.1 (70.0 g, 90%). $_1$H-NMR (DMSO-d$^6$) δ: 4.06 (2H, s). HPLC (B): 98.9%, ret. time=0.173 min., LC/MS (M–H)$_+$ =184.

A1.2: (3,5-Dinitro-pyridin-4-yl)methylamine

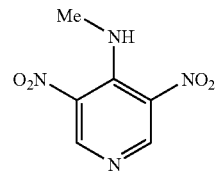

A1.2

A1.1 (10.0 g, 0.051 mol) was added portionwise to a mixture of phosphorus oxychloride (25 ml) and PCl$^5$ (17.0 g, 0.082 mol). The reaction mixture was heated to reflux under a nitrogen atmosphere for 12 hours. The reaction mixture was allowed to cool to room temperature and the phosphorus oxychloride removed in vacuo. The residue was suspended in dry THF (50 ml) and cooled to 0° C. Methylamine (32 ml, 2.0M in THF, 0.064 mol) was added drop wise over 20 minutes under a nitrogen atmosphere and the resulting solution was allowed to warm to room temperature over 1 hour. The reaction mixture was evaporated in vacuo and the residue suspended in ethyl acetate (200 ml) which was then filtered and the filtrate evaporated in vacuo to leave the crude product. The crude product was recrystallized from methanol (100 ml) to give A1.2 as a tan solid (7.2 g, 71% for two steps). HPLC (B): 98%, ret. time=1.58 min., LC/MS (M+H)$_+$=199.

A1.3: 2,6-Dichloro-N'-methyl-pyridine-3,4,5-triamine

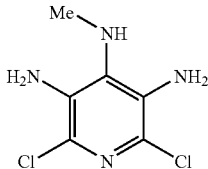

A1.3

A solution of A1.2 (60.0 g, 0.30 mol) in concentrated hydrochloric acid (300 ml) was heated to 90° C. Tin (II) chloride (85.0 g, 0.45 mol) was added portionwise over 1 hour with vigorous effervescence noted for the first equivalent of tin chloride added. The reaction mixture was heated for a further hour before the addition of more tin chloride (28.0 g, 0.15 mol) and continued heating for 2 more hours. The reaction mixture was cooled to 0° C. and cautiously basified with concentrated ammonium hydroxide (200 ml). The precipitated solid was filtered off and the filtrate extracted with ethyl acetate (5×200 ml). The combined organics were dried (MgSO4) and evaporated in vacuo to leave A1.3 as a brown solid (28.0 g, 46%). HPLC (B): 98%, ret. time=1.58 min., LC/MS (M+H)$_+$=208.

A1.4: 7-Amino-4,6-dichloro-1-methyl-1H-imidazo[4,5-c]pyridine

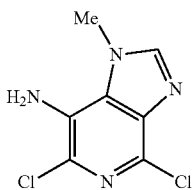

A1.4

Triethylorthoformate (25.0 ml, 0.15 mol) was added in one portion to a suspension of A1.3 (28 g, 0.14 mol) in dry acetonitrile (400 ml). The reaction mixture was heated to reflux for 4 hours and then cooled to room temperature. The reaction mixture was evaporated in vacuo to leave A1.4 as a brown powder. $_1$H-NMR (DMSO-d$^6$) δ: 8.20 (1H, s), 5.49 (2H, br. s), 4.07 (3H, s). HPLC (A): 98%, ret. time=0.78 min., LC/MS (M+H)$_+$=218.

A1.5: 4,6-Dichloro-1-methyl-1 H-imidazo[4,5-c]pyridine

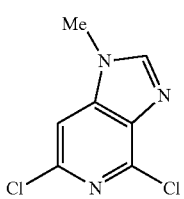

A1.5

A solution of sodium nitrite (415 mg; 6 mmol) in 2 ml of water was added drop wise over 5 minutes to a stirred solution of A1.4 (0.87 g; 4 mmol) in 14 ml of 50% aqueous H$^3$PO$^2$ at 0° C. The reaction mixture was allowed to warm to room temperature over ~2 hr. After diluting the reaction mixture with water (250 ml) and re-cooling to 0° C., the ph was adjusted to ~9 by carefully adding solid sodium carbonate. The resulting suspension was filtered. The filter cake was rinsed with water and suction dried to afford 061 g (75%) of A1.5 as a HPLC: 99%, ret. time=0.92 min., LC/MS (M+H)$_+$=202.05 (204.04, 206.02).

Alternative route to A1.5

A1.6: 2,6-Dichloro-4-methylamino-pyridine

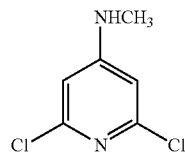

A1.6

An 8M solution of methylamine in ethanol (5 ml; 40 mmol) was added drop wise to a stirred solution of 2,4,6-trichloropyridine (5 g; 27.4 mmol) in absolute ethanol (50 ml). After heating to 55-60° C. for 24 hr, the mixture was cooled to rt and concentrated. After adding water (50 ml) to the residue, the resulting suspension was filtered and the white filter cake was washed with water (3×10 ml). After air drying, the solid was suspended in dichloromethane (25 ml) and stirred for 10 minutes. Filtration, rinsing with dichloromethane and drying afforded 2.45 g (51%) of A1.6 as a white solid. HPLC (A): 95%, ret. time=1.16 min., LC/MS (M+H)$_+$=177.00 (178.99).

A1.7: 2,6-Dichloro-4-methylamino-3-nitro-pyridine

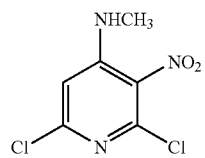

A1.7

Solid A1.6 (3.5 g, 19 mmol) was added portionwise to stirred concentrated sulfuric acid at 0° C. Effervescence was observed. 90% Fuming nitric acid (3.5 ml) was added drop wise at a rate that maintained the internal temperature below 6° C. After the addition was complete (45 minutes), the solution was stirred 10 minutes. The reaction mixture was poured onto ~100 g of ice and the resulting aqueous mixture was extracted with dichloromethane (3×100 ml). The combined organics were washed with water (200 ml), dried (MgSO$^4$/Na$^2$SO$^4$) and concentrated. The residue was dissolved in concentrated sulfuric acid (25 ml) and stirred 30 minutes at rt. Pouring the reaction mixture into ice gave a yellow suspension that was filter and dried to afford 2.45 g (49%) of A1.7 as a yellow solid. HPLC (A): 95%, ret. time=1.16 min., LC/MS (M+H)$_+$=177.00 (178.99).

A1.5: 4,6-Dichloro-1-methyl-1H-imidazo[4,5-c]pyridine

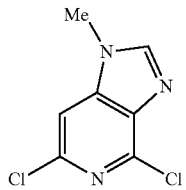

A mixture of A1.7 (2.4 g; 10.8 mmol), SnCl$^2$·2H$^2$O (9.7 g; 43 mmol) and concentrated HCl (20 ml) in methanol (80 ml) was refluxed 1 hr. After removing the volatiles in vacuo, the residue was dissolved in methanol (80 ml) and trimethylorthoformate (10 ml) was added. After refluxing 30 minutes, additional trimethylorthoformate (10 ml) was added and heating was continued for 30 minutes. After removing the volatiles in vacuo, the residue was partitioned between ethyl acetate (200 ml) and 2N NaOH (150 ml). The organic layer was washed with 2N NaOH (150 ml) and brine (100 ml). Drying (MgSO$^4$) and concentration afforded 2.12 g (97%) of A1.5 as a tan solid. HPLC (A): 98%, ret. time=0.94 min., LC/MS (M+H)$_+$=202.05 (204.04, 206.02).

A1.8: 4-Methylamino-6-chloro-1-methyl-1H-imidazo[4,5-c]pyridine

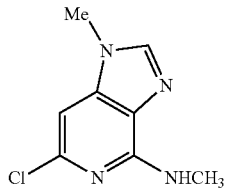

A mixture of A1.5 (0.47 g; 2.3 mmol) and 8M methylamine in ethanol (5 ml) was heated to 110° C. in a microwave apparatus for 1.5 hr. After removing the volatiles in vacuo, the residue was triturated with water, filtered and dried to afford 0.44 g (98%) of A1.8 as a tan solid. HPLC (A): 99%, ret. time=0.76 min., LC/MS (M+H)$_+$=197.14 (199.06).

A1.9: 4-[N-(Methyl)-N-(tertbutyloxycarbonyl)amino]-6-chloro-1-methyl-1H-imidazo[4,5-c]pyridine

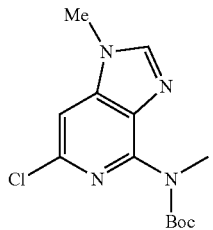

A mixture of A1.8 (0.44 g; 2.2 mmol), di-t-butyl-dicarbonate (0.6 g; 2.8 mmol) and 4-dimethylaminopyridine (0.11 g; 0.9 mmol) in acetonitrile was heated to 75° C. for 2 hr. Additional di-t-butyl-dicarbonate (0.9 g; 4.2 mmol) was added and heating was continued for 30 minutes. Additional di-t-butyl-dicarbonate (0.3 g; 1.4 mmol) was added and heating was continued for 15 minutes. After removing the volatiles in vacuo, the residue was partitioned between ethyl acetate (75 ml) and water (50 ml). The organic layer was washed with 1% potassiumbisulfate solution (30 ml), saturated sodium bicarbonate solution (20 ml) and brine (20 ml). After drying (MgSO$^4$) and concentration, the residue was chromatographed on a 2.5×18 cm silica gel column eluted with ethyl acetate. Concentration of the pure fractions afforded 0.53 g (82%) of A1.9 as a peach colored foam. $_1$H-NMR (CDCl$^3$) δ: 7.87 (1H, s), 7.24 (1H, s), 3.82 (3H, s), 3.44 (3H, s), 1.43 (9H, s).

A1.10: 4-[N-(Methyl)-N-(tertbutyloxycarbonyl)amino]-1-methyl-1H-imidazo[4,5-c]pyridine-6-carboxylic acid

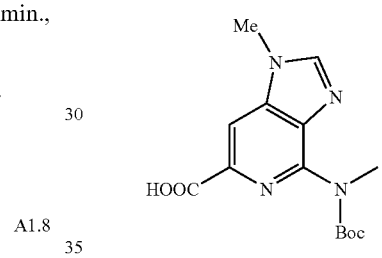

A mixture of A1.9 (0.52 g; 1.8 mmol), palladium acetate (45 mg; 0.2 mmol), 1,3-bis-(diphenylphosphino)propane (83 mg; 0.2 mmol), potassium carbonate (355 mg; 2.6 mmol) and n-butanol (10 ml) was stirred briskly at 100° C. under an atmosphere of carbon monoxide. After 2 hrs, additional palladium acetate (45 mg; 0.2 mmol) and 1,3-bis-(diphenylphosphino)propane (83 mg; 0.2 mmol) were added and heating was continued for 2 hrs. At this time, additional palladium acetate (22 mg; 0.1 mmol) and 1,3-bis-(diphenylphosphino)propane (43 mg; 0.1 mmol) were added and heating was continued for 18 hrs. After cooling to rt, methanol (40 ml) was added, followed by decolorizing carbon. After standing 10 minutes, the mixture was filtered through Celite® and the filtrate was concentrated. After co-evaporating the residue from heptane (2×20 ml), methanol (20 ml) and 1N NaOH (4 ml) were added. The resulting solution was stirred 1.5 hr at room temperature, after which time the methanol was removed in vacuo. The aqueous residue was washed with ethyl acetate (25 ml). After diluting with water (50 ml), the aqueous layer was transferred to a flask containing chloroform (50 ml). While stirring the biphasic mixture, the ph of the aqueous layer was adjusted to ~4 with 10% citric acid solution. The layers were separated and the aqueous layer was extracted with chloroform (25 ml). The combined organic layer was washed with water (50 ml), dried (MgSO$^4$) and concentrated to afford 0.58 g (99+%; contains ~5% 1,3-bis-(diphenylphosphino)propanedioxide) as an off-white solid. HPLC (A): 95%, ret. time=1.06 min., LC/MS (M+H)$_+$=207.17 (minus Boc-group). $_1$H-NMR (CDCl$^3$) δ: 8.23 (1H, s), 8.08 (1H, s), 3.96 (3H, s), 3.50 (3H, s), 1.45 (9H, s).

A1.11: 4-[N-(Methyl)-N-(tertbutyloxycarbonyl)amino]-6-2-trimethylsilylethyloxycarbonylamino-1-methyl-1H-imidazo[4,5-c]pyridine

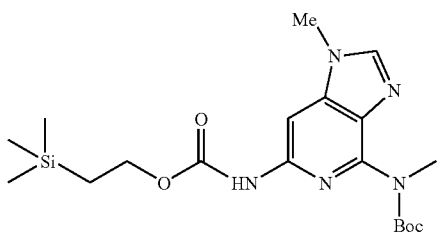

Ethyl chloroformate (0.17 ml; 1.65 mmol) was added over 1 minute to a mixture of A1.10 (0.25 g; 0.82 mmol) and triethylamine (0.24 ml; 1.65 mmol) in acetone (5 ml) at 0° C. After stirring 15 minutes at 0° C., sodium azide (108 mg; 1.65 mmol) was added as a solution in water (1 ml). After 30 minutes at 0° C., the reaction mixture was partitioned between ethyl acetate (50 ml) and water (10 ml). The organic layer was washed with brine (10 ml), dried (MgSO$_4$) and concentrated. Toluene (100 ml) was added to the residue and the resulting solution was heated to a gentle reflux. After 5 minutes, 2-(trimethylsilyl)ethanol (2.8 ml; 20 mmol) was added and reflux was continued for 5 minutes. After cooling to rt., the volatiles were removed in vacuo and the residue was chromatographed on a 2.5×10 cm silica gel column, eluted with ethyl acetate. The pure fractions were concentrated to afford 175 mg (51%) of A1.11 as a white solid. HPLC (A): 99%, ret. time=1.83 min., LC/MS (M+H)$_+$=422.28. $_1$H-NMR (CDCl$^3$) δ: 7.80 (1H, s), 7.71 (1H, s), 7.18 (1H, brs), 4.22 (2H, t, J=8.5 Hz), 3.72 (3H, s), 3.30 (3H, s), 1.35 (9H, s), 1.00 (2H, t, J=8.5 Hz), 0.03 (9H, s).

A1.12: 4-[N-(Methyl)-N-(tertbutyloxycarbonyl)amino]-6-amino-1-methyl-1H-imidazo[4,5-c]pyridine

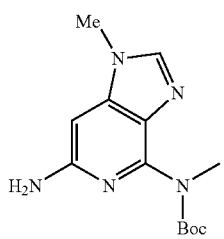

A mixture of A1.11 (172 mg; 0.41 mmol) and 1M tetra-n-butylammonium fluoride in THF (1.22 ml; 1.22 mmol) in THF (4 ml) was allowed to stand at rt. for 2.5 hr. After partitioning the reaction mixture between ethyl acetate (30 ml) and water (20 ml), the organic layer was washed with brine (10 ml) and dried (MgSO$_4$). The organic layer was filtered through a thin plug of silica gel and the filter cake was rinsed with copious amounts of ethyl acetate. Concentration of the filtrate afforded 84 mg (74%) of A1.12 as a white powder. HPLC (A): 96.5%, ret. time=0.99 min., LC/MS (M+H)$_+$=278.24 (178.24: minus Boc-group).

A1.13: 4-[N-(Methyl)-N-(tertbutyloxycarbonyl)amino]-6-amino-7-chloro-1-methyl-1H-imidazo[4,5-c]pyridine

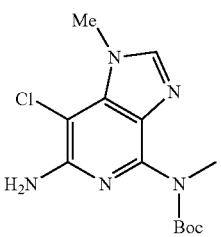

N-Chlorosuccinimide (54 mg; 0.3 mmol) was added to a solution of A1.12 (84 mg; 0.3 mmol) in acetonitrile (1.5 ml) and THF (1.5 ml) at 0° C. After stirring 10 minutes at 0° C., the reaction mixture was allowed to warm to rt. over 1.5 hr. After concentrating the reaction mixture to near dryness, the residue was partitioned between 2.5% sodium bisulfite solution (25 ml) and ethyl acetate (30 ml). The organic layer was washed with water (20 ml), brine (10 ml), dried (MgSO$_4$) and concentrated to afford 84 mg (90%) of A1.13 as a light orange solid. HPLC (A): 98%, ret. time=1.14 min., LC/MS (M+H)$_+$=312.22 [212.14 (214.10) minus Boc-group].

A1.14: N,8-Dimethyl-N-(tertbutoxycarbonyl)-2-(methylthio)-8H-imidazo[4,5-d]thiazolo[4,5-b]pyridin-5-amine

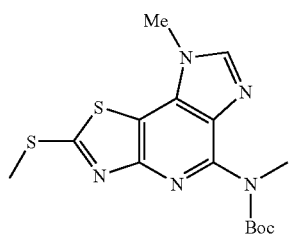

A mixture of A1.13 (50 mg; 0.16 mmol) and O-ethylxanthic acid, potassium salt (102 mg; 0.64 mmol) in DMF (1 ml) was heated to 145-150° C. for 1.5 hr. At this time, an additional amount of O-ethylxanthic acid, potassium salt (60 mg; 0.37 mmol) was added and heating was continued. After 1.5 hr., an additional amount of O-ethylxanthic acid, potassium salt (20 mg; 0.12 mmol) was added and heating was continued for 15 minutes. After cooling the reaction mixture to 0° C., iodomethane (0.08 ml; 1.25 mmol) was added and the resulting mixture was stirred for 30 minutes at 0° C. The reaction mixture was partitioned between ethyl acetate (30 ml) and water (30 ml). The organic layer was washed with water (20 ml), brine (20 ml), dried (MgSO$_4$) and concentrated to afford an orange oil that was chromatographed on a 2.5×15 cm silica gel column eluted with ethyl acetate. Concentration of the pure fractions afforded 50 mg (86%) of A1.14 as an off-white powder. HPLC (A): 99%, ret. time=1.43 min., LC/MS (M+H)$_+$=366.23 (266.15: minus Boc-group). $_1$H-NMR (CDCl$^3$) δ: 7.92 (1H, s), 4.00 (3H, s), 3.50 (3H, s), 2.90 (3H, s), 1.57 (9H, s).

47

A1: N,8-Dimethyl-2-(methylthio)-8H-imidazo[4,5-d]thiazolo[4,5-b]pyridin-5-amine

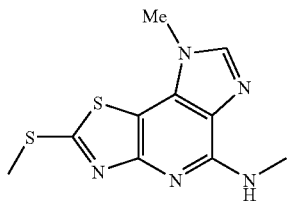

A1

A mixture of A1.14 (46 mg; 0.13 mmol) and TFA (1 ml) was allowed to stand for 15 minutes at room temperature. The volatiles were removed in vacuo and the residue was co-evaporated from ethyl acetate/heptane (4×5 ml). Drying under high vacuum afforded 47 mg (99%) of A1 as a white powder. HPLC (A): 99%, ret. time=0.96 min., LC/MS (M+H)$_+$=266.15. $_1$H-NMR (TFA-d$_1$) δ: 9.56 (1H, s), 4.71 (3H, s), 3.88 (3H, s), 3.30 (3H, s)

A1 was crystallized from ethanol to obtain colorless crystals suitable for x-ray diffraction. The x-ray experimental data is summarized in Table A1, and the graphic depiction of A1 determined from the x-ray diffraction data is shown in FIG. 1.

TABLE 1

Chemical formula: $C_{10}H_{11}N_5S_2$
a: 6.5294(4)Å
b: 8.9875(7))Å
c: 11.253(1)Å
V: 581.03(8)Å$^3$
Space group: P–1
D$_{calc}$ (g-cm$^{-3}$): 1.517
Absorption coefficient: 39.7 cm$^{-1}$
Molecular volume (V$_m$): 212
Molecular Surface Area: 320
Packing coefficient (Z · V$_m$/V$_c$): 0.73
Comments:
α: 105.809(7)°
β: 97.225(6)°
γ: 109.621(6)°
Z: 2
V/Z: 291 Å$^3$
D$_{obs}$:
Crystallization solvent: EtOH (Et$_2$O wash)
Crystal description: prisms
Melting point: 250-270° C.
Measured indices: h, ±k, ±l
Temperature (° C.): 25
(2θ)max.: 120°
No. of independent reflections: 1900
No. of observed reflections (I ≧ 3σ): 1539
No. refined variables: 154
R: 0..035
Rw: 0.054
Avg. errors (C, N, S): 0.004 Å 0.2°
Solvent: none Occupancy: none

48

Example A2

N,8-Dimethyl-2-(phenylcarbonylamino)-8H-imidazo[4,5-d]thiazolo[4.5-b]pyridin-5-amine

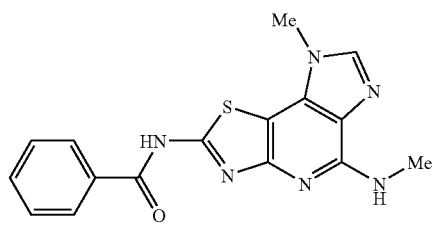

A2

A2.1: 4-[N-(Methyl)-N-(tertbutyloxycarbonyl)amino]-6-[phenylcarbonylaminothiocarbonylamino]-7-chloro-1-methyl-1H-imidazo[4,5-c]pyridine

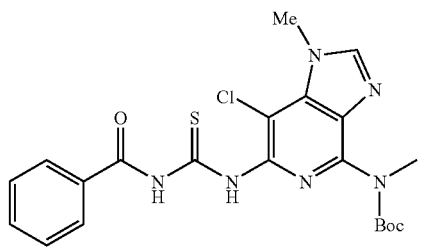

A2.1

A mixture of A1.13 (29 mg; 0.093 mmol) and benzoyl-isothiocyanate (0.016 ml; 0.11 mmol) in acetone (1 ml) was stirred 1 hr. at rt. After adding an addition amount of benzoyl-isothiocyanate (0.01 ml; 0.07 mmol), the reaction mixture was stirred for 1 hr. The volatiles were removed in vacuo and the residue was triturated with ethyl ether:hexane, 4:1. Filtration and drying afforded 22 mg (51%) of A2.1 as an off-white powder. HPLC (A): 99%, ret. time=1.65 min., LC/MS (M+H)$_+$=475.18 [375.20 (377.20): minus Boc-group].

A2.2: N,8-Dimethyl-N-(tertbutoxycarbonyl)-2-(phenylcarbonylamino)-8H-imidazo[4,5-d]thiazolo[4,5-b]pyridin-5-amine

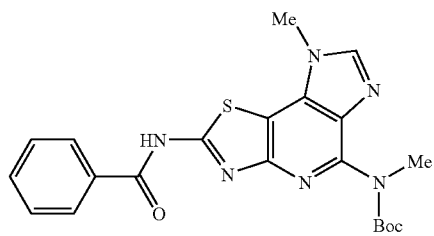

A2.2

Potassium t-butoxide, 1M in THF (0.2 ml; 0.2 mmol) was concentrated to dryness. A2.1 (21 mg; 0.045 mmol) and DMF (0.5 ml) were added and the mixture was heated to 100° C. for 1 hr. The volatiles were removed in vacuo and the residue was partitioned between ethyl acetate (15 ml) and saturated ammonium chloride solution (10 ml). The organic layer was washed with brine (10 ml), dried (MgSO⁴) and concentrated to afford 18 mg (91%) of A2.2 as an off-white solid. HPLC (A): 82%, ret. time=1.61 min., LC/MS (M+H)$_+$=439.25.

A2: N,8-Dimethyl-2-(phenylcarbonylamino)-8H-imidazo[4,5-d]thiazolo[4,5-b]pyridin-5-amine

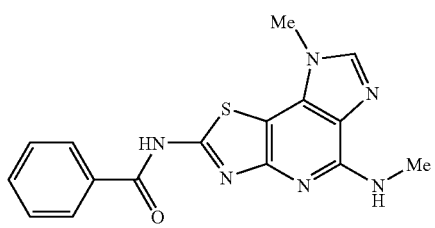

A2

A mixture of A2.2 (18 mg; 0.043 mmol) and TFA (0.4 ml) was allowed to stand for 5 minutes at room temperature. The volatiles were removed in vacuo and the residue was co-evaporated from ethyl acetate/heptane (4×5 ml). The residue was stirred as a suspension in ethyl ether for 18 hr. at rt. Filtration afforded a partially purified yellow solid. The solid was purified by Prep HPLC (reverse phase). The pure fraction was concentrated to afford 7 mg (50%) of A2 as an off-white solid. HPLC (A): 99%, ret. time=1.26 min., LC/MS (M+H)$_+$=339.15. $_1$H-NMR (TFA-d$_1$) δ: 9.08 (1H, s), 7.83 (2H, m), 7.56 (1H, m), 7.42 (2H, m), 4.22 (3H, s), 3.30 (3H, s).

Example A3

N-Methyl-2-phenyl-8H-imidazo[4,5-d]thiazolo[4,5-b]pyridin-5-amine

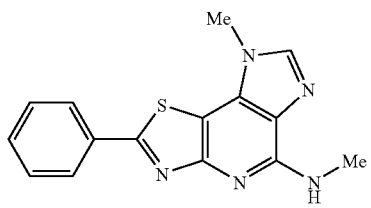

A3

A3.1: N,8-Dimethyl-N-(tertbutoxycarbonyl)-2-(methylsulfonyl)-8H-imidazo[4,5-d]thiazolo[4,5-b]pyridin-5-amine

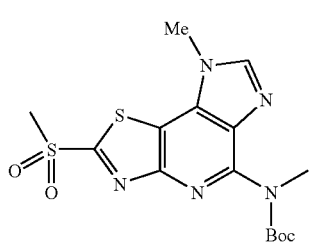

A3.1

A1.14 (1.16 g, 3.17 mmol) was dissolved in 25 mL of methanol and cooled in an ice bath. Oxone® (5.85 g, 9.52 mmol) was dissolved in 25 mL of water and added to the methanolic solution of A1.14. The ice bath was removed and the reaction mixture allowed to stir for 6 hours (HPLC analysis at 5 hours showed that no starting material remained). The methanol was removed under reduced pressure and the resulting suspension was cooled in an ice bath. The solid was collected by filtration and washed with additional cold water. The produce was dried under vacuum to yield 0.9 g (71%) of A3.1 as a white solid. LCMS: ret.time=1.20 min., (M+H)$_+$=398.15 [298.13 minus Boc-group].

A3.2: N,8-Dimethyl-N-(tertbutoxycarbonyl)-2-hydrazino-8H-imidazo[4,5-d]thiazolo[4,5-b]pyridin-5-amine

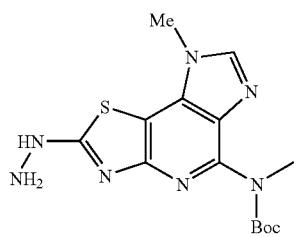

A3.2

A3.1 (0.9 g, 2.26 mmol) was dissolved in a mixture of ethanol (44 mL) and hydrazine hydrate (15 mL). The suspension was refluxed for 40 minutes (HPLC analysis at 25 minutes showed that no starting material remained) and cooled to room temperature. The solvent was removed under reduced pressure re-suspended in heptane and the solvent evaporated a second time. The residue was dissolved in enough cold water (ice bath) to permit the solid to be collected by filtration. The product was washed with additional water and dried under vacuum to yield 0.73 g (92%) of A3.2 a pale yellow solid. LCMS: ret.time=1.07 min., (M+H)$_+$=350.18 [250.12 minus Boc-group].

A3.3: 2-Bromo-N,8-Dimethyl-8H-imidazo[4,5-d]thiazolo[4,5-b]pyridin-5-amine

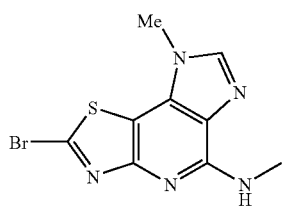

A3.3

A3.2 (0.71 g, 2.03 mmol) was dissolved in glacial acetic acid (13.9 mL). Copper (II) bromide (1.36 g, 6.09 mmol) was dissolved in a mixture of water (1.4 mL) and glacial acetic acid (1.4 mL). The solution of A3.2 was added dropwise to the copper bromide solution at room temperature. The reaction mixture became almost too thick to stir, and additional glacial acetic acid was added (2 mL). The reaction mixture was stirred for 2 hours. The reaction mixture was diluted with heptane and the solvent removed under reduced pressure. A 1:1 mixture of THF and ethyl acetate (30 mL) and a 1:1 mixture of ammonium hydroxide and saturated aqueous ammonium chloride was added (30 mL) and the insoluble solid was removed by filtration. The layers were separated and the organic layer was washed with additional 1:1 mixture of ammonium hydroxide and saturated aqueous ammonium chloride until the aqueous layer was no longer blue. (LCMS analysis of the aqueous layers suggested the presence of N,8-Dimethyl-8H-imidazo[4,5-d]thiazolo[4,5-b]pyridin-5-amine as a side product ((M+H)$_+$=220.14), however the material was not isolated at this time). The combined organic layers were dried over sodium sulfate and evaporated under reduced pressure to yield 0.32 g (53%) of A3.3 as a pale grey/green solid. LCMS: (M+H)$_+$=298.06, 300.06.

A3.4: N-Methyl-2-phenyl-8H-imidazo[4,5-d]thiazolo[4,5-b]pyridin-5-amine

A3.3 (20 mg, 0.067 mmol), phenyl boronic acid (8.9 mg, 0.073 mmol), and tetrakis(triphenylphosphine) palladium (0) (7.7 mg, 0.007 mmol) were added to 2M aqueous sodium carbonate (0.14 mL) and ethanol (0.35 mL) and toluene (0.35 mL). The reaction mixture (suspension) was heated to reflux in an oil bath maintained at 110° C. HPLC demonstrated the reaction had not proceeded to completion after ~0.5 h. Additional ethanol (0.35 mL) and 1,4-dioxane (1.0 mL) was added and the heating continued during which time the material appeared to go into solution. After an additional 1 h. and 2 h additional portions of tetrakis(triphenylphosphine) palladium (0) (7.7 mg, 0.007 mmol) and 2M aqueous sodium carbonate (0.14 mL) were added in an effort to aid completion of the reaction. After an additional 40 minutes the reaction mixture was allowed to cool to room temperature, heptane added, and the solvent was removed under reduced pressure. The crude product was purified by flash column chromatography (silica gel, 80:20 ethyl acetate/hexane (100 mL), then ethyl acetate (100 mL) then 98:2 ethyl acetate/methanol (100 mL) then 95:5 ethyl acetate/methanol (100 mL) then 95:7:2 Ethyl acetate/methanol/ammonium hydroxide (100 mL)) to yield 13.7 mg of A3 which was determined to be 89% pure by analytical HPLC. The crude produce was triturated with 80:20 ether/hexane to yield 9.5 mg of A3 as a pale yellow solid. Analytical HPLC 93.9% purity. LCMS: ret time=1.23 min. (M+H)$_+$=296.13, $_1$H NMR (CDCl$^3$) δ 8.18-8.16 m, 2H; 7.57, s, 1H; 7.49-7.47 m, 3H; 5.64 br s, 1 H; 4.02, s, 3H; 3.27, d, J=7.6 Hz, 3H;

Intermediate A4a (S)-3-(1-Acetamidoethyl)phenylboronic acid

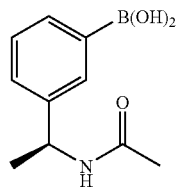

A4a.1: (S)—N-[1-(3-Bromophenyl)ethyl]Acetamide

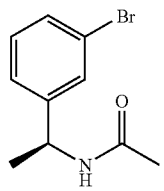

Commercially available (S)-1-(3-bromophenyl)ethanamine (1.0 g, 5 mmol) was dissolved in THF (20 mL). Pyridine (0.5 mL) and acetic anhydride (0.51 g, 5 mmol) were added and the reaction mixture allowed to stir at room temperature overnight. The solvent was removed under reduced pressure to provide A4a.1 (1.23 g) as a clear yellowish liquid. (M+H)$_+$=242.15, 244.16.

A4a.2: (S)-3-(1-Acetamidoethyl)phenylboronic acid

A4a.1 (1.23 g, 5 mmol), bis-pinacolatodiborane (1.33 g, 5 mmol), potassium acetate (1.47 g, 15 mmol) and palladium acetate (224 mg, 1 mmol) were added to degassed DMF (anhydrous). The reaction mixture was heated at 80° C. overnight. The next day additional palladium acetate was added (610 mg, 2.5 mmol) was added and the reaction mixture heated overnight. The reaction mixture was cooled to room temperature and filtered through a pad of silica gel (washing with ethyl acetate). The filtrate was concentrated under reduced pressure with provided approximately 1.41 g of (S)—N-(1-(3-(4,4,5,5-tetramethyl-1,3,2-dioxaborolan-2-yl)phenyl)ethyl)acetamide (LCMS (M+H)$_+$=290.31). The product was dissolved in methanol and purified by reverse phase column chromatography (during which time the boronate ester underwent hydrolysis) to yield 875 mg (~70%) of the chiral boronic acid. (M+H)$_+$=208.17

Intermediate A4b (R)-3-(1-Acetamidoethyl)phenylboronic acid

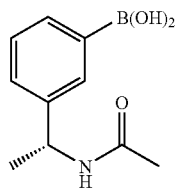

A4b.1: (R)-N-[1-(3-Bromophenyl)ethyl]Acetamide

The title compound was made in a similar manner as for A4a.1 starting from commercially available (S)-1-(3-bromophenyl)ethanamine. (M+H)$_+$=242.15, 244.16.

A4b.2: (R)-3-(1-Acetamidoethyl)phenylboronic acid

The title compound was made in a similar manner for A4a as described in step A4a.2 starting from A4b.1. (M+H)$_+$=208.17.

Examples A4-A5

Examples A2-A5 was prepared in a similar manner to that used for Example A3 substituting the appropriate boronic acid in the place of phenyl boronic acid.

TABLE A1

| Ex. | R$^1$ | Name | HPLC Retention (min) | MS Reported |
|---|---|---|---|---|
| A4 | 3-(1-acetamidoethyl)phenyl, (S) | (S)-N-[1-[5-[8-methyl-5-(methylamino)-8H-imidazo[4,5-d]thiazolo[4,5-b]pyridine-2-yl]phenyl]ethyl]acetamide | 1.16 | 381.26 |
| A5 | 3-(1-acetamidoethyl)phenyl, (R) | (R)-N-[1-[5-[8-methyl-5-(methylamino)-8H-imidazol[4,5-d]thiazolo[4,5-b]pyridine-2-yl]phenyl]ethyl]acetamide | 1.15 | 381.12 |
| A6 | 3-carbamoylphenyl | 2-[8-methyl-5-(methylamino)-8H-imidazol[4,5-d]thiazolo[4,5-b]pyridin-2-yl]-benzamide | 0.85 | 339.23 |
| A7 | 3-fluorophenyl | 2-(3-fluorophenyl)-N,8-dimethyl-8H-imidazo[4,5-d]thiazolo[4,5-b]pyridin-5-amine | 1.49 | 314.18 |

Example A8

2-[4-(aminomethyl)phenyl]-N,8-dimethyl-8H-imidazo[4,5-d]thiazolo[4,5-b]pyridin-5-amine

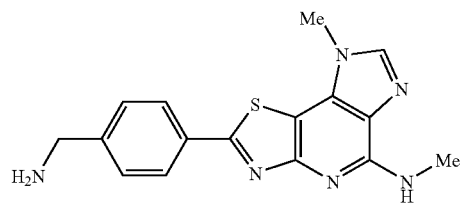

A8

A3.3 (20 mg, 0.067 mmol), 4-(t-butyloxycarbonylaminomethyl)phenylboronic acid (18.6 mg 0.074 mmol) and tetrakis(triphenylphosphine)palladium (0) (7.74 mg, 0.007 mmol) was added to a mixture of 2M aqueous sodium carbonate (0.14 mL) dioxane (0.35 mL) and ethanol (0.35 mL). The reaction mixture was heated under an argon atmosphere for 50 min. at 100° C. The reaction mixture was allowed to cool to room temperature and the solvent was removed under reduced pressure. Dichloromethane (1 mL) was added and the suspension cooled in an ice bath. Trifluoroacetic acid (1 mL) was added and the reaction mixture stirred at 0° C. for 45 min. The solvent was removed under reduced pressure and the crude product was dissolved in methanol and purified by automated reverse phase chromatography. The appropriate fractions were combined and the solvent removed under reduced pressure with the aid of heptane as an azeotroping agent to yield 19.8 mg of product as a pale yellow solid. M+H+=325.27. NMR 400 MHz $d^6$DMSO δ 8.29 s, 1H, 8.28-8.20 br s, 2H, 8.17 d, J=8.2 hz, 2H, 7.65 d, J=8.2 Hz, 2 H, 4.20-4.10 apparent quartet, 2H, 4.03, s, 3H, 3.06, s, 3H.

Example A9

N-[[4-[8-methyl-5-(methylamino)-8H-imidazo[4,5-d]thiazolo[4,5-b]pyridin-2-yl]phenyl]methyl]acetamide

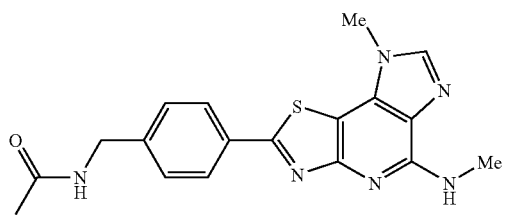

A9

A8 (30.0 mg, 0.083 mmol), acetic acid (6.6 mg, 0.11 mmol), EDC (31.7 mg, 0.17 mmol), 1-hydroxybenzotriazole monohydrate (15 mg, 1.0 mmol) and diisopropylethylamine (42 mg, 0.33 mmol) was suspended in THF (2 mL). The reaction mixture was stirred for 2 h. under an argon atmosphere at 60° C. The solvent was removed under reduced pressure and the reaction was purified by automated reverse phase HPLC. The appropriate fractions were combined and the solvent removed under reduced pressure to yield 9 mg of the product as a pale yellow solid. M+H+=367.28. NMR 500 MHz $d^6$DMSO δ: 8.43 br s, 1H, 8.19 s, 1H, 8.03 d, J=9 Hz, 2 H, 7.42 d, J=9 Hz, 2H, 7.06-7.05 br s, 1H, 4.32 d, J=6 Hz, 2H, 4.00 s, 3H, 3.00 d, J=5 Hz, 3H, 1.90 s, 3H.

This material was also free based by the addition of saturated sodium bicarbonate, however this step was not conducted for the production of the compounds in Table A2.

TABLE A2

Examples A10-A43 described in Table A2 were prepared in a similar manner to that used for Example A9 substituting the appropriate acid. In cases where the acid contained an amine which contained a Boc protecting group the material was treated with an excess of TFA for 1 hour prior to purification by automated reverse phase HPLC.

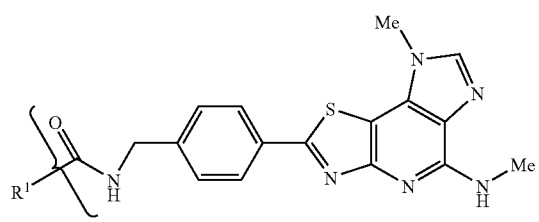

| Ex. | R¹ | Name | HPLC* Retention (min) | MS Reported |
|---|---|---|---|---|
| A10 | piperidinyl-CH2CH2- | N-[[4-[8-methyl-5-(methylamino)-8H-imidazo[4,5-d]thiazolo[4,5-b]pyridin-2-yl]phenyl]methyl]-1-piperidinepropanamide | 1.49 | 464.30 |

TABLE A2-continued

Examples A10-A43 described in Table A2 were prepared in a similar manner to that used for Example A9 substituting the appropriate acid. In cases where the acid contained an amine which contained a Boc protecting group the material was treated with an excess of TFA for 1 hour prior to purification by automated reverse phase HPLC.

| Ex. | R¹ | Name | HPLC* Retention (min) | MS Reported |
|---|---|---|---|---|
| A11 | NH₂CH₂— | 2-amino-N-[[4-[8-methyl-5-(methylamino)-8H-imidazo[4,5-d]thiazolo[4,5-b]pyridin-2-yl]phenyl]methyl]-acetamide | 1.41 | 382.25 |
| A12 | (2S)-pyrrolidinyl | N-[[4-[8-methyl-5-(methylamino)-8H-imidazo[4,5-d]thiazolo[4,5-b]pyridin-2-yl]phenyl]methyl]-, (2S)-2-pyrrolidinecarboxamide | 1.52 | 422.29 |
| A13 | (2R)-pyrrolidinyl | N-[[4-[8-methyl-5-(methylamino)-8H-imidazo[4,5-d]thiazolo[4,5-b]pyridin-2-yl]phenyl]methyl]-, (2R)-2-pyrrolidinecarboxamide | 1.52 | 422.27 |
| A14 | 3-(methylsulfonyl)phenyl | N-[[4-[8-methyl-5-(methylamino)-8H-imidazo[4,5-d]thiazolo[4,5-b]pyridin-2-yl]phenyl]methyl]-3-(methylsulfonyl)-benzamide | 2.09 | 507.25 |
| A15 | 5-methyl-isoxazol-3-yl | 5-methyl-N-[[4-[8-methyl-5-(methylamino)-8H-imidazo[4,5-d]thiazolo[4,5-b]pyridin-2-yl]phenyl]methyl]-3-isoxazolecarboxamide | 2.18 | 434.26 |
| A16 | t-Bu | N-[[4-[8-methyl-5-(methylamino)-8H-imidazo[4,5-d]thiazolo[4,5-b]pyridin-2-yl]phenyl]methyl]-2,2-dimethylpropanamide, | 2.22 | 409.29 |
| A17 | 2-pyridyl | N-[[4-[8-methyl-5-(methylamino)-8H-imidazo[4,5-d]thiazolo[4,5-b]pyridin-2-yl]phenyl]methyl]-2-pyridinecarboxamide | 2.19 | 430.26 |
| A18 | cyclopropyl | N-[[4-[8-methyl-5-(methylamino)-8H-imidazo[4,5-d]thiazolo[4,5-b]pyridin-2-yl]phenyl]methyl] cyclopropanecarboxamide | 1.98 | 393.27 |

TABLE A2-continued

Examples A10-A43 described in Table A2 were prepared in a similar manner to that used for Example A9 substituting the appropriate acid. In cases where the acid contained an amine which contained a Boc protecting group the material was treated with an excess of TFA for 1 hour prior to purification by automated reverse phase HPLC.

| Ex. | R¹ | Name | HPLC* Retention (min) | MS Reported |
|---|---|---|---|---|
| A19 | 3-pyridylmethyl | N-[[4-[8-methyl-5-(methylamino)-8H-imidazo[4,5-d]thiazolo[4,5-b]pyridin-2-yl]phenyl]methyl]-3-pyridineacetamide | 1.55 | 444.28 |
| A20 | (2S)-1-acetylpyrrolidin-2-yl | 1-acetyl-N-[[4-[8-methyl-5-(methylamino)-8H-imidazo[4,5-d]thiazolo[4,5-b]pyridin-2-yl]phenyl]methyl]-, (2S)-2-pyrrolidinecarboxamide | 1.81 | 464.30 |
| A21 | (2S)-5-oxopyrrolidin-2-yl | N-[[4-[8-methyl-5-(methylamino)-8H-imidazo[4,5-d]thiazolo[4,5-b]pyridin-2-yl]phenyl]methyl]-5-oxo-, (2S)-2-pyrrolidinecarboxamide | 1.66 | 436.26 |
| A22 | iPr | 2-methyl-N-[[4-[8-methyl-5-(methylamino)-8H-imidazo[4,5-d]thiazolo[4,5-b]pyridin-2-yl]phenyl]methyl]propanamide | 2.02 | 395.29 |
| A23 | tBu-CH₂ | 3,3-dimethyl-N-[[4-[8-methyl-5-(methylamino)-8H-imidazo[4,5-d]thiazolo[4,5-b]pyridin-2-yl]phenyl]methyl]-butanamide | 2.47 | 423.31 |
| A24 | 1-methylcyclopropyl | 1-methyl-N-[[4-[8-methyl-5-(methylamino)-8H-imidazo[4,5-d]thiazolo[4,5-b]pyridin-2-yl]phenyl]methyl]-cyclopropanecarboxamide | 2.13 | 407.28 |
| A25 | pyrazin-2-yl | N-[[4-[8-methyl-5-(methylamino)-8H-imidazo[4,5-d]thiazolo[4,5-b]pyridin-2-yl]phenyl]methyl]-2-pyrazinecarboxamide | 2.02 | 431.26 |
| A26 | 2-(methylsulfonyl)phenyl | N-[[4-[8-methyl-5-(methylamino)-8H-imidazo[4,5-d]thiazolo[4,5-b]pyridin-2-yl]phenyl]methyl]-2-(methylsulfonyl)-benzamide | 2.03 | 507.26 |

TABLE A2-continued

Examples A10-A43 described in Table A2 were prepared in a similar manner to that used for Example A9 substituting the appropriate acid. In cases where the acid contained an amine which contained a Boc protecting group the material was treated with an excess of TFA for 1 hour prior to purification by automated reverse phase HPLC.

| Ex. | R¹ | Name | HPLC* Retention (min) | MS Reported |
|---|---|---|---|---|
| A27 | (tetrahydrofuran-2-yl, gem-dimethyl) | tetrahydro-N-[[4-[8-methyl-5-(methylamino)-8H-imidazo[4,5-d]thiazolo[4,5-b]pyridin-2-yl]phenyl]methyl]-2-furancarboxamide | 1.94 | 423.28 |
| A28 | EtO-C(CH₃)₂- | 2-ethoxy-N-[[4-[8-methyl-5-(methylamino)-8H-imidazo[4,5-d]thiazolo[4,5-b]pyridin-2-yl]phenyl]methyl]-acetamide | 2.01 | 411.28 |
| A29 | pyridazin-4-yl | N-[[4-[8-methyl-5-(methylamino)-8H-imidazo[4,5-d]thiazolo[4,5-b]pyridin-2-yl]phenyl]methyl]-4-pyridazinecarboxamide | 1.86 | 431.25 |
| A30 | 2-chloropyridin-3-yl | 2-chloro-N-[[4-[8-methyl-5-(methylamino)-8H-imidazo[4,5-d]thiazolo[4,5-b]pyridin-2-yl]phenyl]methyl[-3-pyridinecarboxamide | 2.02 | 464.22 |
| A31 | 6-chloropyridin-3-yl | 6-chloro-N-[[4-[8-methyl-5-(methylamino)-8H-imidazo[4,5-d]thiazolo[4,5-b]pyridin-2-yl]phenyl]methyl]-3-pyridinecarboxamide, | 2.33 | 464.23 |
| A32 | pyridin-3-yl | N-[[4-[8-methyl-5-(methylamino)-8H-imidazo[4,5-d]thiazolo[4,5-b]pyridin-2-yl]phenyl]methyl]-3-pyridinecarboxamide | 1.70 | 430.25 |
| A33 | 6-cyanopyridin-3-yl | 6-cyano-N-[[4-[8-methyl-5-(methylamino)-8H-imidazo[4,5-d]thiazolo[4,5-b]pyridin-2-yl]phenyl]methyl]-3-pyridinecarboxamide | 2.15 | 455.25 |
| A34 | benzyl, gem-dimethyl | N-[[4-[8-methyl-5-(methylamino)-8H-imidazo[4,5-d]thiazolo[4,5-b]pyridin-2-yl]phenyl]methyl]-benzeneacetamide | 2.37 | 443.28 |

TABLE A2-continued

Examples A10-A43 described in Table A2 were prepared in a similar manner to that used for Example A9 substituting the appropriate acid. In cases where the acid contained an amine which contained a Boc protecting group the material was treated with an excess of TFA for 1 hour prior to purification by automated reverse phase HPLC.

| Ex. | R¹ | Name | HPLC* Retention (min) | MS Reported |
|---|---|---|---|---|
| A35 | 1-methyl-4-piperidinyl | 1-methyl-N-[[4-[8-methyl-5-(methylamino)-8H-imidazo[4,5-d]thiazolo[4,5-b]pyridin-2-yl]phenyl]methyl]-4-piperidinecarboxamide | 1.53 | 450.32 |
| A36 | 1-methyl-3-piperidinyl | 1-methyl-N-[[4-[8-methyl-5-(methylamino)-8H-imidazo[4,5-d]thiazolo[4,5-b]pyridin-2-yl]phenyl]methyl]-3-piperidinecarboxamide | 1.54 | 450.32 |
| A37 | (2S)-6-oxo-2-piperidinyl | N-[[4-[8-methyl-5-(methylamino)-8H-imidazo[4,5-d]thiazolo[4,5-b]pyridin-2-yl]phenyl]methyl]-6-oxo-,(2S)-2-piperidinecarboxamide | 1.74 | 450.28 |
| A38 | MeO-C(Me)₂- | 2-methoxy-N-[[4-[8-methyl-5-(methylamino)-8H-imidazo[4,5-d]thiazolo[4,5-b]pyridin-2-yl]phenyl]methyl]-acetamide | 1.81 | 397.24 |
| A39 | 6-methyl-2-pyridinyl | 6-methyl-N-[[4-[8-methyl-5-(methylamino)-8H-imidazo[4,5-d]thiazolo[4,5-b]pyridin-2-yl]phenyl]methyl]-2-pyridinecarboxamide | 2.40 | 444.27 |
| A40 | 3-methyl-2-pyridinyl | 3-methyl-N-[[4-[8-methyl-5-(methylamino)-8H-imidazo[4,5-d]thiazolo[4,5-b]pyridin-2-yl]phenyl]methyl]-2-pyridinecarboxamide | 2.23 | 444.27 |
| A41 | propyl | N-[[4-[8-methyl-5-(methylamino)-8H-imidazo[4,5-d]thiazolo[4,5-b]pyridin-2-yl]phenyl]methyl]-butanamide | 2.07 | 395.27 |

TABLE A2-continued

Examples A10-A43 described in Table A2 were prepared in a similar manner to that used for Example A9 substituting the appropriate acid. In cases where the acid contained an amine which contained a Boc protecting group the material was treated with an excess of TFA for 1 hour prior to purification by automated reverse phase HPLC.

| Ex. | R$^1$ | Name | HPLC* Retention (min) | MS Reported |
|---|---|---|---|---|
| A42 | NC-(cyclopropyl-C(Me)) | 1-cyano-N-[[4-[8-methyl-5-(methylamino)-8H-imidazo[4,5-d]thiazolo[4,5-b]pyridin-2-yl]phenyl methyl]-cyclopropanecarboxamide | 2.04 | 418.26 |
| A43 | NC-C(Me)$_2$- | 2-cyano-N[[4-[8-methyl-5-(methylamino)-8H-imidazo[4,5-d]thiazolo[4,5-b]pyridin-2-yl]phenyl]methyl]-acetamide | 1.73 | 392.24 |

HPLC conditions: 4 min gradient 10-90% water→methanol + 0.2% phosphoric acid. Column YMC S5 ODS CombiScreen ® 4.6 × 50 mm, detected at 220 nM wavelength

Example A44

[[3-[8-methyl-5-(methylamino)-8H-imidazo[4,5-d]thiazolo[4,5-b]pyridin-2-yl]phenyl]methyl]carbamic acid 1,1-dimethylethyl ester

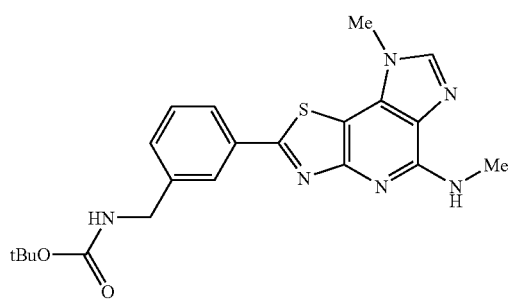

A44

A3.3 (25 mg, 0.084 mmol), 3-(t-butyloxycarbonylaminomethyl)phenylboronic acid (21 mg, 0.085 mmol) and tetrakis(triphenylphosphine)palladium (0) (9.7 mg, 0.008 mmol) was added to a mixture of 2M aqueous sodium carbonate (0.18 mL) dioxane (0.40 mL) and ethanol (0.40 mL). The reaction mixture was heated under argon for 50 minutes at 100° C. The reaction mixture allowed to cool to room temperature and the solvents were removed under reduced pressure. Water (6 mL) was added and placed in an ice bath. The precipitate was collected by filtration, washed with additional water and dried under vacuum. The solid was rinsed with hexane to yield 38.8 mg of a tan solid. The crude product was purified by flash silica gel column chromatography (98:2 ethyl acetate/methanol→50:48:1:1 THF/ethyl acetate/methanol/ammonium hydroxide→50:45:3:2 THF/ethyl acetate/methanol/ammonium hydroxide. Fractions for which the desired mass were obtained were combined and the solvent removed under reduced pressure. The solid was suspended in hexane, filtered and rinsed with additional hexane. The solid was then triturated with a mixture of 90:10 ether/ethyl acetate to yield 10.4 mg of the desired product as a pale yellow solid. M+H+=425.24. $_1$H NMR 400 MHz d$^6$DMSO δ 8.24 s, 1H, 8.06-7.90 m, 2H, 7.60-7.48, m, 2H, 7.40 br s, 1 H, 7.10 br s, 1H, 4.24 br s, 2H, 4.06, s, 3H, 3.06, br s, 3H, 1.48 s, 9H.

Example A45

2-[3-(aminomethyl)phenyl]-N,8-dimethyl-8H-imidazo[4,5-d]thiazolo[4,5-b]pyridin-5-amine

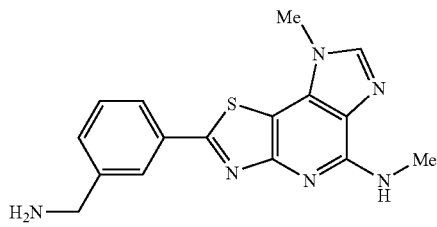

A45

A44 (0.26 g, 7.69 mmol) was suspended (almost in solution) in a mixture of dichloromethane (10 mL) and methanol (3.5 mL). 4N HCl in dioxane (3.85 mL, 15.4 mmol) was added at room temperature. The reaction mixture became warm to the touch and was stirred at ambient temperature for 50 min. The solvents were removed under reduced pressure, suspended in diethyl ether and evaporated. The residue was triturated overnight with a 90:5:5 mixture of ether/toluene/ethyl acetate. The solid was collected and triturated for 2h with toluene and 1 h with ethyl acetate and filtered to yield 223 mg of a tan solid M+H+=325.20. NMR 400 MHz d⁶DMSO δ 8.32-8.20 m, 3H, 8.14-9.08 m, 1H, 7.68-7.60, m, 2H, 4.24-4.16 apparent quartet, 2H, 4.03, s, 3H, 3.05, br s, 3H.

TABLE A3

Examples A46-A59 described in Table A3 were prepared in a similar manner to that used for Example A9 substituting the appropriate acid starting with amine A45.

| Ex. | R¹ | Name | HPLC Retention (min) | MS Reported |
|---|---|---|---|---|
| A46 | CH₃— | N-[[3-[8-methyl-5-(methylamino)-8H-imidazo[4,5-d]thiazolo[4,5-b]pyridin-2-yl]phenyl]methyl]acetamide | 1.14 | 367.24 |
| A47 | | N-[[3-[8-methyl-5-(methylamino)-8H-imidazo[4,5-d]thiazolo[4,5-b]pyridin-2-yl]phenyl]methyl]cyclopropanecarboxamide, | 2.13 | 393.41 |
| A48 | | 2-(acetylamino)-N-[[3-[8-methyl-5-(methylamino)-8H-imidazo[4,5-d]thiazolo[4,5-b]pyridin-2-yl]phenyl]methyl]acetamide, | 1.81 | 424.39 |
| A49 | | N-[[3-[8-methyl-5-(methylamino)-8H-imidazo[4,5-d]thiazolo[4,5-b]pyridin-2-yl]phenyl]methyl]-5-oxo-, (2R)-2-pyrrolidinecarboxamide | 1.86 | 436.40 |
| A50 | | N-[[3-[8-methyl-5-(methylamino)-8H-imidazo[4,5-d]thiazolo[4,5-b]pyridin-2-yl]phenyl]methyl]-4-pyridinecarboxamide | 1.87 | 430.41 |
| A51 | | N-[[3-[8-methyl-5-(methylamino)-8H-imidazo[4,5-d]thiazolo[4,5-b]pyridin-2-yl]phenyl]methyl]-1-piperidinepropanamide | 1.79 | 464.41 |
| A52 | | N-[[3-[8-methyl-5-(methylamino)-8H-imidazo[4,5-d]thiazolo[4,5-b]pyridin-2-yl]phenyl]methyl]-2-(methylsulfonyl)-benzamide | 2.18 | 507.28 |

TABLE A3-continued

Examples A46-A59 described in Table A3 were prepared in a similar manner to that used for Example A9 substituting the appropriate acid starting with amine A45.

| Ex. | R¹ | Name | HPLC Retention (min) | MS Reported |
|---|---|---|---|---|
| A53 | (4-piperidinyl, NH) | N-[[3-[8-methyl-5-(methylamino)-8H-imidazo[4,5-d]thiazolo[4,5-b]pyridin-2-yl]phenyl]methyl]-4-piperidinecarboxamide | 1.72 | 436.42 |
| A54 | (1,2,3-thiadiazol-4-yl) | N-[[3-[8-methyl-5-(methylamino)-8H-imidazo[4,5-d]thiazolo[4,5-b]pyridin-2-yl]phenyl]methyl]-1,2,3-thiadiazole-4-carboxamide | 2.21 | 437.35 |
| A55 | (2R)-pyrrolidin-2-yl | N-[[3-[8-methyl-5-(methylamino)-8H-imidazo[4,5-d]thiazolo[4,5-b]pyridin-2-yl]phenyl]methyl]-, (2R)-2-pyrrolidinecarboxamide | 1.69 | 422.41 |
| A56 | 1-hydroxycyclopropyl | 1-hydroxy-N-[[3-[8-methyl-5-(methylamino)-8H-imidazo[4,5-d]thiazolo[4,5-b]pyridin-2-yl]phenyl]methyl]-cyclopropanecarboxamide | 1.99 | 409.42 |
| A57 | tert-butyl (C(Me)₃) | N-[[3-[8-methyl-5-(methylamino)-8H-imidazo[4,5-d]thiazolo[4,5-b]pyridin-2-yl]phenyl]methyl]-2,2-dimethyl-propanamide | 2.34 | 409.41 |
| A58 | 1-methyl-1H-imidazol-4-yl | 1-methyl-N-[[3-[8-methyl-5-(methylamino)-8H-imidazo[4,5-d]thiazolo[4,5-b]pyridin-2-yl]phenyl]methyl]-1H-imidazole-4-carboxamide | 1.79 | 433.35 |
| A59 | 1-methylpiperidin-4-yl | 1-methyl-N-[[3-[8-methyl-5-(methylamino)-8H-imidazo[4,5-d]thiazolo[4,5-b]pyridin-2-yl]phenyl]methyl]-4-piperidinecarboxamide | 1.72 | 450.40 |

Example A60

8-methyl-2-phenyl-8H-imidazo[4,5-d]thiazolo[4,5-b]pyridin-5-amine

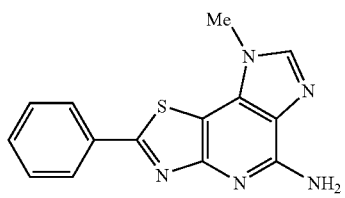

A60.1: 4-[N-[(4-methoxyphenyl)methyl]-N-(tertbutyloxycarbonyl)amino]-6-amino-1-methyl-1H-imidazo[4,5-c]pyridine

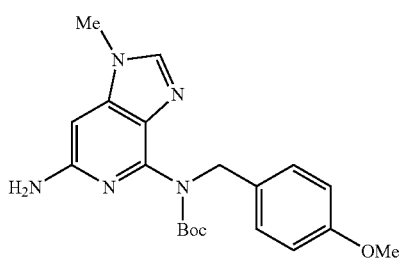

Compound A60.1 was prepared in an manner analogous to compound that used to prepare intermediate A1.8 substituting 4-methoxybenzylamine for methylamine, and carrying that material through the same procedures for steps A1.9, A1.10, A1.11 and A1.12.

A60.2: 4-[N-[(4-methoxylphenyl)methyl]-N-(tertbutyloxycarbonyl)amino]-6-amino-7-chloro-1-methyl-1H-imidazo[4,5-c]pyridine

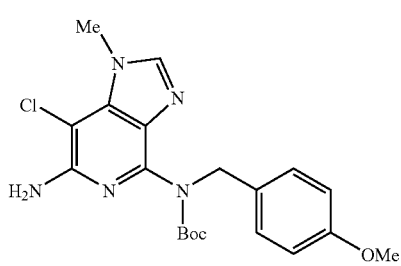

A60.1 (0.93 g, 2.42 mmol) was dissolved in methanol (70 mL) and stirred at room temperature. N-chlorosuccinimide (0.39 g, 2.91 mmol) was added in small portions over a 5 minute period. Stirring was continued for 1 h and 15 min. The solvent was removed under reduced pressure. Ethyl acetate (~90 mL) and saturated aqueous sodium bicarbonate were added. The organic layer was separated and washed three times with saturated aqueous sodium bicarbonate and brine. The organic layer was separated, dried over sodium sulfate, filtered and evaporated under vacuum to yield 1.06 g (105%) of the desired product as a light pink solid. M+H+=318.23, 320.23

A60.3: N-[(4-methoxyphenyl)methyl]-8-methyl-N-(tertbutoxycarbonyl)-2-(methylthio)-8H-imidazo[4,5-d]thiazolo[4,5-b]pyridin-5-amine

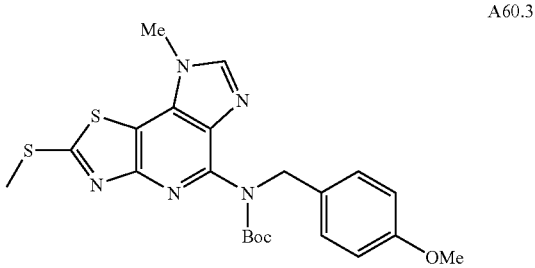

A60.2 (630 mg, 1.51 mmol) and potassium O-ethylxanthate (990 mg, 6.04 mmol) was dissolved in DMF (40 mL) and heated to 170° C. under an argon atmosphere for 3 h. HPLC analysis at this time demonstrated 91% conversion. Additional xanthate (0.24 g, 1.5 mmol) was added and reaction continued at 170° C. for 1 h. The reaction mixture was allowed to cool to room temperature then immersed in an ice bath. Methyl iodide (1.66 g, 11.78 mmol) was added, the flask sealed and the reaction mixture was stirred for 1.5 h. The solvent was removed by vacuum distillation. The crude product was partitioned between ethyl acetate and water. The organic layer was washed with water (2x), then with brine. The organic layer was dried with sodium sulfate, filtered and the solvent removed under reduced pressure to yield 740 mg of crude product as a tan glassy solid. The product was purified by silica gel flash column chromatography (hexane/ethyl acetate 1:1→ethyl acetate/methanol 98:2) to provide 390 mg of the desired product as a tan glass. M+H+=472.21

A60.4: N-[(4-methoxylphenyl)methyl]-8-methyl-N-(tertbutoxycarbonyl)-2-(methylsulfonyl)-8H-imidazo[4,5-d]thiazolo[4,5-b]pyridin-5-amine

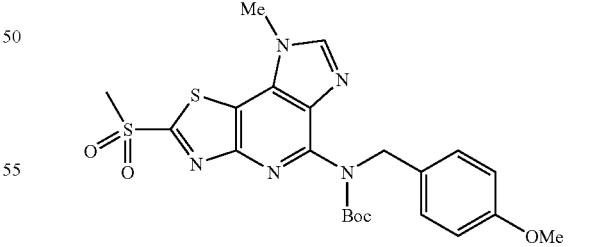

Oxone® (1.48 g, 2.42 mmol) was dissolved in water (10 mL) and added dropwise to a solution of A60.3 (380 mg, 0.81 mmol) in THF (18 ml). The reaction mixture was stirred vigorously for 2 h. Additional THF (10 mL) was added and the reaction stirred for an additional 16h. Analysis of the reaction mixture demonstrated a mixture of sulfoxide and sulfone products. The THF was removed under reduced pressure and the remaining precipitate collected, rinsed with additional water and dried under vacuum to yield a pale yellow solid (420 mgs). Oxone® (0.99 g, 1.6 mmol) was dissolved in water (10 mL) and added to a solution of the crude product in THF (10 mL). The reaction mixture was stirred for several hours and an additional equivalent of Oxone® solution was added along with a little methanol and stirring was continued for an additional 16 h. The volitiles were removed under reduced pressure and the precipitate was cooled in an ice bath, when precipitation was judged complete the product was collected by filtration and rinsed with water. The solid was dried under vacuum, rinsed with hexane and dried again to yield 390 mg (95%) of the desired product as a very pale tan solid. M+H+=504.17

A60.5: N-[(4-methoxylphenyl)methyl]-8-methyl-N-(tertbutoxycarbonyl)-2-hydrazino-8H-imidazo[4,5-d]thiazolo[4,5-b]pyridin-5-amine

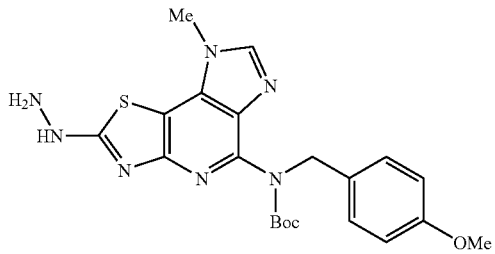

A60.5

A60.4 (314 mg, 0.62 mmol) was suspended in ethanol (4.3 ml). hydrazine hydrate (12.4 mL) was added and the reaction mixture refluxed for 30 min. The reaction mixture was allowed to cool to room temperature and the volatiles removed under reduced pressure. The residue was treated with water (~3 mL) and the suspension cooled in an ice bath to aid precipitation. The solid was collected by filtration, rinsed with water and dried under vacuum to yield 233 mg (82%) of the desired product as a pale yellow solid. M+H+=456.22.

A60.6: N-[(4-methoxylphenyl)methyl]-8-methyl-N-(tertbutoxycarbonyl)-2-bromo-8H-imidazo[4,5-d]thiazolo[4,5-b]pyridin-5-amine

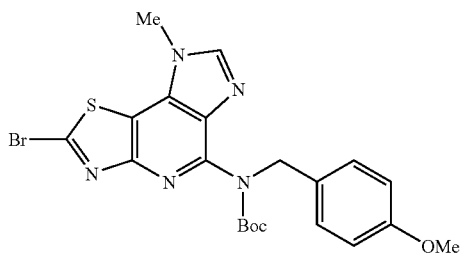

A60.6

Copper (II) bromide (0.11 g, 0.48 mmol) and amyl nitrite (62 mg, 0.6 mmol) were suspended in acetonitrile (10 mL) and degassed by passing a stream of argon through the mixture for several minutes. A60.5 (183 mg, 0.40 mmol) was added in several portions and stirring was continued for 17 minutes. After HPLC analysis (~10 minutes) the reaction mixture was diluted with ethyl acetate (35 mL) and the organic layer was washed with a 1:1 mixture of saturated ammonium chloride/conc. Ammonium hydroxide (4×10 mL) followed by brine. The organic layer was dried over sodium sulfate, filtered and the solvent removed under reduced pressure to yield 220 mg (109%) of the desired product. M+H+=506.06, 508.06

A60.7: N-[(4-methoxylphenyl)methyl]-8-methyl-N-(tertbutoxycarbonyl)-2-phenyl-8H-imidazo[4,5-d]thiazolo[4,5-b]pyridin-5-amine

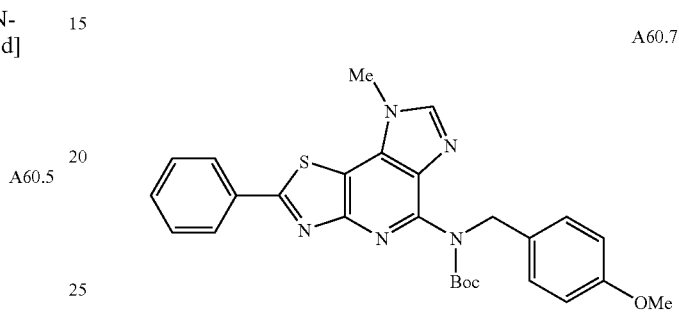

A60.7

A60.6 (220 mg., 0.44 mmol), phenylboronic acid (53.6 mg, 0.44 mmol) and tetrakis(triphenylphosphine)palladium (0) (50 mg, 0.44 mmol) were added to a mixture of 2M aqueous sodium carbonate (0.94 mL), ethanol (2.2 mL) and dioxane (2.2 mL). The reaction mixture was heated at 100° C. for 3 h, 15 min. The solvents were removed under reduced pressure and water (~10 mL) was added. The reaction mixture was sonicated and the crude product collected by filtration. The precipitate was washed with an additional portion of water and dried under vacuum to yield 340 mg (~100%) of the desired product as a tan solid. M+H+=502.25

A60.8: 8-methyl-2-phenyl-8H-imidazo[4,5-d]thiazolo[4,5-b]pyridin-5-amine

A60.7 (370 mg) was dissolved in trifluoroacetic acid and stirred at 50° C. for 2h and 45 min. then at 60° C. for 2 h, then overnight at room temperature. The solvent was removed under reduced pressure and co-evaporated with diethyl ether (2×). Ether (~20 mL) was added and the mixture sonicated for 1 min. The crude product was collected by filtration and rinsed with an additional portion of ether and dried under vacuum to yield 130 mg of a pale yellow solid. The crude product was washed with several portions of saturated aqueous sodium bicarbonate then water and dried under vacuum. The crude product was purified by automated reverse phase HPLC. The appropriate fractions were combined and azeotroped with heptane to produce 43 mg of a pale yellow solid. The solid was treated with a few milliliters of saturated aqueous sodium bicarbonate solution rinsed with water and dried under vacuum over phosphorus pentoxide and subsequently rinsed with several portions of diethyl ether and dried to yield 36 mg of the desired product. (Caution: This material was subjected to Ames testing and found to be positive in T98 with S9 activation. Suitable precautions should be taken in handling this material) $_1$H NMR 400 MHz d$^6$DMSO δ: 8.26 s, 1H, 8.14-8.07 m, 2H, 7.62-7.53, m, 3H, 6.90-6.80, br s, 2H, 4.02, s, 3H.

TABLE A4

Examples A61-A62 described in Table A4 were prepared in a similar manner to that described for the preparation of the compounds in table A3. Caution-although the compounds in the table below have not been tested in the Ames assay it would be prudent to consider these compounds as if they were positive and handle these with the appropriate precautions.

| Ex. | R¹ | Name | HPLC Retention (min) | MS Reported |
|---|---|---|---|---|
| A61 | CH$_3$— | N-[[3-(5-amino-8-methyl-8H-imidazo[4,5-d]thiazolo[4,5-b]pyridin-2-yl)phenyl]methyl]acetamide | 1.10 | 353.32 |
| A62 | MeO-CH$_2$CH$_2$- (3-methoxypropyl) | N-[[3-(5-amino-8-methyl-8H-imidazo[4,5-d]thiazolo[4,5-b]pyridin-2-yl)phenyl]methyl]-3-methoxypropanamide, | 1.22 | 397.33 |

Utility

The compounds of the invention are inhibitors of IKK. Accordingly, compounds of formula (I) have utility in treating conditions were a decrease in NF-κB activity would be beneficial. Such conditions include diseases or disorders in which cytokine levels are modulated as a consequence of intracellular signaling via IKK, and in particular, diseases that are associated with an overproduction of cytokines IL-1, IL-4, IL-8, and TNF-α. As used herein, the terms "treating" or "treatment" encompass responsive and/or prophylaxis measures addressed to the disease state and/or its sypmtoms, e.g., measures designed to inhibit or delay the onset of the disease or disorder, achieve a full or partial reduction of the symptoms or disease state, and/or alleviate, lessen, or cure the disease and/or its symptoms. When reference is made herein to inhibition of "IKK," this means that either or both IKK-2 and IKK-1 are inhibited.

In view of their activity as inhibitors of IKK, compounds of Formula (I) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the inventive compounds may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions); glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenze, cerebral malaria, silicosis, bone resorption disease, fever, myalgias due to infection, osteoporosis, multiple myeloma-related bone disorder, neurodegenerative disease caused by traumatic injury, and traumatic brain injury.

The inventive compounds may also be used to treat acute or chronic graft vs host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to scar tissue formation, eczema, atopic dermatitis, contact dermatitis, urticaria, schleroderma, scleraclerma, and psoriasis. The inventive compounds also may be used to treat allergies and respiratory conditions, including asthma, acute respiratory distress syndrome, hayfever, allergic rhinitis, and any chronic pulmonary inflammatory disease such as chronic obstructive pulmonary disease. The compounds further may be used to treat steroid resistance in asthma and allergies.

Additionally, the inventive compounds may be used to treat inflammation associated with autoimmune diseases including, but not limited to, systemic lupus erythematosis, Addison's disease, autoimmune polyglandular disease (also known as autoimmune polyglandular syndrome), and Grave's disease. The inventive compounds may be used to infectious diseases such as sepsis, septic shock, Shigellosis, and Heliobacter Pylori.

The compounds may be used to treat viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS/ARC or malignancy, and herpes.

The inventive compounds also may be used to treat angiogenic disorders including solid tumors, ocular neovascularization, and infantile haemangiomas.

In addition, IKK inhibitors of this invention inhibit the expression of inducible pro-inflammatory proteins such as prostaglandin endoperoxide synthase-2 (PGHS-2), also referred to as cyclooxygenase-2 (COX-2). Accordingly, additional conditions that may be treated with the inventive compounds include edema, analgesia and pain, such as neuromuscular pain, headache, pain caused by cancer or surgery, dental pain and arthritis pain. In view of their COX-2 inhibitory activity, the inventive compounds also may be used to treat cancer including without limitation epithelial cancer and adenocarcinoma.

In addition, IKK (+/−) mice when fed a high fat diet have reduced insulin levels and reduced blood glucose levels. Accordingly compound of this invention are useful in the treatment of Type II diabetes (also known as non-insulin dependant diabetes).

Additionally, the compounds of this invention are useful to treat ischemia, including ischemia resulting from vascular occlusion, cerebral infarction, stroke, and related cerebral vascular diseases (including cerebrovascular accident and transient ischemic attack). Accordingly, the compounds may be used to treat myocardial infarction, coronary artery disease, non-Q wave MI, congestive heart failure, ventricular hypertrophy, cardiac arrhythmias, unstable angina, chronic stable angina, Prinzmetal's angina, high blood pressure, intermittent claudication, silent ischemia, cardiac hypertrophy, and peripheral occlusive arterial disease (e.g., peripheral arterial disease, critical leg ischemia, prevention of amputation, and prevention of cardiovascular morbidity such as MI, stroke or death).

Additionally, in view of their activity in treating ischemia, the compounds of the invention may be useful to treat symptoms or consequences occurring from thrombosis, atherosclerosis, peripheral arterial disease, and thrombotic or thromboembolic symptoms or consequences associated with and/or caused by one or more of the following: thromboembolic stroke (including that resulting from atrial fibrillation or from ventricular or aortic mural thrombus), venous thrombosis (including deep vein thrombosis), arterial thrombosis, cerebral thrombosis, pulmonary embolism, cerebral embolism, thrombophilia (e.g., Factor V Leiden, and homocystinenimia), coagulation syndromes and coagulopathies (e.g., disseminated intravascular coagulation), restenosis (e.g., following arterial injury induced endogenously or exogenously), atrial fibrillation, and ventricular enlargement (including dilated cardiac myopathy and heart failure). The compounds of the invention also may be used to treat symptoms or consequences of atherosclerotic diseases and disorders, such as atherosclerotic vascular disease, atherosclerotic plaque rupture, atherosclerotic plaque formation, transplant atherosclerosis, and vascular remodeling atherosclerosis. The compounds of the invention further may be used to treat symptoms or consequences of thrombotic or thromboembolic conditions associated with cancer, surgery, inflammation, systematic infection, artificial surfaces (such as stents, blood oxygenators, shunts, vascular access ports, vascular grafts, artificial valves, etc.), interventional cardiology such as percutaneous transluminal coronary angioplasty (PTCA), immobility, medication (such as oral contraceptives, hormome replacement therapy, and heparin), pregnancy and fetal loss, and diabetic complications including retinopathy, nephropathy, and neuropathy.

The compounds of the present invention may be used for the preservation of tissue, for example, the preservation of tissue as relates to organ transplantation and surgical manipulation. The compounds may be used to treat diseases or disorders in other tissues or muscles that are associated with ischemic conditions and/or to enhance the strength or stability of tissue and muscles. For example, the compounds may be used to treat muscle cell damage and necrosis and/or to enhance athletes' performance.

Additional diseases and disorders that may be treated with the inventive compounds include irritable bowel syndrome, leukemia, CNS disorders associated with cerebral ischemia, such as cerebral infarction, cerebral edema and the like, and diseases associated with proliferation of smooth muscle cells, mesangial cells, and fibroblasts. Such diseases include renal fibrosis, hepatic fibrosis, prostate hypertrophy, and pulmonary fibrosis.

The inventive compounds also may be used to treat veterinary viral infections, such as lentivirus infections, including, but not limited to, equine infectious anemia virus; or retro virus infections, including feline immunodeficiency virus, bovine immunodeficiency virus, and canine immunodeficiency virus.

The inventive compounds are also effective in treating oncological diseases, in treating cancer and tumors, such as solid tumors, lymphomas and leukemia, and in particular, breast cancer, prostate cancer, and Hodgkin's lymphoma.

Additionally this invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid or liquid tumors which are associated with IKK, especially those tumors which are significantly dependent on IKK for their growth and spread, including for example, hematopoietic tumors, cancers of the bladder, squamous cell, head, colorectal, oesophageal, gynecological (such as ovarian), pancreas, breast, prostate, lung, vulva, skin, brain, genitourinary tract, lymphatic system (such as thyroid), stomach, larynx and lung.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of the skin, including melanoma;

hematopoietic tumors including those of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

hematopoietic tumors including those of plasma cell lineage such as multiple myeloma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of IKK kinase activity, such as melanomas, and multiple myeloma. By the administration of a composition (or a combination) of the compounds of this invention, development of tumors in a mammalian host is reduced.

The invention also provides a pharmaceutical composition comprising a compound of formula I in combination with pharmaceutically acceptable carrier and an anti-cancer or cytotoxic agent. In a preferred embodiment said anti-cancer or cytotoxic agent is selected from the group consisting of linomide; inhibitors of integrin αvβ3 function; angiostatin; razoxin; tamoxifen; toremifen; raloxifene; droloxifene; iodoxyfene; megestrol acetate; anastrozole; letrozole; borazole; exemestane; flutamide; nilutamide; bicalutamide; cyproterone acetate; gosereline acetate; luprolide; finasteride; metalloproteinase inhibitors; inhibitors of urokinase plasminogen activator receptor function; growth factor antibodies; growth factor receptor antibodies such as Avastin® and Erbitux®; tyrosine kinase inhibitors; serine/threonine kinase inhibitors); methotrexate; 5-fluorouracil; purine; adenosine analogues; cytosine arabinoside; doxorubicin; daunomycin; epirubicin; idarubicin; mitomycin-C; dactinomycin; mithramycin); cisplatin; carboplatin; nitrogen mustard; melphalan; chlorambucil; busulphan; cyclophosphamide; ifosfamide nitrosoureas; thiotephan; vincristine; Taxol®; Taxotere®; epothilone analogs; discodermolide analogs; eleutherobin analogs; etoposide; teniposide; amsacrine; topotecan; and flavopyridols.

In the field of medical oncology it is normal practice to use a combination of different forms of treatment to treat each patient with cancer. In medical oncology the other component(s) of such conjoint treatment in addition to the antiproliferative, antiangiogenic and/or vascular permeability reducing treatment defined herein before may be: surgery, radiotherapy or chemotherapy. Such chemotherapy may cover three main categories of therapeutic agent:

1: antiangiogenic agents such as inhibitors of VEGF or related kinases (such as FLT, or KDR), linomide, antibodies which block angiogenesis, inhibitors of integrin αvβ3 function, angiostatin, razoxin;

2: cytostatic agents such as antiestrogens (for example tamoxifen, toremifen, raloxifene, droloxifene, iodoxyfene), progestogens (for example megestrol acetate), aromatase inhibitors (for example anastrozole, letrazole, borazole, exemestane), antiharmones, antiprogestogens, antiandrogens (for example flutamide, nilutamide, bicalutamide, cyproterone acetate), LHRH agonists and antagonists (for example gosereline acetate, luprolide), inhibitors of testosterone 5α-dihydroreductase (for example finasteride), farnesyltransferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such inhibitors include growth factor antibodies, growth factor receptor antibodies such as Avastin® and Erbitux®, tyrosine kinase inhibitors and serine/threonine kinase inhibitors);

3: antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotephan); antimitotic agents (for example vinca alkaloids like vincristine and taxoids like Taxol®, Taxotere® and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors (for example flavopyridols).

The present invention thus provides methods for treating such conditions, comprising administering to a subject in need thereof an effective amount of at least one compound of formula I or a salt thereof. Other therapeutic agents such as those described herein may be employed in combination with compounds of formula I. In the methods of the present invention, such other therapeutic agent(s) may be administered prior to, simultaneously with, or following administration of the inventive compound(s).

When the terms "IKK associated condition" or "IKK associated disease or disorder" are used herein, each is intended to encompass all of the conditions identified above as if repeated at length, as well as any other condition that is modulated by IKK kinase activity.

The present invention thus provides methods for treating such conditions, comprising administering to a subject in need thereof an effective amount of at least one compound of Formula (I), or a pharmaceutically-acceptable salt, hydrate, or prodrug thereof. The methods of treating IKK kinase-associated conditions may comprise administering compounds of Formula (I) alone or in combination with each other and/or other suitable therapeutic agents such as anti-inflammatory drugs, antibiotics, anti-viral agents, anti-oxidants, cholesterol/lipid lowering agents, anti-tumor agents including antiproliferative agents, and agents used to treat ischemia.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, enbrel, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CellCept®] and VX-497), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), other p38 mitogen-activated protein kinase inhibitors, protein tyrosine kinase (PTK) inhibitors, therapies for the treatment of irritable bowel syndrome (e.g., Zelmac®, Zelnorm®, and Maxi-K® openers such as those disclosed in U.S. Pat. No. 6,184,231 B1), corticosteroids (such as beclomethasone, triamcinolone, budesonide, fluticasone, flunisolide, dexamethasone, prednisone, and dexamethasone); disassociated steroids; chemokine receptor modulators (including CCR1, CCR2, CCR3, CCR4, and CXCR2 receptor antagonists); secretory and cytosolic phospholipase A2 inhibitors, VLA4 antagonists, glucocorticoids, salicylates, nitric oxide, and other immunosuppressants; and nuclear translocation inhibitors, such as deoxyspergualin (DSG).

To treat pain, the inventive compounds may be used in combination with aspirin, NSAIDs, or with 5-HT 1 receptor agonists such as buspirone, sumitriptan, eletriptan or rizatriptan, or with opioids (e.g. morphine, codeine, hydomorphone).

Examples of suitable diabetic agents with which the inventive compounds may be used include insulin (of porcine or recombinant human origin including, short acting insulins such as Humalog®, Regular, intermediate acting insulins such NPH, lente, and long acting insulins such as ultralente or glarginine(Lantus®)); sulfonylureas such as glyburide and glipizide; secretegogues such as repaginide, and nateglinide; Peroisome proliferators-activated receptor (PPAR) agonists such as rosiglitazole and pioglitazone, and mixed PPAR alpha/gamma dual agonists agonists such as muriglitazar; biquanides such as metformin, and glucosidase inhibitors such as acarbose and miglitol, PPAR-alpha agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

Examples of suitable antibiotics with which the inventive compounds may be used include β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin) metabolite-based anti-biotics (e.g., sulfonamides and trimethoprim); polyring systems (e.g., tetracyclins and rifampins); protein synthesis inhibitors (e.g., zyvox, chlorophenicol, clindamycin, etc.); and nitro-class antibiotics (e.g., nitrofurans and nitroimidazoles).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

A further use of the compounds of this invention is in combination with steriodal or non-steroidal progesterone receptor agonists ("PRA"), such as levonorgestrel, medroxyprogesterone acetate (MPA).

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The inventive compounds may also be useful in combination with anticancer strategies and chemotherapies such as taxol and/or cisplatin. The compounds may be used in conjunction with antitumor agents such as paclitaxel, adriamycin, epithilones, cisplatin, and carboplatin.

In view of their usefulness in treating ischemia, the inventive compounds may be used in combination with agents for inhibiting $F^1F^0$-ATPase, including efrapeptin, oligomycin, autovertin B, azide, and compounds described in U.S. patent application Ser. No. 60/339,108, filed Dec. 10, 2001 and assigned to the present assignee; -alpha- or beta-adrenergic blockers (such as propranolol, nadolol, carvedilol, and prazosin), or -β-adrenergic agonists (such as albuterol, terbutaline, formoterol, salmeterol, bitolterol, pilbuterol, and fenoterol); antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); $K_+$ channel modulators such as $I^{Ach}$ inhibitors and inhibitors of the $K^v1$ subfamily of $K_+$ channel openers such as $I^{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y^1$ and $P2Y^{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

Additionally, the inventive compounds may be used in combination with lipid profile modulators and antiatherosclerotic agents including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, atavastatin or visastatin), pravachol, squalene synthetase inhibitors, fibrates, bile acid sequestrants (such as questran), niacin and niacin/statin combinations, lipooxygenase inhibitors, ileal $Na_+$/bile acid cotransporter inhibitors, ACAT1 inhibitors, ACAT2 inhibitors, dual ACAT1/2 inhibitors, microsomal triglyceride transport protein inhibitors (such as disclosed in U.S. Pat. Nos. 5,739,135, 5,712,279 and 5,760,246), cholesterol absorption inhibitors (such as Zetia®), cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of IKK enzyme activity.

The inventive compounds have been tested and have shown activity as inhibitors of IKK, IkB, NF-κB and/or TNF-α. For example, THP-1 (human monocytic cell line) obtained from ATCC was cultured in RPMI-1640 supplemented with 10% FBS, sodium pyruvate, HEPES, 5-mercaptoethanol, Penicillin/Streptomycin. To a 96-well plate containing THP-1 cells (1.4×10$_6$/mL, 2.5×10$_5$ cells/well) in 180 μL RPMI-1640 was added 10 μL of the test compound in 10% DMSO. Typically, test compound concentrations of 0.1-100 μM were used in the assay. After one hour at 37° C., 10 μL of 1000 ng/mL lipopolysaccharide (LPS from *Salmonella typhosa*, Sigma) was added to each well. After an additional 6 hours at 37° C., the supernatants were collected following a 5 minute centrifugation of the plate to pellet the cells. The amount of TNFα in these supernatants was then measured using a TNFα-specific ELISA (Pharmingen). After subtracting out the amount of TNFα in a control that had not been treated with LPS, the percent inhibition was calculated versus a control that was treated with LPS but with no test compound added. The compounds of this invention are active in vivo in the LPS-induced TNFαsecretion model. Likewise, assays known in the field are applied to establish the activity of the compounds as inhibitors of IKK, IkB, and/or the NF-κB pathway.

TNFα Secretion Assay

The ability of compounds to inhibit the production and secretion of TNFα from leukocytes was performed using either PBMC (obtained as described above) or the THP-1 cell line as a source of monocytes. Compounds were diluted in RPMI 1640 supplemented with 10% FBS and DMSO at a final concentration of 0.2%. Cells (2×105/well in U-bottom 96 well plates) were pre-incubated with compounds for 30 min at 37 C prior to addition of lipopolysaccharide (LPS) at a final concentration of 6.25 ng/ml in a total volume of 200 μL. After 4 h at 37° C., 50 μL of supernatant was carefully aspirated for detection of soluble TNFα. Soluble TNFαwas detected by ELISA developed by R&D Systems (Minneapolis, Minn.) according to the manufacturer's instructions.

We claim:

1. A compound of formula (I),

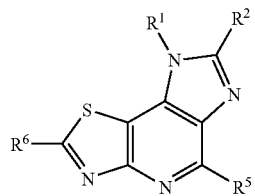

(I)

enantiomers, diastereomers, and salts, thereof wherein
$R^1$ is selected from hydrogen, and $C_{1-3}$ alkyl;
$R^2$ is hydrogen;
$R^5$ is —$NR^3R^4$;
$R^3$ and $R^4$ are independently selected from
  (a) hydrogen,
  (b) alkyl;
$R^6$ is
  aryl, which may be optionally independently substituted as valence allows with one or more $Z^{1d}$, $Z^{2d}$ and $Z^{3d}$; or —$SR^{7a}$, or —$N(R^{8a})C(O)R^{7a}$;
$R^{7a}$ is independently
  (a) hydrogen, or
  (b) alkyl, or aryl;
$R^{8a}$ is hydrogen,
$Z^{1a-1e}$, $Z^{2a-2e}$, $Z^{3a-3e}$ are optional substituents at each occurrence independently selected from —$W^1$—$V^1$; —$W^2$—$V^2$; —$W^3$—$V^3$; —$W^4$—$V^4$; —$W^5$—$V^5$;
where $W^{1-5}$ are independently
  (1) a bond, or
  (2) alkyl, cycloalkyl, aryl; or
where $V^{1-5}$ are independently
  (1) H
  (2) alkyl;
  (3) —$U^1$—O—$Y^5$,
  (6) —$U^1$—S(O)$_t$$Y^5$, where t is 2,
  (7) —$U^1$-halo,
  (8) —$U^1$-cyano,
  (10) —$U^1$—$NY^2Y^3$,
  (11) —$U^1$—N($Y^4$)—C(O)—$Y^1$,
  (15) —$U^1$—N($Y^4$)—C(O)O—$Y^5$,
  (18) —$U^1$—C(O)—$NY^2Y^3$,
  (24) oxo;
$Y^1$, $Y^2$, $Y^3$, $Y^4$ and $Y^5$
  (1) are each independently hydrogen, alkyl, cycloalkyl, piperidinyl, pyrrolodinyl, 5-oxo-pyrrolidinyl, 6-oxo-piperidinyl, furanyl, isoxazolyl, pyridinyl, pyrazinyl, pyridazinyl, thiadiazolyl, imidazolyl any of which may be optionally independently substituted as valence allows with one or more $Z^4$, $Z^5$ and $Z^6$; or
$Z^4$, $Z^5$, and $Z^6$ are optional substituents at each occurrence independently selected from
  (1) H
  (2) alkyl;
  (3) —$U^1$—O—$Y^{5a}$,
  (6) —$U^1$—S(O)$_t$$Y^{5a}$,
  (7) —$U^1$-halo,
  (8) —$U^1$-cyano,
  (10) —$U^1$—$NY^{2a}Y^{3a}$,
  (11) —$U^1$—N($Y^{4a}$)—C(O)—$Y^{1a}$,
  (24) oxo;
$Y^{1a}$, $Y^{2a}$, $Y^{3a}$, $Y^{4a}$ and $Y^{5a}$
  (1) are each independently hydrogen, alkyl;
$U^1$ is independently
  (1) a single bond,
  (2) alkylene,
  (3) alkenylene, or
  (4) alkynylene.

2. A compound of claim 1 wherein
$R^1$ is hydrogen, methyl, ethyl, propyl, or i-propyl; and
$R^2$ is hydrogen.

3. A compound of claim 1 wherein
$Z^{1d}$, $Z^{2d}$ and $Z^{3d}$ are optional substituents independently selected from
  (a) cyano, halo, —OH, —$OY^5$, —$U^1$—$NY^2Y^3$, —S(O)$_t$$Y^5$;
  (b) alkyl optionally substituted with one or more cyano, halo, —OH, —$OY^5$, —$U^1$—$NY^2Y^3$, —$U^1$—N($Y^4$)—C(O)—$Y^1$, —C(O)—$NY^2Y^3$, —S(O)$_t$$Y^5$.

4. A compound of claim 3 wherein
$R^3$ is hydrogen;
$R^4$ is alkyl;
$R^6$ is
  aryl optionally independently substituted as valence allows with one or more $Z^{1d}$, $Z^{2d}$ and $Z^{3d}$; or
$Z^{1d}$, $Z^{2d}$ and $Z^{3d}$ are optional substituents independently selected from (a) cyano, halo, —OH, —OY$^5$, —S(O)$_t$Y$^5$, or
(b) alkyl optionally substituted with one or more cyano, halo, —OH, —OY$^5$, —U$^1$—NY$^2$Y$^3$, —C(O)—NY$^2$Y$^3$, —S(O)$_t$Y$^5$, or —U$^1$—N(Y$^4$)—C(O)—Y$^1$, where
U$^1$ is a bond or alkylene.

5. A compound of claim 4 wherein
R$^1$ is C$_{1-3}$ alkyl; and
R$^2$ is hydrogen.

6. A compound of claim 1, wherein the compound is selected from:

N,8-Dimethyl-2-(methylthio)-8H-imidazo[4,5-d]thiazolo[4,5-b]pvridin-5-amine;
N,8-Dimethyl-2-(phenylcarbonylamino)-8H-imidazo[4,5-d]thiazolo[4,5-b]pyridin-5-amine;
N-Methyl-2-phenyl-8H-imidazo[4,5-d]thiazolo[4,5-b]pyridin-5-amine;
(S)-N-[1-[5-[8-methyl-5-(methylamino)-8H-imidazo[4,5-d]thiazolo[4,5-b]pyridine-2-yl]phenyl]ethyl]acetamide;
(R)-N-[1-[5-[8-methyl-5-(methylamino)-8H-imidazo[4,5-d]thiazolo[4,5-b]pyridine-2-yl]phenyl]ethyl]acetamide;
2-[8-methyl-5-(methylamino)-8H-imidazo[4,5-d]thiazolo[4,5-b]pyridin-2-yl]-benzamide;
2-(3-fluorophenyl)-N,8-dimethyl-8H-imidazo[4,5-d]thiazolo[4,5-b]pyridin-5-amine;
2-[4-(aminomethyl)phenyl]-N,8-dimethyl-8H-imidazo[4,5-d]thiazolo[4,5-b]pyridin-5-amine;
N-[[4-[8-methyl-5-(methylamino)-8H-imidazo[4,5-d]thiazolo[4,5-b]pyridin-2-yl]phenyl]methyl]acetamide;
N-[[4-[8-methyl-5-(methylamino)-8H-imidazo[4,5-d]thiazolo[4,5-b]pyridin-2-yl]phenyl]methyl]-1-piperidinepropanamide;
2-amino-N-[[4-[8-methyl-5-(methylamino)-8H-imidazo[4,5-d]thiazolo[4,5-b]pyridin-2-yl]phenyl]methyl]-acetamide;
N-[[4-[8-methyl-5-(methylamino)-8H-imidazo[4,5-d]thiazolo[4,5-b]pyridin-2-yl ]phenyl]methyl]-, (2S)-2-pyrrolidinecarboxamide;
N-[[4-[8-methyl-5-(methylamino)-8H-imidazo[4,5-d]thiazolo[4,5-b]pyridin-2-yl ]phenyl]methyl]-, (2R)-2-pyrrolidinecarboxamide;
N-[[4-[8-methyl-5-(methylamino)-8H-imidazo[4,5-d]thiazolo[4,5-b]pyridin-2-yl ]phenyl]methyl]-3-(methylsulfonyl)-benzamide;
5-methyl-N-[[4-[8-methyl-5-(methylamino)-8H-imidazo[4,5-d]thiazolo[4,5-b]pyridin-2-yl]phenyl]methyl]-3-isoxazolecarboxamide;
N-[[4-[8-methyl-5-(methylamino)-8H-imidazo[4,5-d]thiazolo[4,5-b]pyridin-2-yl ]phenyl]methyl]-2,2-dimethyipropanamide;
N-[[4-[8-methyl-5-(methylamino)-8H-imidazo[4,5-d]thiazolo[4,5-b]pyridin-2-yl ]phenyl]methyl]-2-pyridinecarboxamide;
N-[[4-[8-methyl-5-(methylamino)-8H-imidazo[4,5-d]thiazolo[4,5-b]pyridin-2-yl ]phenyl]methyl]cyclopropanecarboxamide;
N-[[4-[8-methyl-5-(methylamino)-8H-imidazo[4,5-d]thiazolo[4,5-b]pyridin-2-yl ]phenyl]methyl]-3-pyridineacetamide;
1-acetyl-N-[[4-[8-methyl-5-(methylamino)-8H-imidazo[4,5-d]thiazolo[4,5-b]pyridin-2-yl]phenyl]methy]-, (2S)-2-pyrrolidinecarboxamide:
N-[[4-[8-methyl-5-(methylamino)-8H-imidazo[4,5-d]thiazolo[4,5-b]pyridin-2-yl ]phenyl]methyl]-5-oxo-, (2S)-2-pyrrolidinecarboxamide;
2-methyl-N-[[4-[8-methyl-5-(methylamino)-8H-imidazo[4,5-d]thiazolo[4,5-b]pyridin-2-yl]phenyl]methy]-propanamide;
3,3dimethyl-N-[[4-[8-methyl-5-(methylamino)-8H-imidazo[4,5-d]thiazolo[4,5-b]pyridin-2-yl]phenyl]methy]-butanamide;
1-methyl-N-[[4-[8-methyl-5-(methylamino)-8H-imidazo[4,5-d]thiazolo[4,5-b]pyridin-2-yl]phenyl]methy]-cyclopropanecarboxamide;
N-[[4-[8-methyl-5-(methylamino)-8H-imidazo[4,5-d]thiazolo[4,5-b]pyridin-2-yl ]phenyl]methyl]-2-pyrazinecarboxamide;
N-[[4-[8-methyl-5-(methylamino)-8H-imidazo[4,5-d]thiazolo[4,5-b]pyridin-2-yl ]phenyl]methyl]-2-(methylsulfonyl)-benzamide;
tetrahydro-N-[[4-[8-methyl-5-(methylamino)-8H-imidazo[4,5-d]thiazolo[4,5-b]pyridin-2-yl]phenyl]methyl]-2-furancarboxamide;
2-ethoxy-N-[[4-[8-methyl-5-(methylamino)-8H-imidazo[4,5-d]thiazolo[4,5-b]pyridin-2-yl ]phenyl]methyl]-2-acetamide;
N-[[4-[8-methyl-5-(methylamino)-8H-imidazo[4,5-d]thiazolo[4,5-b]pyridin-2-yl ]phenyl]methyl]-4-pyridazinecarboxamide;
2-chloro-N-[[4-[8-methyl-5-(methylamino)-8H-imidazo[4,5-d]thiazolo[4,5-b]pyridin-2-yl]phenyl]methyl]-2-pyridinecarboxamide;
6-chloro-N-[[4-[8-methyl-5-(methylamino)-8H-imidazo[4,5-d]thiazolo[4,5-b]pyridin-2-yl]phenyl]methyl]-2-acetamide;
N-[[4-[8-methyl-5-(methylamino)-8H-imidazo[4,5-d]thiazolo[4,5-b]pyridin-2-yl ]phenyl]methyl]-3-pyridazinecarboxamide;
6-cyano-N-[[4-[8-methyl-5-(methylamino)-8H-imidazo[4,5-d]thiazolo[4,5-b]pyridin-2-yl]phenyl]methyl]-2-pyridinecarboxamide;
N-[[4-[8-methyl-5-(methylamino)-8H-imidazo[4,5-d]thiazolo[4,5-b]pyridin-2-yl ]phenyl]methyl]-benzeneacetamide;
1-methyl-N-[[4-[8-methyl-5-(methylamino)-8H-imidazo[4,5-d]thiazolo[4,5-b]pyridin-2-yl]phenyl]methyl]-4-pyridinecarboxamide;
1-methyl-N-[[4-[8-methyl-5-(methylamino)-8H-imidazo[4,5-d]thiazolo[4,5-b]pyridin-2-yl]phenyl]methyl]-3-pyridinecarboxamide;
N-[[4-[8-methyl-5-(methylamino)-8H-imidazo[4,5-d]thiazolo[4,5-b]pyridin-2-yl ]phenyl]methyl]-6-oxo-, (2S)-2-piperidinecarboxamide;
2-methoxy-N-[[4-[8-methyl-5-(methylamino)-8H-imidazo[4,5-d]thiazolo[4,5-b]pyridin-2-yl]phenyl]methyl]-acetamide;
6-methyl-N-[[4-[8-methyl-5-(methylamino)-8H-imidazo[4,5-d]thiazolo[4,5-b]pyridin-2-yl]phenyl]methyl]-2-pyridinecarboxamide;
3-methyl-N-[[4-[8-methyl-5-(methylamino)-8H-imidazo[4,5-d]thiazolo[4,5-b]pyridin-2-yl]phenyl]methyl]-2-pyridinecarboxamide;
N-[[4-[8-methyl-5-(methylamino)-8H-imidazo[4,5-d]thiazolo[4,5-b]pyridin-2-yl ]phenyl]methyl]-butanamide;
1-cyano-N-[[4-[8-methyl-5-(methylamino)-8H-imidazo[4,5-d]thiazolo[4,5-b]pyridin-2-yl]phenyl]methyl]-cyclopropanecarboxamide;
2-cyano-N-[[4-[8-methyl-5-(methylamino)-8H-imidazo[4,5-d]thiazolo[4,5-b]pyridin-2-yl]phenyl]methyl]-acetamide;

[[3-[8-methyl-5-(methylamino)-8H-imidazo[4,5-d]thiazolo[4,5-b]pyridin-2-yl]phenyl]methyl]carbamic acid 1,1-dimethylethyl ester;

2-[3-(aminomethyl)phenyl]N,8-dimethyl)-8H-imidazo[4,5-d]thiazolo[4,5-b]pyridin-5-amine;

N-[[3-[8-methyl-5-(methylamino)-8H-imidazo[4,5-d]thiazolo[4,5-b]pyridin-2-yl ]phenyl]methyl]acetamide;

N-[[4-[8-methyl-5-(methylamino)-8H-imidazo[4,5-d]thiazolo[4,5-b]pyridin-2-yl ]phenyl]methyl]cyclopropanecarboxamide;

2-(acetylamino)-N-[[3[8-methyl-5-(methylamino)-8H-imidazo[4,5-d]thiazolo[4,5-b]pyridin-2-yl]phenyl]methyl]acetamide;

N-[[4-[8-methyl-5-(methylamino)-8H-imidazo[4,5-d]thiazolo[4,5-b]pyridin-2-yl ]phenyl]methyl]-5-oxo-,(2R)-2-pyrrolidinecarboxamide;

N-[[4-[8-methyl-5-(methylamino)-8H-imidazo[4,5-d]thiazolo[4,5-b]pyridin-2-yl ]phenyl]methyl]-4-pyridinecarboxamide;

N-[[4-[8-methyl-5-(methylamino)-8H-imidazo[4,5-d]thiazolo[4,5-b]pyridin-2-yl ]phenyl]methyl]-1-piperidinepropanamide;

N-[[4-[8-methyl-5-(methylamino)-8H-imidazo[4,5-d]thiazolo[4,5-b]pyridin-2-yl ]phenyl]methyl]-2-(methylsulfonyl)-benzamide;

N-[[4-[8-methyl-5-(methylamino)-8H-imidazo[4,5-d]thiazolo[4,5-b]pyridin-2-yl ]phenyl]methyl]-4-piperidinepropanamide;

N-[[4-[8-methyl-5-(methylamino)-8H-imidazo[4,5-d]thiazolo[4,5-b]pyridin-2-yl ]phenyl]methyl]-1,2,3-thiadiazole-4-carboxamide;

N-[[4-[8-methyl-5-(methylamino)-8H-imidazo[4,5-d]thiazolo[4,5-b]pyridin-2-yl ]phenyl]methyl]-,(2R)-2-pyrrolidinecarboxamide;

1-hydroxy-N-[[3-[8-methyl-5-(methylamino)-8H-imidazo[4,5-d]thiazolo[4,5-b]pyridin-2-yl ]phenyl]methyl]-cyclopropanecarboxamide;

N-[[4-[8-methyl-5-(methylamino)-8H-imidazo[4,5-d]thiazolo[4,5-b]pyridin-2-yl ]phenyl]methyl]-2,2-dimethyl-propanamide;

1-methyl-N-[[4-[8-methyl-5-(methylamino)-8H-imidazo[4,5-d]thiazolo[4,5-b]pyridin-2-yl ]phenyl]methyl]-1H-imidazole-4-carboxamide;

1-methyl-N-[[4-[8-methyl-5-(methylamino)-8H-imidazo[4,5-d]thiazolo[4,5-b]pyridin-2-yl ]phenyl]methyl]-4-piperidinecarboxamide;

8-methyl-2-phenyl)-8H-imidazo[4,5-d]thiazolo[4,5-b]pyridin-5-amine;

N-[[3-(5-amino-8-methyl-8H-imidazo[4,5-d]thiazolo[4,5-b]pyridin-2-yl)phenyl]methyl]acetamide; and N-[[3-(5-amino-8-methyl-8H-imidazo[4,5-d]thiazolo[4,5-b]pyridin-2-yl)phenyl]methyl]-3-methoxypropanamide.

\* \* \* \* \*

UNITED STATES PATENT AND TRADEMARK OFFICE
CERTIFICATE OF CORRECTION

PATENT NO. : 7,557,211 B2
APPLICATION NO. : 11/271598
DATED : July 7, 2009
INVENTOR(S) : Jagabandhu Das et al.

It is certified that error appears in the above-identified patent and that said Letters Patent is hereby corrected as shown below:

COLUMN 86
Line 6, Claim 1, before "$Z^{3a-3e}$" insert -- and --.
Line 26, Claim 1, delete "pyrroldinyl," and insert -- pyrrolidinyl, --.
Line 66, Claim 4, before "$Z^{1d}$" insert -- $-SR^{7a}$, --.

COLUMN 87
Line 13, Claim 6, delete "pvridin" and insert -- pyridine --.
Lines 51-52, Claim 6, delete "dimethyipropanamide;" and insert
    -- dimethylpropanamide; --.
Line 63, Claim 6, delete "methy]-," and insert -- methyl]- --.
Line 64, Claim 6, delete "pyrrolidinecarboxamide:" and insert
    -- pyrrolidinecarboxamide; --.

COLUMN 88
Line 2, Claim 6, delete "methy]" and insert -- methyl] --.
Line 4, Claim 6, delete "3,3dimethyl" and insert -- 3,3-dimethyl --.
Line 5, Claim 6, delete "methy]" and insert -- methyl] --.
Line 8, Claim 6, delete "methy]" and insert -- methyl] --.
Line 26, Claim 6, after "methyl]" delete "-2-" and insert -- -3- --.
Lines 30-31, Claim 6, delete "2-acetamide;" and insert
    -- -3-pyridinecarboxamide; --.
Lines 33-34, Claim 6, delete "pyridazinecarboxamide;"
    and insert -- pyridinecarboxamide; --.
Line 36, Claim 6, after "methyl]" delete "-2-" and insert -- -3- --.
Line 43, Claim 6, delete "pyridinecarboxamide;" and
    insert -- piperidinecarboxamide; --.
Line 46, Claim 6, delete "pyridinecarboxamide;" and
    insert -- piperidinecarboxamide; --.

Signed and Sealed this

Twenty-seventh Day of July, 2010

David J. Kappos
*Director of the United States Patent and Trademark Office*

CERTIFICATE OF CORRECTION (continued)
U.S. Pat. No. 7,557,211 B2

COLUMN 89
Line 4, Claim 6, after "dimethyl" delete ")".
Line 8, Claim 6, delete "N-[[4-" and insert -- N-[[3- --.
Line 11, Claim 6, delete "[[3[8" and insert -- [[3-[8 --.
Line 14, Claim 6, delete "N-[[4-" and insert -- N-[[3- --.
Line 17, Claim 6, delete "N-[[4-" and insert -- N-[[3- --.
Line 20, Claim 6, delete "N-[[4-" and insert -- N-[[3- --.
Line 23, Claim 6, delete "N-[[4-" and insert -- N-[[3- --.
Line 26, Claim 6, delete "N-[[4-" and insert -- N-[[3- --.
Lines 27-28, Claim 6, delete "piperidinepropanamide;" and insert -- piperidinecarboxamide; --.

COLUMN 90
Line 1, Claim 6, delete "N-[[4-" and insert -- N-[[3- --.
Line 4, Claim 6, delete "N-[[4-" and insert -- N-[[3- --.
Line 10, Claim 6, delete "N-[[4-" and insert -- N-[[3- --.
Line 14, Claim 6, delete "N-[[4-" and insert -- N-[[3- --.
Line 18, Claim 6, delete "N-[[4-" and insert -- N-[[3- --.
Line 21, Claim 6, after "2-phenyl" delete ")".